United States Patent
Schoenberger et al.

(10) Patent No.: US 12,427,195 B1
(45) Date of Patent: Sep. 30, 2025

(54) METHODS OF NEOANTIGEN IDENTIFICATION

(71) Applicants: La Jolla Institute for Immunology, La Jolla, CA (US); The Regents of the University of California, Oakland, CA (US)

(72) Inventors: Stephen P. Schoenberger, San Diego, CA (US); Bjoern Peters, San Diego, CA (US); Alessandro Sette, San Diego, CA (US); Jason Greenbaum, San Diego, CA (US); Ezra Cohen, San Diego, CA (US); Aaron Miller, San Diego, CA (US)

( * ) Notice: Subject to any disclaimer, the term of this patent is extended or adjusted under 35 U.S.C. 154(b) by 573 days.

(21) Appl. No.: 16/816,160

(22) Filed: Mar. 11, 2020

Related U.S. Application Data

(60) Provisional application No. 62/816,885, filed on Mar. 11, 2019.

(51) Int. Cl.
| | |
|---|---|
| *A61K 40/42* | (2025.01) |
| *A61P 35/00* | (2006.01) |
| *C07K 14/47* | (2006.01) |
| *C12Q 1/6869* | (2018.01) |
| *C12Q 1/6886* | (2018.01) |

(52) U.S. Cl.
CPC .......... *A61K 40/4201* (2025.01); *A61P 35/00* (2018.01); *C07K 14/4748* (2013.01); *C12Q 1/6869* (2013.01); *C12Q 1/6886* (2013.01)

(58) Field of Classification Search
None
See application file for complete search history.

(56) References Cited

U.S. PATENT DOCUMENTS

| | | | |
|---|---|---|---|
| 2015/0017141 A1 | 1/2015 | June | |
| 2017/0199961 A1* | 7/2017 | Yelensky | G16H 20/10 |

FOREIGN PATENT DOCUMENTS

| | | | |
|---|---|---|---|
| WO | WO-2011143656 A2 * | 11/2011 | A61K 39/0011 |

OTHER PUBLICATIONS

Sallman et al (Integrating mutation variant allele frequency into clinical practice in myeloid malignancies, Hematology/Oncology and Stem Cell Therapy, 2016, 89-95, vol. 9) (Year: 2016).*
Martin et al (A library-based screening method identifies neoantigen-reactive T cells in peripheral blood prior to relapse of ovarian cancer. Oncoimmunology. 2017;7(1):e1371895. Published Sep. 21, 2017) (Year: 2017).*
Ahmad, et al., "scFv Antibody: Principles and Clinical Application" Clinical and Developmental Immunology, 2012: https://doi.org/10.1155/2012/980250.
Ausubel, et al. "Current Protocols in Molecular Biology" Supplement 30, section 7.7.18, Table 7.7.1.
Bjerregaard et al. "An Analysis of Natural T Cell Responses to Predicted Tumor Neoepitopes" (Nov. 14, 2017) Front. Immunol.).
Kotterman, et al., (2015) "Viral Vectors for Gene Therapy: Translational and Clinical Outlook," Annual Review of Biomedical Engineering.
Lundegaard et al. "NetMHC-3.0: accurate web accessible predictions of human, mouse and monkey MHC class I affinities for peptides of length 8-11" (May 7, 2008) Nucleic Acids Res.).
Negrini et al. "Genomic instability—an evolving hallmark of cancer" (Mar. 2010) Nat. Rev. Mol. Cell Biol.). 224-228.
OKeefe et al. "Scaleable manufacture of HIV-1 entry inhibitor griffithsin and validation of its safety and efficacy as a topical microbicide component" (Apr. 14, 2009) PNAS USA, 106(15):6099-6104).
Picelli et al. "Full-length RNA-seq from single cells using Smart-seq2" Published online Jan. 2, 2014; doi: 10.1038/nprot.2014.006, Nature Protocols, vol. 9 No. 1, 2014.
Rosales et al. "A sensitive and integrated approach to profile messenger RNA from samples with low cell numbers" (2018) Methods Mol. Biol.
Schumacher et al. "Genome-wide association study of colorectal cancer identies six new susceptibility loci" (published Jul. 7, 2015) Science). DOI: 10.1038/ncomms8138.

* cited by examiner

*Primary Examiner* — Zachariah Lucas
*Assistant Examiner* — Sarah A Alsomairy
(74) *Attorney, Agent, or Firm* — Edwin S. Flores; Daniel J. Chalker; Chalker Flores, LLP

(57) ABSTRACT

Systems and methods for identifying neoantigen peptide candidates are described. Such systems and methods can be used to generate engineered immune cells that target neoantigen peptides. In certain embodiments, the systems and methods do not require in silico epitope binding prediction algorithms. In certain embodiments, neoantigens are identified for a cancer or tumor with a low mutational burden.

10 Claims, 41 Drawing Sheets
(15 of 41 Drawing Sheet(s) Filed in Color)
Specification includes a Sequence Listing.

METHODS OF NEOANTIGEN IDENTIFICATION

CROSS REFERENCE TO RELATED APPLICATION

This Application claims priority to U.S. Provisional Patent Application No. 62/816,885, filed Mar. 11, 2019, and entitled "NOVEL NEOANTIGEN DISCOVERY PIPELINE", which is incorporated herein in its entirety.

FEDERALLY SPONSORED RESEARCH OR DEVELOPMENT

This invention was made with federal government support under NIH grant no. U01 DE028227. The government has certain rights in the invention.

INCORPORATION BY REFERENCE

The present application incorporates by reference a sequence listing, in electronic format, entitled 7888300100_SEQLIST.txt, created Jul. 14, 2020, which is 13.2 kb in size. The information in the electronic format of the sequence listing is incorporated herein by reference in its entirety.

FIELD

The present disclosure relates generally to the field of immunotherapy, and more specifically relates to the identification of neoantigens and their use in immunotherapy.

BACKGROUND

Genomic instability is a hallmark of cancer. In general, genomic instability orchestrates uncontrolled cell growth, resistance to treatment, and metastatic spread of cancer cells (see: Negrini et al. (2010) *Nat. Rev. Mol. Cell Biol.*). While genetic mutation disrupts many important features of cell homeostasis, it also produces unique identifiers, i.e., neoepitopes (also referred to herein as "neoantigens" or NeoAgs), which are presented by major histocompatibility complex (MHC) molecules on the surface of the cancer cell for immune recognition (see, for e.g.: Schumacher et al. (2015) *Science*).

Historically, targeted cancer immunotherapies have focused on tumor-associated antigens (TAAs) or fetal antigens that are overexpressed in tumors with the hope of developing an "off-the-self" product that is broadly applicable to a wide variety of cancer patients. Unfortunately, targeting of self-antigens carries an inherent risk of adverse immune related events and these efforts were largely met with failure and autoimmune toxicity (see, for e.g.: Morgan et al. (2014) *J. Immunother.*). In contrast, tumor-specific somatic mutations can produce neoantigens capable of generating robust antigen-specific responses and avoid off-target immune-related toxicity. Unfortunately, neoantigens are difficult to identify and are often not shared across tumor types given the immense genetic diversity both across and within tumors (see, for e.g.: Bjerregaard et al. (2017) *Front. Immunol.*). This genetic diversity poses a major challenge to the development of personalized adoptive T cell therapy and therapeutic vaccines where identification of tumor-specific neoantigens capable of eliciting autologous immune response is a critical determinant to success.

A process of tumor neoantigen identification involves next generation sequencing of a patient's tumor and normal tissue to pinpoint mutations unique to a patient's cancer, or mutations shared between one or more patients, followed by computational prediction of which mutations are most likely to be processed by the cell and loaded onto major histocompatibility complex class I (MHC-I) for recognition by T cells (see, for e.g.: Lundegaard et al. (2008) *Nucleic Acids Res.*). To date, these in silico prediction algorithms have been a necessary step for neoantigen identification for high mutation rate malignancies where the mutanome consists of thousands of non-synonymous mutations that must be narrowed prior to validation. Unfortunately, they also carry the real risk that de facto neoantigens will be untested and missed due to a low predicted binding affinity. To date, large-scale analyses of neoantigen-specific T cell reactivity in tumors have found that only a limited number of non-synonymous mutations result in neoantigens for which T cell reactivity can be detected. Another challenge is that most in silico tools focus on MHC-I binders; and algorithms for predicting MHC-II binders, which underlie CD4+ T-cell responses, are not as well refined due to longer epitope length and motif promiscuity.

The low rate of validating neoantigens by current tumor neoantigen prediction methods presents a major impediment for the widespread application of cancer immunotherapies targeting these mutations.

SUMMARY

In an aspect, a method of identifying a neoantigen peptide candidate is disclosed. The method involves generating tumor sequence reads from a tumor sample and normal sequence reads from a normal control sample; comparing the tumor sequence reads with the normal sequence reads to identify one or more exome variants; selecting from the one or more exome variants a set of exome variants that satisfy a variant calling policy; generating for at least one exome variant of the set of exome variants that satisfy the variant calling policy one or more peptides, each peptide having one or more mutated amino acids at one or more pre-selected locations of the peptide; and evaluating immunogenicity for one or more of the synthetic peptides. In certain embodiments, the peptides are synthetic peptides.

In embodiments, the method further involves identifying at least one peptide demonstrating a predetermined immunogenic activity as a neoantigen peptide candidate. In embodiments, the method is devoid of an in silico epitope binding prediction algorithm. In embodiments, the tumor sequence reads are tumor mRNA sequence reads, tumor exome sequence reads, or both. In embodiments, the non-tumor sequence reads are non-tumor exome sequence reads. In embodiments, the predetermined immunogenic activity comprises stimulation of a T cell response by the at least one peptide. In embodiments, the predetermined immunogenic activity comprises production of IFN-γ or IL-5 by a T cell. In embodiments, the T cell response is predominantly a CD4+ T cell response. In embodiments, the CD4+ T cell response is a Th1 or Th2 response. In embodiments, the T cell response is predominantly a CD8+ T cell response. In embodiments, the T cell response is both a CD4+ T cell response and a CD8+ T cell response. In embodiments, the method further involves producing the at least one identified peptide. In further embodiments, the method further involves treating an individual associated with the tumor sample with a composition comprising the at least one identified peptide, or an engineered immune cell that biologically recognizes the at least one peptide.

In another aspect, a neoantigen peptide is disclosed. In embodiments, the neoantigen peptide is produced based on the method of identification detailed herein. In another aspect, an engineered immune cell is disclosed. The engineered immune cell is configured to biologically recognize the neoantigen peptide detailed herein. In embodiments, the engineered immune cell comprises a CD4+ T cell, a CD8+ T cell, a tissue-resident memory cell ($T_{RM}$), a NKT cell, or a NK cell. In embodiments, the engineered immune cell comprises a chimeric antigen receptor (CAR). In embodiments, the CAR further comprises one or more costimulatory signaling regions. In embodiments, the neoantigen peptide or the engineered immune cell detailed herein is used to treat an individual having cancer.

In another aspect, an immune composition is disclosed. In embodiments, the immune composition includes a pharmaceutically acceptable carrier, diluent, or excipient; an adjuvant; and the at least one identified peptide detailed herein, or the engineered immune cell detailed herein. In another aspect, a method of treating cancer is disclosed. The method involves delivering a therapeutically effective amount of the immune composition detailed herein to an individual in need thereof. In another aspect, a prophylactic method of preventing cancer is disclosed. The method involves delivering a prophylactically effective amount of the composition described herein to an individual in need thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-B depict a schematic of an aspect of the method of neoantigen identification described herein. FIG. 2A depicts ELISPOT data for a series of peptide pools as detailed herein. FIG. 2B depicts representative data for PT-37 as detailed herein. FIGS. 3A-C depict de-convolution of the pool responses to single peptides demonstrating that 15 of the 38 neoantigen candidates identified by the described neoantigen pipeline stimulated T cell responses. FIGS. 4A-B summarize that 40% of the candidate neoantigens stimulated T-cell responses.

FIG. 5A shows functional T cell responses against the driver mutations KRAS G12V and passenger mutations NRXN2 R861 W and FRG2C Ni 19S. FIGS. 5B-D shows that res-stimulation of T cells from the 14-day co-culture with single mutant peptides on day 17 discerned distinct populations of CD8 and CD4 T cells producing IFN-γ and IL-5 that correlate with the ELISPOT results.

FIG. 11A depicts ELISPOT data determined from pools of peptides as detailed herein. FIG. 11B depicts specific mutation data determined from positive pools identified in FIG. 11A.

FIG. 12A depicts bioluminescence data as detailed herein. FIG. 12B depicts caliper measurement data as detailed herein.

FIG. 13A depicts tumor volume data for cohorts treated with anti-PD-1 antibody. FIG. 13B depicts tumor volume data for cohorts treated with anti-CTLA-4 antibody.

FIG. 14A depicts tumor volume data for cohorts treated as detailed herein. FIG. 14B depicts tumor volume data for cohorts treated as detailed herein.

DETAILED DESCRIPTION

Overview of Disclosure

Figure 1A:
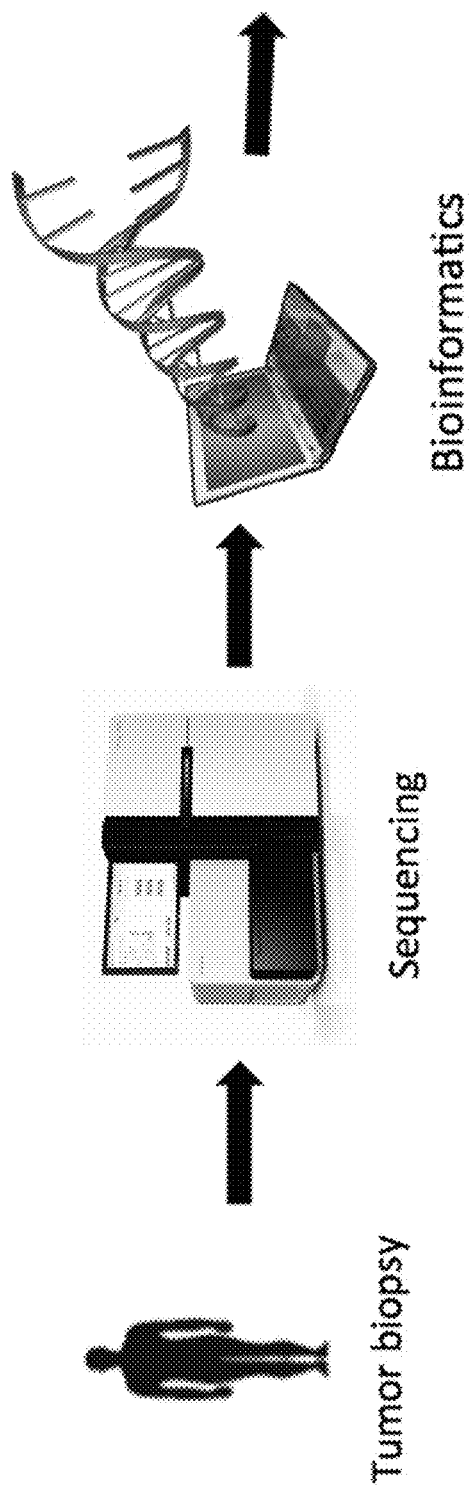
FIGS. 1A-B, 2A-B, 3A-C, and 4A-B depict a neoantigen discovery pipeline that eliminates in silico epitope binding prediction. More specifically.

Cancer immunotherapies are finally coming of age and represent a new armamentarium in the fight against cancer. These novel therapies can produce complete and enduring responses in a subset of patients with metastatic disease. While personalized cancer vaccines and cell therapies are now being translated into the clinical arena numerous challenges still remain to their widespread implementation, including limited amounts of tumor tissue for sequencing, protracted turnaround times for identifying candidate neoantigens, affordability of these platforms and low success rates of detecting immunogenic neoantigens using existing in silico prediction algorithms. The present disclosure describes a functional neoantigen identification pipeline platform, which is rapid, sensitive and amenable to high-throughput screening to identify a patient's list of immunogenic tumor-specific neoantigens (i.e., the "antigenic mutanome") that can serve as targets for next generation immunotherapies.

The functional neoantigen identification pipeline described herein successfully identifies immunogenic neoepitopes in patients with low mutational burden cancers at a frequency that far exceeds what has previously been reported. This promises to expand the number of patients for which neoantigens can be identified and targeted therapies developed. The functional neoantigen identification pipeline is rapid (~6 weeks) and requires minimal tumor tissue and blood specimens from the study patients. This has practical implications since acquisition of large amounts of tumor tissue for sequencing and peripheral blood for immunogenicity testing is not feasible for many patients with advanced cancers. In addition, the 36 percent efficiency of identifying immunogenic neoepitopes in this study demonstrates that neoantigens can be detected in cancers with low mutational burden where they have historically been difficult to detect. The functional neoantigen identification pipeline uses 20-mer peptides that must be processed and presented by endogenous APCs to detect T cells responses also adds stringency to the pipeline platform and helps to identify the most biologically relevant neoantigens as compared to in silico epitope binding prediction algorithms.

The enhanced sensitivity of this approach enables targeting of multiple neoepitopes per patient, thereby generating a more diverse and potent repertoire of anti-tumor T-cells for the patient to enhance the likelihood of a therapeutic response and to avoid resistance. Targeting multiple personal tumor epitopes with neoantigen-directed immunotherapies will undoubtedly become a mainstay of the field. Many studies in humans and murine solid tumors models support the efficacy of protective immunity targeting neoantigens specifically expressed on the surface of tumor cells. In addition, the functional neoantigen identification pipeline can be used to detect both MHC class I and class II neoantigens.

Personalized cancer vaccines and T cell therapies targeting tumor specific neoantigens can produce complete and enduring responses in patients with metastatic disease. The evolving understanding of the tumor microenvironment and interactions with the immune system will undoubtedly yield even more effective therapies in the future. Identification of the tumor-specific neoantigens is crucial to the development of target immunotherapies and offers the potential for truly personalized cancer care that avoids off-tumor toxicities. The functional neoantigen identification pipeline platform described herein offers a promising approach.

Definitions & Interpretation

A number of aspects and embodiments are described in this disclosure. Nevertheless, it will be understood that various modifications may be made without departing from the spirit and scope of the disclosure. Accordingly, the following examples are intended to illustrate but not limit the scope of disclosure described in the claims.

Further, it is to be inferred without explicit recitation and unless otherwise intended, that when the present technology relates to a polypeptide, protein, polynucleotide or antibody, an equivalent or a biologically equivalent of such is intended within the scope of the present technology.

Throughout this disclosure, various publications, patents and published patent specifications are referenced by an identifying citation. All publications, patent applications, patents, and other references mentioned herein are expressly incorporated by reference in their entirety, to the same extent as if each were incorporated by reference individually. In case of conflict, the present specification, including definitions, will control.

The entirety of each patent, patent application, publication or any other reference or document cited herein hereby is incorporated by reference. In case of conflict, the specification, including definitions, will control.

Citation of any patent, patent application, publication or any other document is not an admission that any of the foregoing is pertinent prior art, nor does it constitute any admission as to the contents or date of these publications or documents.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described herein.

All of the features disclosed herein may be combined in any combination. Each feature disclosed in the specification may be replaced by an alternative feature serving a same, equivalent, or similar purpose. Thus, unless expressly stated otherwise, disclosed features (e.g., antibodies) are an example of a genus of equivalent or similar features.

As may be used herein, all numerical values or numerical ranges include integers within such ranges and fractions of the values or the integers within ranges unless the context clearly indicates otherwise. Further, when a listing of values is described herein (e.g., about 50%, 60%, 70%, 80%, 85% or 86%) the listing includes all intermediate and fractional values thereof (e.g., 54%, 85.4%). Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As may be used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The disclosure is generally disclosed herein using affirmative language to describe the numerous embodiments and aspects. The disclosure also specifically includes embodiments in which particular subject matter is excluded, in full or in part, such as substances or materials, method steps and conditions, protocols, or procedures. For example, in certain embodiments or aspects of the disclosure, materials and/or method steps are excluded. Thus, even though the disclosure is generally not expressed herein in terms of what the disclosure does not include aspects that are not expressly excluded in the disclosure are nevertheless disclosed herein.

The technology illustratively described herein suitably can be practiced in the absence of any element(s) not specifically disclosed herein. Thus, for example, in each instance herein any of the terms "comprising," "consisting essentially of," and "consisting of" can be replaced with either of the other two terms. The terms and expressions which have been employed are used as terms of description and not of limitation and use of such terms and expressions do not exclude any equivalents of the features shown and described or segments thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. The term "substantially" as used herein refers to a value modifier meaning "at least 95%", "at least 96%", "at least 97%", "at least 98%", or "at least 99%" and may include 100%. For example, a composition that is substantially free of X, may include less than 5%, less than 4%, less than 3%, less than 2%, or less than 1% of X, and/or X may be absent or undetectable in the composition.

Thus, it should be understood that although the present technology has been specifically disclosed by representative embodiments and optional features, modification and variation of the concepts herein disclosed can be resorted to by those skilled in the art, and such modifications and variations are considered within the scope of this technology.

As used herein, the term "neoantigen" may comprise personal mutations unique to each patient, or mutations shared between one or more patients, and that may (but not necessarily) dramatically out-number mutations to onco- genes. The subset of those mutations that alter protein coding sequences (i.e., those sequences that are protein changing, which are also referred to herein as non-synonymous mutations) comprises, in some embodiments, personal, novel antigens—neoantigens—which may provide the foreign (non-self) signal needed for cancer immunotherapy. Neoantigens result from mutations occurring during tumor growth and differ from native antigens to which the immune system is tolerant. Mounting evidence suggests that immune rejection of tumors, for example that which is seen with checkpoint modulators, may be mediated by recognition of neoantigens. Neoantigens have the potential to: (1) uniquely mark a tumor (relative to non-tumor cells) for recognition and destruction by for example the immune system; and (2) avoid central and sometimes peripheral tolerance, and thus may be recognized for targeted cancer treatment.

As may be used herein, the term "animal" refers to living multi-cellular vertebrate organisms, a category that includes, for example, mammals and birds. The term "mammal" includes both human and non-human mammals, e.g., bovines, canines, felines, rat, murines, simians, equines and humans. Additional examples include adults, juveniles and infants.

The terms "subject," "host," "individual," and "patient" may be used interchangeably herein to refer to animals, typically mammalian animals. Any suitable mammal can be treated by a method, cell or composition described herein. A mammal is a human. A mammal may be any age or at any stage of development (e.g., an adult, teen, child, infant, or a mammal in utero). A mammal may be male or female. A mammal may be a pregnant female. In some embodiments a subject may be a human. In some embodiments, a subject may have, has, may be suspected, or is suspected of having a cancer or neoplastic disorder.

As may be used herein "a population of cells" means a collection of more than one cell that is identical (clonal) or non-identical in phenotype and/or genotype.

As may be used herein, "substantially homogeneous" population of cells is a population having at least 70%, or alternatively at least 75%, or alternatively at least 80%, or alternatively at least 85%, or alternatively at least 90%, or alternatively at least 95%, or alternatively at least 98% identical phenotype, as measured by pre-selected markers, phenotypic or genomic traits. In one aspect, the population is a clonal population.

As may be used herein, "heterogeneous" population of cells is a population having up to 69%, or alternatively up to 60%, or alternatively up to 50%, or alternatively up to 40%, or alternatively up to 30%, or alternatively up to 20%, or alternatively up to 10%, or alternatively up to 5%, or alternatively up to 4%, or alternatively up to 3%, or alternatively up to 2%, or alternatively up to 61%, or alternatively up to 0.5% identical phenotype, as measured by pre-selected markers, phenotypic or genomic traits.

A "composition" typically indicates a combination of the active agent, e.g., an engineered immune cell, e.g., T-cell, a modified T-cell, a NK cell, a chimeric antigen cell, a cell comprising an engineered immune cell, e.g., a T-cell, a NK cell, a CAR T cell or a CAR NK cell, an antibody, a cytokine, IL-12, a compound or composition, and a naturally-occurring or non-naturally-occurring carrier, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid components, which can also function in a buffering capacity, include alanine, arginine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this technology, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The compositions used in accordance with the disclosure, including cells, treatments, therapies, agents, drugs and pharmaceutical formulations can be packaged in dosage unit form for ease of administration and uniformity of dosage. The term "unit dose" or "dosage" refers to physically discrete units suitable for use in a subject, each unit containing a predetermined quantity of the composition calculated to produce the desired responses in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described herein.

As may be used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "encode" as it is applied to nucleic acid sequences refers to a polynucleotide which is said to "encode" a polypeptide if, in its native state or when manipulated by methods well known to those skilled in the art, can be transcribed and/or translated to produce the mRNA for the polypeptide and/or a fragment thereof. The antisense strand is the complement of such a nucleic acid, and the encoding sequence can be deduced therefrom.

As may be used herein, the term "isolated cell" generally refers to a cell that is substantially separated from other cells of a tissue. The term includes prokaryotic and eukaryotic cells.

"Immune cells" includes, e.g., white blood cells (leukocytes) which are derived from hematopoietic stem cells (HSC) produced in the bone marrow, lymphocytes (T cells, B cells, natural killer (NK) cells) and myeloid-derived cells (neutrophil, eosinophil, basophil, monocyte, macrophage, dendritic cells). A "T cell" includes all types of immune cells expressing CD3 including T-helper cells (CD4+ cells), cytotoxic T-cells (CD8+ cells), natural killer T-cells, T-regulatory cells (Treg) and gamma-delta T cells. A "cytotoxic cell" includes CD8+ T cells, natural-killer (NK) cells, and neutrophils, which cells are capable of mediating cytotoxicity responses. Cytokines are small secreted proteins released by immune cells that have a specific effect on the interactions and communications between said immune cells. Cytokines can be pro-inflammatory or anti-inflammatory. A non-limiting example of a cytokine is granulocyte-macrophage colony-stimulating factor (GM-CSF), which stimulates stem cells to produce granulocytes (neutrophils, eosinophils, and basophils) and monocytes.

As used herein, the phrase "immune response" or its equivalent "immunological response" refers to the development of a cell-mediated response (e.g. mediated by antigen-specific T cells or their secretion products). A cellular immune response is elicited by the presentation of polypeptide epitopes in association with Class I or Class II MHC molecules, to treat or prevent a viral infection, expand antigen-specific B-reg cells, TC1, CD4+ T helper cells and/or CD8+ cytotoxic T cells and/or disease generated, autoregulatory T cell and B cell "memory" cells. The response may also involve activation of other components. In some aspect, the term "immune response" may be used to encompass the formation of a regulatory network of immune cells. Thus, the term "regulatory network formation" may refer to an immune response elicited such that an immune cell, preferably a T cell, more preferably a T regulatory cell, triggers further differentiation of other immune cells, such as but not limited to, B cells or antigen-presenting cells—non-limiting examples of which include dendritic cells, monocytes, and macrophages. In certain embodiments, regulatory network formation involves B cells being differentiated into regulatory B cells; in certain embodiments, regulatory network formation involves the formation of tolerogenic antigen-presenting cells.

The term "transduce" or "transduction" as it is applied to the production of chimeric antigen receptor cells refers to the process whereby a foreign nucleotide sequence is introduced into a cell. Transduction may be via a vector.

As may be used herein, the term "vector" refers to a nucleic acid construct deigned for transfer between different hosts, including but not limited to a plasmid, a virus, a cosmid, a phage, a BAC, a YAC, etc. A "viral vector" is defined as a recombinantly produced virus or viral particle that comprises a polynucleotide to be delivered into a host cell, either in vivo, ex vivo or in vitro. Plasmid vectors may be prepared from commercially available vectors. In other embodiments, viral vectors may be produced from baculoviruses, retroviruses, adenoviruses, AAVs, etc. according to techniques known in the art. In one embodiment, the viral vector is a lentiviral vector. Examples of viral vectors include retroviral vectors, adenovirus vectors, adeno-associated virus vectors, alphavirus vectors and the like. Infectious tobacco mosaic virus (TMV)-based vectors can be used to manufacturer proteins. Alphavirus vectors, such as Semliki Forest virus-based vectors and Sindbis virus-based vectors, have also been developed for use in gene therapy and immunotherapy. Vectors that contain both a promoter and a cloning site into which a polynucleotide can be operatively linked are well known in the art. Such vectors are capable of transcribing RNA in vitro or in vivo and are commercially available from sources such as Agilent Technologies (Santa Clara, Calif.) and Promega Biotech (Madison, Wis.).

An "an effective amount" or "efficacious amount" is an amount sufficient to achieve the intended purpose, non-limiting examples of such include: initiation of the immune response, modulation of the immune response, suppression of an inflammatory response and modulation of T cell activity or T cell populations. In one aspect, the effective amount is one that functions to achieve a stated therapeutic purpose, e.g., a therapeutically effective amount. As described herein in detail, the effective amount, or dosage, depends on the purpose and the composition, and can be determined according to the present disclosure.

As may be used herein, the term "receptor" or "T-cell receptor" or "TCR" refers to a cell surface molecule found on T-cells that functions to recognize and bind antigens presented by antigen presenting molecules. Generally, a TCR is a heterodimer of an alpha chain (TRA) and a beta chain (TRB). Some TCRs are comprised of alternative gamma (TRG) and delta (TRD) chains. T-cells expressing this version of a TCR are known as γδ T-cells. TCRs are part of the immunoglobulin superfamily. Accordingly, like an antibody, the TCR comprises three hypervariable CDR regions per chain. There is also an additional area of hypervariability on the beta-chain (HV4). The TCR heterodimer is generally present in an octomeric complex that further comprises three dimeric signaling modules CD3γ/ε, CD3δ/ε, and CD247 ζ/ζ (or ζ/η.

As may be used herein, the term "engineered T-cell receptor" refers to a molecule comprising the elements of (a) an extracellular antigen binding domain, (b) a transmembrane domain, and (c) an intracellular signaling domain. In some aspects, an engineered T-cell receptor is a genetically modified TCR, a modified TCR, a recombinant TCR, a transgenic TCR, a partial TCR, a chimeric fusion protein, a CAR, a first generation CAR, a second generation CAR, a third generation CAR, or a fourth generation TRUCK. In some aspects, the engineered T-cell receptor comprises an antibody or a fragment of an antibody. In particular aspects, the engineered T-cell receptor is a genetically modified TCR or a CAR.

The term "modified TCR", as may be used herein, refers to a TCR that has been genetically engineered, and/or a transgenic TCR, and/or a recombinant TCR. Non-limiting examples of modified TCRs include single-chain VaVP TCRs (scTv), full-length TCRs produced through use of a T cell display system, and TCRs wherein the CDR regions have been engineered to recognize a specific antigen, peptide, fragment, and/or MHC molecule.

As may be used herein, the term "antibody" ("Ab") collectively refers to immunoglobulins (or "Ig") or immunoglobulin-like molecules including but not limited to antibodies of the following isotypes: IgM, IgA, IgD, IgE, IgG, and combinations thereof. Immunoglobulin-like molecules include but are not limited to similar molecules produced during an immune response in a vertebrate, for example, in mammals such as humans, rats, goats, rabbits and mice. Unless specifically noted otherwise, the term "antibody" includes intact immunoglobulins and "antibody fragments" or "antigen binding fragments" that specifically bind to a molecule of interest (or a group of highly similar molecules of interest) to the substantial exclusion of binding to other molecules (for example, antibodies and antibody fragments that have a binding constant for the molecule of interest that is at least $10^3$ M$^{-1}$ greater, at least $10^4$ M$^{-1}$ greater or at least $10^5$ M$^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also *Pierce Catalog and Handbook,* 1994-1995 (Pierce Chemical Co., Rockford, Ill.); Kuby, Immunology, 3$^{rd}$Ed., W. H. Freeman & Co., New York, 1997.

As may be used herein, the term "monoclonal antibody" refers to an antibody produced by a cell into which the light and heavy chain genes of a single antibody have been transfected or, more traditionally, by a single clone of B-lymphocytes. Monoclonal antibodies generally have affinity for a single epitope (i.e. they are monovalent) but may be engineered to be specific for two or more epitopes (e.g. bispecific). Methods of producing monoclonal antibodies are known to those of skill in the art, for example by creating a hybridoma through fusion of myeloma cells with immune spleen cells, phage display, single cell amplification from B-cell populations, single plasma cell interrogation technologies, and single B-cell culture. Monoclonal antibodies include recombinant antibodies, chimeric antibodies, humanized antibodies, and human antibodies.

The general structure of an antibody is comprised of heavy (H) chains and light (L) chains connected by disulfide bonds. The structure can also comprise glycans attached at conserved amino acid residues. Each heavy and light chain contains a constant region and a variable region (also known as "domains"). There are two types of light chain, lambda (λ) and kappa (κ). There are five primary types of heavy chains which determine the isotype (or class) of an antibody molecule: gamma (γ), delta (δ), alpha (α), mu (μ) and epsilon (ε). The constant regions of the heavy chain also contribute to the effector function of the antibody molecule. Antibodies comprising the heavy chains, μ, δ, γ3, γ1, α1, γ2, γ4, ε, and α2 result in the following isotypes: IgM, IgD, IgG3, IgG1, IgA1, IgG2, IgG4, IgE, and IgA2, respectively. An IgY isotype, related to mammalian IgG, is found in reptiles and birds. An IgW isotype, related to mammalian IgD, is found in cartilaginous fish. Class switching is the process by which the constant region of an immunoglobulin heavy chain is replaced with a different immunoglobulin heavy chain through recombination of the heavy chain locus of a B-cell to produce an antibody of a different isotype. Antibodies may exist as monomers (e.g. IgG), dimers (e.g. IgA), tetramers (e.g. fish IgM), pentamers (e.g. mammalian IgM), and/or in complexes with other molecules. Antibodies may be bound to the surface of a cell or secreted by a cell.

The variable regions of the immunoglobulin heavy and the light chains specifically bind the antigen. The "framework" region is a portion of the Fab that acts as a scaffold for three hypervariable regions called "complementarity-determining regions" (CDRs). A set of CDRs is known as a paratope. The framework regions of different light or heavy chains are relatively conserved within a species. The combined framework region of an antibody (comprising regions from both light and heavy chains), largely adopts a β-sheet conformation and the CDRs form loops which connect, and in some cases form part of, the β-sheet structure. Thus, framework regions act to position the CDRs in correct orientation by inter-chain, non-covalent interactions. The framework region and CDRs for numerous antibodies have been defined and are available in a database maintained online (Kabat et al., *Sequences of Proteins of Immunological Interest*, U.S. Department of Health and Human Services, 1991).

The CDRs of the variable regions of heavy and light chains (VH and VL) are responsible for binding to an epitope of an antigen. A limited number of amino acid positions within the CDRs are directly involved in antigen binding. These positions within the CDRs are called specificity determining residues (SDRs). The CDRs of a heavy or light chain are numbered sequentially starting from the N-terminal end (i.e. CDR1, CDR2, and CDR3). For example, a VL CDR3 is the middle CDR located in the variable domain of the light chain of an antibody. A VH CDR1 is the first CDR in the variable domain of a heavy chain of an antibody. An antibody that binds a specific antigen will have specific VH and VL region sequences, and thus specific CDR sequences. Antibodies with different specificities (i.e. different combining sites for different antigens) have different CDRs.

The term "humanized" when used in reference to an antibody, means that the amino acid sequence of the antibody has non-human amino acid residues (e.g., mouse, rat, goat, rabbit, etc.) of one or more complementarity determining regions (CDRs) that specifically bind to the desired antigen in an acceptor human immunoglobulin molecule, and one or more human amino acid residues in the Fv framework region (FR), which are amino acid residues that flank the CDRs. Such antibodies typically have reduced immunogenicity and therefore a longer half-life in humans as compared to the non-human parent antibody from which one or more CDRs were obtained or are based upon.

An "antigen-binding fragment" (Fab) refers to the regions of an antibody corresponding to two of the three fragments produced by papain digestion. The Fab fragment comprises the region that binds to an antigen and is composed of one variable region and one constant region from both a heavy chain and a light chain. An F(ab')2 fragment refers to a fragment of an antibody digested by pepsin or the enzyme IdeS (immunoglobulin degrading enzyme from *S. pyogenes*) comprising two Fab regions connected by disulfide bonds. A single chain variable fragment ("scFv") refers to a fusion protein comprising at least one VH and at least one VL region connected by a linker of between 5 to 30 amino acids. Methods and techniques of developing scFv that bind to specific antigens are known in the art (see, e.g. Ahmad, Z. A. et al., *Clinical and Developmental Immunology*, 2012: 980250 (2012)).

As may be used herein, the term "antigen" refers to a compound, composition, or substance that may be specifically bound and/or recognized by the products of specific humoral or cellular immunity and antigen recognition molecules, including but not limited to an antibody molecule, single-chain variable fragment (scFv), cell surface immunoglobulin receptor, B-cell receptor (BCR), T-cell receptor (TCR), engineered TCR, modified TCR, or CAR. The term "epitope" refers to an antigen or a fragment, region, site, or domain of an antigen that is recognized by an antigen recognition molecule. Antigens can be any type of molecule including but not limited to peptides, proteins, lipids, phospholipids haptens, simple intermediary metabolites, sugars (e.g., monosaccharides or oligosaccharides), hormones, and macromolecules such as complex carbo-hydrates (e.g., polysaccharides). Some non-limiting examples of antigens include antigens involved in autoimmune disease (including autoantigens), allergy, and graft rejection, tumor antigens, toxins, and other miscellaneous antigens. Non-limiting examples of tumor antigens include mesothelin, ROR1 and EGFRvIII, ephrin type-A receptor 2 (EphA2), interleukin (IL)-13r alpha 2, an EGFR VIII, a PSMA, an EpCAM, a GD3, a fucosyl GM1, a PSCA, a PLAC1, a sarcoma breakpoint, a Wilms Tumor 1, a hematologic differentiation antigen, a surface glycoprotein, a gangliosides (GM2), a growth factor receptor, a stromal antigen, a vascular antigen, or a combination thereof. Antigens expressed by pathogens include, but are not limited to, microbial antigens such as viral antigens, bacterial antigens, fungal antigens, protozoa, and other parasitic antigens.

As may be used herein, the term "target cell population" refers to a population of cells that present antigens, which can be targeted by engineered T cells. Non-limiting examples of target cell populations include tumor cells, cancer cells and pathogen infected cells. Non-limiting examples of pathogens include viral and bacterial pathogens.

As may be used herein, the term "antigen binding domain" refers to any protein or polypeptide domain that can specifically bind to an antigen target, such as a neoantigen, (including target complexes of antigens and MHC molecules).

As may be used herein, the term "autologous," in reference to cells, tissue, and/or grafts refers to cells, tissue, and/or grafts that are isolated from and then and administered back into the same subject, patient, recipient, and/or host. "Allogeneic" refers to non-autologous cells, tissue, and/or grafts.

As may be used herein, the term "B cell," refers to a type of lymphocyte in the humoral immunity of the adaptive immune system. B cells principally function to make antibodies, serve as antigen presenting cells, release cytokines, and develop memory B cells after activation by antigen interaction. B cells are distinguished from other lymphocytes, such as T cells, by the presence of a B-cell receptor on the cell surface. B cells may either be isolated or obtained from a commercially available source.

As may be used herein, the term "major histocompatibility complex" (MHC) refers to an antigen presentation molecule that functions as part of the immune system to bind antigens and other peptide fragments and display them on the cell surface for recognition by antigen recognition molecules such as TCR. MHC may be used interchangeably with the term "human leukocyte antigen" (HLA) when used in reference to human MHC; thus, MHC refers to all HLA subtypes including, but not limited to, the classical MHC genes disclosed herein: HLA-A, HLA-B, HLA-C, HLA-E, HLA-F, HLA-G, HLA-DM, HLA-DO, HLA-DP, HLA-DQ, and HLA-DR, in addition to all variants, isoforms, isotypes, and other biological equivalents thereof. MHC class I (MHC-I) and MHC class II (MHC-II) molecules utilize distinct antigen processing pathways. In general, peptides derived from intracellular antigens are presented to CD8+ T cells by MHC class I molecules, which are expressed on virtually all cells, while extracellular antigen-derived peptides are presented to CD4+ T cells by MHC-II molecules. However, several exceptions to this dichotomy have been observed. In certain embodiments disclosed herein, a particular antigen, peptide, and/or epitope is identified and presented in an antigen-MHC complex in the context of an appropriate MHC class I or II protein. The genetic makeup of a subject may be assessed to determine which MHC allele is suitable for a particular patient, disease, or condition with a particular set of antigens. In mice, the MHC genes are known as the histocompatibility 2 (H-2) genes. Murine classical MHC class I subtypes include H-2D, H-2K, and H-2 µL. Murine non-classical MHC class I subtypes include H-2Q, H-2M, and H-2T. Murine classical MHC class II subtypes include H-2A (I-A), and H-2E (1-E). Non-classical murine MHC class II subtypes include H-2M and H-20.

Canine MHC molecules are known as Dog Leukocyte Antigens (DLA). Feline MHC molecules are known as Feline Leukocyte Antigens (FLA). An orthologous or homologous MHC molecule may be selected to transition a therapy or treatment involving a specific antigen-MHC complex from one species to a different species.

As may be used herein, a "target cell" is any cell that expresses a neoantigen target to which the engineered T cells can bind.

As used herein, a "cancer" is a disease state characterized by the presence in a subject of cells demonstrating abnormal uncontrolled replication and may be used interchangeably with the term "tumor." The cancer may be, e.g., a leukemia or a lymphoma, pancreatic neuroendocrine carcinoma head and neck squamous cells carcinoma, and pancreatic adenocarcinoma. "Cell associated with the cancer" may refer to those subject cells that demonstrate abnormal uncontrolled replication. The cancer may be acute myeloid leukemia or acute lymphoblastic leukemia, pancreatic neuroendocrine carcinoma head and neck squamous cells carcinoma, and pancreatic adenocarcinoma. As used herein a "leukemia" is a cancer of the blood or bone marrow characterized by an abnormal increase of immature white blood cells. The specific condition of acute myeloid leukemia (AML)—also referred to as acute myelogenous leukemia or acute myeloblastic leukemia—is a cancer of the myeloid origin blood cells, characterized by the rapid growth of abnormal myeloid cells that accumulate in the bone marrow and interfere with the production of normal blood cells. The specific condition of acute lymphoblastic leukemia (ALL)—also referred to as acute lymphocytic leukemia or acute lymphoid leukemia—is a cancer of the white blood cells, characterized by the overproduction and accumulation of malignant, immature leukocytes (lymphoblasts) resulting a lack of normal, healthy blood cells. As used herein a "lymphoma" is a cancer of the blood characterized by the development of blood cell tumors and symptoms of enlarged lymph nodes, fever, drenching sweats, unintended weight loss, itching, and constantly feeling tired.

A "solid tumor" is an abnormal mass of tissue that usually does not contain cysts or liquid areas. Solid tumors can be benign or malignant. Different types of solid tumors are named for the type of cells that form them. Examples of solid tumors include sarcomas, carcinomas, and lymphomas.

The term "B-cell lymphoma or leukemia" refers to a type of cancer that forms in issues of the lymphatic system or bone marrow and has undergone a malignant transformation that makes the cells within the cancer pathological to the host organism with the ability to invade or spread to other parts of the body.

One of skill in the art can monitor expression of the transcription factors using methods such as RNA-sequencing, DNA microarrays, Real-time PCR, or Chromatin immunoprecipitation (ChIP) etc. Protein expression can be monitored using methods such as flow cytometry, Western blotting, 2-D gel electrophoresis or immunoassays etc.

As may be used herein, the term "detectable marker" refers to at least one marker capable of directly or indirectly, producing a detectable signal. A non-exhaustive list of this marker includes enzymes which produce a detectable signal, for example by colorimetry, fluorescence, luminescence, such as horseradish peroxidase, alkaline phosphatase, 0-galactosidase, glucose-6-phosphate dehydrogenase, chromophores such as fluorescent, luminescent dyes, groups with electron density detected by electron microscopy or by their electrical property such as conductivity, amperometry, voltammetry, impedance, detectable groups, for example whose molecules are of sufficient size to induce detectable modifications in their physical and/or chemical properties, such detection may be accomplished by optical methods such as diffraction, surface plasmon resonance, surface variation, the contact angle change or physical methods such as atomic force spectroscopy, tunnel effect, or radioactive molecules such as 32 P, 35 S or 125 I.

As may be used herein, the term "purification marker" or "reporter protein" refer to at least one marker useful for purification or identification. A non-exhaustive list of this marker includes His, lacZ, GST, maltose-binding protein, NusA, BCCP, c-myc, CaM, FLAG, GFP, YFP, cherry, thioredoxin, poly(NANP), V5, Snap, HA, chitin-binding protein, Softag 1, Softag 3, Strep, or S-protein. Suitable direct or indirect fluorescence marker comprise FLAG, GFP, YFP, RFP, dTomato, cherry, Cy3, Cy 5, Cy 5.5, Cy 7, DNP, AMCA, Biotin, Digoxigenin, Tamra, Texas Red, rhodamine, Alexa fluors, FITC, TRITC or any other fluorescent dye or hapten.

As may be used herein, "homology" or "identical", percent "identity" or "similarity", when used in the context of two or more nucleic acids or polypeptide sequences, refers to two or more sequences or subsequences that are the same or have a specified percentage of nucleotides or amino acid residues that are the same, e.g., at least 60% identity, preferably at least 65%, 70%, 75%, 80%, 85%, 90%, 91%, 92%, 93%, 94%, 95%, 96%, 97%, 98%, 99%, or higher identity over a specified region (e.g., nucleotide sequence encoding the chimeric PVX described herein). Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. The terms "homology" or "identical," percent "identity" or "similarity" also refer to, or can be applied to, the complement of a test sequence. The terms also include sequences that have deletions and/or additions, as well as those that have substitutions. As described herein, the preferred algorithms can account for gaps and the like. Preferably, identity exists over a region that is at least about 25 amino acids or nucleotides in length, or more preferably over a region that is at least 50-100 amino acids or nucleotides in length. An "unrelated" or "non-homologous" sequence shares less than 40% identity, or alternatively less than 25% identity, with one of the sequences disclosed herein.

It is to be inferred without explicit recitation and unless otherwise intended, that when the present disclosure relates to a polypeptide, protein, polynucleotide, an equivalent or a biologically equivalent of such is intended within the scope of this disclosure. As used herein, the term "biological equivalent thereof" is intended to be synonymous with "equivalent thereof" when referring to a reference protein, polypeptide or nucleic acid, intends those having minimal homology while still maintaining desired structure or functionality. Unless specifically recited herein, it is contemplated that any of the above also includes equivalents thereof. For example, an equivalent intends at least about 70% homology or identity, or at least 80% homology or identity and alternatively, or at least about 85%, or alternatively at least about 90%, or alternatively at least about 95%, or alternatively at least 98% percent homology or identity and/or exhibits substantially equivalent biological activity to the reference protein, polypeptide, or nucleic acid. Alternatively, when referring to polynucleotides, an equivalent thereof is a polynucleotide that hybridizes under stringent conditions to the reference polynucleotide or its complement.

The phrase "equivalent polypeptide" or "equivalent peptide fragment" refers to protein, polynucleotide, or peptide fragment encoded by a polynucleotide that hybridizes to a polynucleotide encoding the exemplified polypeptide or its complement of the polynucleotide encoding the exemplified polypeptide, under high stringency and/or which exhibit similar biological activity in vivo, e.g., approximately 100%, or alternatively, over 90% or alternatively over 85% or alternatively over 70%, as compared to the standard or control biological activity. Additional embodiments within the scope of this disclosure are identified by having more than 60%, or alternatively, more than 65%, or alternatively, more than 70%, or alternatively, more than 75%, or alternatively, more than 80%, or alternatively, more than 85%, or alternatively, more than 90%, or alternatively, more than 95%, or alternatively more than 97%, or alternatively, more than 98% or 99% sequence homology. Percentage homology can be determined by sequence comparison using programs such as BLAST run under appropriate conditions. In one aspect, the program is run under default parameters.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

As may be used herein, the term "hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

The term "isolated" as may be used herein refers to molecules or biologicals or cellular materials being substantially free from other materials. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. The term "isolated" is also used herein to refer to cells or tissues that are isolated from other cells or tissues and is meant to encompass both cultured and engineered cells or tissues.

The term "protein", "peptide" and "polypeptide" are used interchangeably and in their broadest sense to refer to a compound of two or more subunit amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The terms "polynucleotide" and "oligonucleotide" are used interchangeably and refer to a polymeric form of nucleotides of any length, either deoxyribonucleotides or ribonucleotides or analogs thereof. Polynucleotides can have any three dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double and single stranded molecules. Unless otherwise specified or required, any aspect of this technology that is a polynucleotide encompasses both the double stranded form and each of two complementary single stranded forms known or predicted to make up the double stranded form.

As may be used herein, the term "purified" does not require absolute purity; rather, it is intended as a relative term. Thus, for example, a purified nucleic acid, peptide, protein, biological complexes or other active compound is one that is isolated in whole or in part from proteins or other contaminants. Generally, substantially purified peptides, proteins, biological complexes, or other active compounds for use within the disclosure comprise more than 80% of all macromolecular species present in a preparation prior to admixture or formulation of the peptide, protein, biological complex or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, biological complex or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

As may be used herein, the term "recombinant," when used to modify "protein," "peptide," or "polypeptide," or any specific protein, peptide, or polypeptide, refers to a protein, peptide, or polypeptide produced by recombinant DNA techniques, wherein generally, DNA encoding the polypeptide is inserted into a suitable expression vector, which is in turn used to transform a host cell to produce the heterologous protein.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. When the disease is cancer, the following clinical end points are non-limiting examples of treatment: reduction in tumor burden, slowing of tumor growth, longer overall survival, longer time to tumor progression, inhibition of metastasis or a reduction in metastasis of the tumor. In one aspect, treatment excludes prophylaxis.

As used herein, "anti-tumor immunity" in a subject refers to reducing or preventing the symptoms or cancer from occurring in a subject that is predisposed or does not yet display symptoms of the cancer.

A subject may be in need of a treatment, cell or composition described herein. A subject may have or be suspected of having a neoplastic disorder, neoplasia, tumor, malignancy or cancer. In some embodiments a subject in need of a treatment, cell or composition described herein has or is suspected of having a neoplastic disorder, neoplasia, tumor, malignancy or cancer. An engineered T cell described herein may be used to treat a subject having, or suspected of having, a neoplastic disorder, neoplasia, tumor, malignancy or cancer.

Presented herein is a method of treating a subject having or suspected of having, a neoplasia, neoplastic disorder, tumor, cancer, or malignancy. A method of treating a subject may comprise administering a therapeutically effective amount of an engineered T cell to a subject. The method may comprise reducing or inhibiting proliferation of a neoplastic cell, tumor, cancer or malignant cell, comprising contacting the cell, tumor, cancer or malignant cell, with the engineered T cell in an amount sufficient to reduce or inhibit proliferation of the neoplastic cell, tumor, cancer or malignant cell.

A method of reducing or inhibiting metastasis of a neoplasia, tumor, cancer or malignancy to other sites, or formation or establishment of metastatic neoplasia, tumor, cancer or malignancy at other sites distal from a primary neoplasia, tumor, cancer or malignancy, may comprise administering to a subject an amount of an engineered T cell sufficient to reduce or inhibit metastasis of the neoplasia, tumor, cancer or malignancy to other sites, or formation or establishment of metastatic neoplasia, tumor, cancer or malignancy at other sites distal from the primary neoplasia, tumor, cancer or malignancy.

Non-limiting examples of a neoplasia, neoplastic disorder, tumor, cancer or malignancy include a carcinoma, sarcoma, neuroblastoma, cervical cancer, hepatocellular cancer, mesothelioma, glioblastoma, myeloma, lymphoma, leukemia, adenoma, adenocarcinoma, glioma, glioblastoma, retinoblastoma, astrocytoma, oligodendrocytoma, meningioma, or melanoma. A neoplasia, neoplastic disorder, tumor, cancer or malignancy may comprise or involve hematopoietic cells. Non-limiting examples of a sarcoma include a lymphosarcoma, liposarcoma, osteosarcoma, chondrosarcoma, leiomyosarcoma, rhabdomyosarcoma or fibrosarcoma. A neoplasia, neoplastic disorder, tumor, cancer or malignancy may be a myeloma, lymphoma or leukemia. A neoplasia, neoplastic disorder, tumor, cancer or malignancy may comprise a lung, thyroid, head or neck, nasopharynx, throat, nose or sinuses, brain, spine, breast, adrenal gland, pituitary gland, thyroid, lymph, gastrointestinal (mouth, esophagus, stomach, duodenum, ileum, jejunum (small intestine), colon, rectum), genito-urinary tract (uterus, ovary, cervix, endometrial, bladder, testicle, penis, prostate), kidney, pancreas, liver, bone, bone marrow, lymph, blood, muscle, or skin neoplasia, tumor, or cancer. A neoplasia, neoplastic disorder, tumor, cancer or malignancy may comprise a small cell lung or non-small cell lung cancer. A neoplasia, neoplastic disorder, tumor, cancer or malignancy may comprise a stem cell neoplasia, tumor, cancer or malignancy.

A treatment method may inhibit, or reduce relapse or progression of the neoplasia, neoplastic disorder, tumor, cancer or malignancy. A treatment method may comprise administering an anti-cell proliferative, anti-neoplastic, anti-tumor, anti-cancer or immune-enhancing treatment or therapy. A method of treatment may result in partial or complete destruction of the neoplastic, tumor, cancer or malignant cell mass; a reduction in volume, size or numbers of cells of the neoplastic, tumor, cancer or malignant cell mass; stimulating, inducing or increasing neoplastic, tumor, cancer or malignant cell necrosis, lysis or apoptosis; reducing neoplasia, tumor, cancer or malignancy cell mass; inhibiting or preventing progression or an increase in neoplasia, tumor, cancer or malignancy volume, mass, size or cell numbers; or prolonging lifespan. A method of treatment may result in reducing or decreasing severity, duration or frequency of an adverse symptom or complication associated with or caused by the neoplasia, tumor, cancer or malignancy. A method of treatment may result in reducing or decreasing pain, discomfort, nausea, weakness or lethargy. A method of treatment may result in increased energy, appetite, improved mobility or psychological well-being.

As may be used herein, the term "administer" and "administering" are used to mean introducing the therapeutic agent (e.g. polynucleotide, vector, cell, modified cell, population) into a subject. The therapeutic administration of this substance serves to attenuate any symptom, or prevent additional symptoms from arising. When administration is for the purposes of preventing or reducing the likelihood of developing an autoimmune disease or disorder, the substance is provided in advance of any visible or detectable symptom. Routes of administration include, but are not limited to, oral (such as a tablet, capsule or suspension), topical, transdermal, intranasal, vaginal, rectal, subcutaneous intravenous, intraarterial, intramuscular, intraosseous, intraperitoneal, epidural and intrathecal.

As may be used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample. In one aspect, the expression level of a gene from one sample may be directly compared to the expression level of that gene from a control or reference sample. In another aspect, the expression level of a gene from one sample may be directly compared to the expression level of that gene from the same sample following administration of a compound.

As may be used herein, the term "contacting" means direct or indirect binding or interaction between two or more. A particular example of direct interaction is binding. A particular example of an indirect interaction is where one entity acts upon an intermediary molecule, which in turn acts upon the second referenced entity. Contacting as used herein includes in solution, in solid phase, in vitro, ex vivo, in a cell and in vivo. Contacting in vivo can be referred to as administering, or administration.

As may be used herein, the term "binds" or "antibody binding" or "specific binding" means the contact between the antigen binding domain of an antibody, antibody fragment, CAR, TCR, engineered TCR, BCR, MHC, immunoglobulin-like molecule, scFv, CDR or other antigen presentation molecule and an antigen, epitope, or peptide with a binding affinity (KD) of less than $10^{-5}$ M. In some aspects, an antigen binding domain binds to both a complex of both an antigen and an MHC molecule. In some aspects, antigen binding domains bind with affinities of less than about $10^{-6}$ M, $10^{-7}$ M, and preferably $10^{-8}$ M, $10^{-9}$ M, $10^{-10}$ M, $10^{-11}$ M, or $10^{-12}$ M. In a particular aspect, specific binding refers to the binding of an antigen to an MHC molecule, or the binding of an antigen binding domain of an engineered T-cell receptor to an antigen or antigen-MHC complex.

As may be used herein, the term "introduce" as applied to methods of producing modified cells such as chimeric antigen receptor cells refers to the process whereby a foreign (i.e. extrinsic or extracellular) agent is introduced into a host cell thereby producing a cell comprising the foreign agent. Methods of introducing nucleic acids include but are not limited to transduction, retroviral gene transfer, transfection, electroporation, transformation, viral infection, and other recombinant DNA techniques known in the art. Transduction may be done via a vector (e.g., a viral vector). Transfection may be done via a chemical carrier, DNA/liposome complex, or micelle (e.g., Lipofectamine (Invitrogen)). Viral infection may be done via infecting the cells with a viral particle comprising the polynucleotide of interest (e.g., AAV). Introduction may comprise CRISPR mediated gene editing or Transcription activator-like effector nuclease (TALEN) mediated gene editing. Methods of introducing non-nucleic acid foreign agents (e.g., soluble factors, cytokines, proteins, peptides, enzymes, growth factors, signaling molecules, small molecule inhibitors) include but are not limited to culturing the cells in the presence of the foreign agent, contacting the cells with the agent, contacting the cells with a composition comprising the agent and an excipient, and contacting the cells with vesicles or viral particles comprising the agent.

In the context of a nucleic acid or amino acid sequence, the term "chimeric" intends that the sequence contains is comprised of at least one substituent unit (e.g., fragment, region, portion, domain, polynucleotide, or polypeptide) that is derived from, obtained or isolated from, or based upon other distinct physical or chemical entities. For example, a chimera of two or more different proteins may comprise the sequence of a variable region domain from an antibody fused to the transmembrane domain of a cell signaling molecule. In some aspects, a chimera intends that the sequence is comprised of sequences from at least two distinct species.

The term "chimeric antigen receptor" (CAR), as used herein, refers to a fused protein comprising an extracellular domain capable of binding to an antigen, a transmembrane domain derived from a polypeptide different from a polypeptide from which the extracellular domain is derived, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" or "intracellular signaling domain" means any oligopeptide or polypeptide known to function as a domain that transmits a signal to cause activation or inhibition of a biological process in a cell. In certain embodiments, the intracellular domain may comprise, alternatively consist essentially of, or yet further comprise one or more costimulatory signaling domains in addition to the primary signaling domain. The "transmembrane domain" means any oligopeptide or polypeptide known to span the cell membrane and that can function to link the extracellular and signaling domains. A chimeric antigen receptor may optionally comprise a "hinge domain" which serves as a linker between the extracellular and transmembrane domains. Non-limiting exemplary polynucleotide sequences that encode for components of each domain are disclosed herein, e.g.:

Hinge domain: IgG1 heavy chain hinge polynucleotide sequence:

```
                                            (SEQ ID NO: 1)
CTCGAGCCCAAATCTTGTGACAAAACTCACACATGCCCACCGTGCCCG,
``` and optionally an equivalent thereof.

Transmembrane domain: CD28 transmembrane region polynucleotide sequence:

```
                                            (SEQ ID NO: 2)
TTTTGGGTGCTGGTGGTGGTTGGTGGAGTCCTGGCTTGCTATAGCTTGC
TAGTAACAGTGGCCTTTATTATTTTCTGGGTG,
``` and optionally an equivalent thereof.

Intracellular domain: 4-1BB co-stimulatory signaling region polynucleotide sequence:

(SEQ ID NO: 3)
AAACGGGGCAGAAAGAAACTCCTGTATATATTCAAACAACCATTTATGA

GACCAGTACAAACTACTCAAGAGGAAGATGGCTGTAGCTGCCGATTTCC

AGAAGAAGAAGAAGGAGGATGTGAACTG, and optionally an equivalent thereof.

Intracellular domain: CD28 co-stimulatory signaling region polynucleotide sequence:

(SEQ ID NO: 4)
AGGAGTAAGAGGAGCAGGCTCCTGCACAGTGACTACATGAACATGACTC

CCCGCCGCCCCGGGCCCACCCGCAAGCATTACCAGCCCTATGCCCCACC

ACGCGACTTCGCAGCCTATCGCTCC, and optionally an equivalent thereof.

Intracellular domain: CD3 zeta signaling region polynucleotide sequence:

(SEQ ID NO: 5)
AGAGTGAAGTTCAGCAGGAGCGCAGACGCCCCCGCGTACCAGCAGGGCC

AGAACCAGCTCTATAACGAGCTCAATCTAGGACGAAGAGAGGAGTACGA

TGTTTTGGACAAGAGACGTGGCCGGGACCCTGAGATGGGGGGAAAGCCG

AGAAGGAAGAACCCTCAGGAAGGCCTGTACAATGAACTGCAGAAAGATA

AGATGGCGGAGGCCTACAGTGAGATTGGGATGAAAGGCGAGCGCCGGAG

GGGCAAGGGGCACGATGGCCTTTACCAGGGTCTCAGTACAGCCACCAAG

GACACCTACGACGCCCTTCACATGCAGGCCCTGCCCCCTCGCTAA, and optionally an equivalent thereof.

Non-limiting examples of CAR extracellular domains capable of binding to antigens are the binding domain targeting the neoantigen peptide of this disclosure sequences that specifically bind CD19 antigen.

Further embodiments of each exemplary domain component include other proteins that have analogous biological function that share at least 70%, or alternatively at least 80% amino acid sequence identity, preferably 90% sequence identity, more preferably at least 95% sequence identity with the proteins encoded by the above disclosed nucleic acid sequences. Further, non-limiting examples of such domains are provided herein.

As may be used herein, the term "CD8 α hinge domain" refers to a specific protein fragment associated with this name and any other molecules that have analogous biological function that share at least 70%, or alternatively at least 80% amino acid sequence identity, preferably 90% sequence identity, more preferably at least 95% sequence identity with the CD8 α hinge domain sequence as shown herein. Non-limiting examples of such include:

Human CD8 alpha hinge domain amino acid sequence:

(SEQ ID NO: 6)
PAKPTTTPAPRPPTPAPTIASQPLSLRPEACRPAAGGAVHTRGLDFACD
IY, and optionally an equivalent thereof.

Mouse CD8 alpha hinge domain amino acid sequence:

(SEQ ID NO: 7)
KVNSTTTKPVLRTPSPVHPTGTSQPQRPEDCRPRGSVKGTGLDFACDIY, and optionally an equivalent thereof.

As may be used herein, the term "CD8 α transmembrane domain" refers to a specific protein fragment associated with this name and any other molecules that have analogous biological function that share at least 70%, or alternatively at least 80% amino acid sequence identity, preferably 90% sequence identity, more preferably at least 95% sequence identity with the CD8 α transmembrane domain sequence as shown herein. The fragment sequences associated with the amino acid positions 183 to 203 of the human T-cell surface glycoprotein CD8 alpha chain (GenBank Accession No: NP_001759.3), or the amino acid positions 197 to 217 of the mouse T-cell surface glycoprotein CD8 alpha chain (GenBank Accession No: NP_001074579.1), and the amino acid positions 190 to 210 of the rat T-cell surface glycoprotein CD8 alpha chain(GenBank Accession No: NP_113726.1) provide additional example sequences of the CD8α transmembrane domain. The sequences associated with each of the listed accession numbers are provided as follows:

Human CD8 alpha transmembrane domain amino acid sequence:

(SEQ ID NO: 8)
IYIWAPLAGTCGVLLLSLVIT, and optionally an equivalent thereof.

Mouse CD8 alpha transmembrane domain amino acid sequence:

(SEQ ID NO: 9)
IWAPLAGICVALLLSLIITLI, and optionally an equivalent thereof.

Rat CD8 alpha transmembrane domain amino acid sequence:

(SEQ ID NO: 10)
IWAPLAGICAVLLLSLVITLI, and optionally an equivalent thereof.

As may be used herein, the term "CD28 transmembrane domain" refers to a specific protein fragment associated with this name and any other molecules that have analogous biological function that share at least 70%, or alternatively at least 80% amino acid sequence identity, at least 90% sequence identity, or alternatively at least 95% sequence identity with the CD28 transmembrane domain sequence as shown herein. The fragment sequences associated with the GenBank Accession Nos: XM_006712862.2 and XM_009444056.1 provide additional, non-limiting, example sequences of the CD28 transmembrane domain.

As may be used herein, the term "4-1BB costimulatory signaling region" refers to a specific protein fragment associated with this name and any other molecules that have analogous biological function that share at least 70%, or alternatively at least 80% amino acid sequence identity, preferably 90% sequence identity, more preferably at least 95% sequence identity with the 4-1BB costimulatory signaling region sequence as shown herein. A non-limiting example sequence of the 4-1BB costimulatory signaling region include:

(SEQ ID NO: 11)
KRGRKKLLYIFKQPFMRPVQTTQEEDGCSCRFPEEEEGGCEL, and optionally an equivalent thereof.

As may be used herein, the term "ICOS costimulatory signaling region" refers to a specific protein fragment associated with this name and any other molecules that have analogous biological function that share at least 70%, or alternatively at least 80% amino acid sequence identity, preferably 90% sequence identity, more preferably at least 95% sequence identity with the ICOS costimulatory signaling region sequence as shown herein. Non-limiting example sequences of the ICOS costimulatory signaling region are provided in U.S. Patent Application Publication No. 2015/0017141A1 the exemplary polynucleotide sequence provided below.

ICOS costimulatory signaling region polynucleotide sequence:

(SEQ ID NO: 12)
ACAAAAAAGA AGTATTCATC CAGTGTGCAC GACCCTAACG

GTGAATACAT GTTCATGAGA GCAGTGAACA CAGCCAAAAA

ATCCAGACTC ACAGATGTGA CCCTA, and optionally an equivalent thereof.

As may be used herein, the term "OX40 costimulatory signaling region" refers to a specific protein fragment associated with this name and any other molecules that have analogous biological function that share at least 70%, or alternatively at least 80% amino acid sequence identity, or alternatively 90% sequence identity, or alternatively at least 95% sequence identity with the OX40 costimulatory signaling region sequence as shown herein. Non-limiting example sequences of the OX40 costimulatory signaling region include the exemplary sequence provided below.

OX40 costimulatory signaling region polynucleotide sequence:

(SEQ ID NO: 13)
AGGGACCAG AGGCTGCCCC CCGATGCCCA CAAGCCCCCT

GGGGGAGGCA GTTTCCGGAC CCCCATCCAA GAGGAGCAGG

CCGACGCCCA CTCCACCCTG GCCAAGATC, and optionally an equivalent thereof.

As may be used herein, the term "CD28 costimulatory signaling region" refers to a specific protein fragment associated with this name and any other molecules that have analogous biological function that share at least 70%, or alternatively at least 80% amino acid sequence identity, or alternatively 90% sequence identity, or alternatively at least 95% sequence identity with the CD28 costimulatory signaling region sequence shown herein. A non-limiting example includes the sequence encoded by:

CD28 amino acid sequence:

(SEQ ID NO: 14)
MLRLLLALNL FPSIQVTGNK ILVKQSPMLV AYDNAVNLSC

KYSYNLFSRE FRASLHKGLDSAVEVCVVYG NYSQQLQVYS

KTGFNCDGKL GNESVTFYLQ NLYVNQTDIY

FCKIEVMYPPPYLDNEKSNG TIIHVKGKHL CPSPLFPGPS

KPFWVLVVVG GVLACYSLLVTVAFIIFWVR SKRSRLLHSD

YMNMTPRRPG PTRKHYQPYA PPRDFAAYRS, and equivalents thereof.

As may be used herein, the term "CD3 zeta signaling domain" refers to a specific protein fragment associated with this name and any other molecules that have analogous biological function that share at least 70%, or alternatively at least 80% amino acid sequence identity, or alternatively 90% sequence identity, or alternatively at least 95% sequence identity with the CD3 zeta signaling domain sequence as shown herein. A non-limiting example of sequence of the CD3 zeta signaling domain includes:

CD3 zeta signaling domain:

(SEQ ID NO: 15)
RVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATK

DTYDALHMQALPPR.

As may be used herein, a "first generation CAR" refers to a CAR comprising an extracellular domain capable of binding to an antigen, a transmembrane domain derived from a polypeptide different from a polypeptide from which the extracellular domain is derived, and at least one intracellular domain. A "second generation CAR" refers to a first generation CAR further comprising one costimulation domain (e.g., 4-1BB or CD28). A "third generation CAR" refers to a first generation CAR further comprising two costimulation domains (e.g. CD27, CD28, ICOS, 4-1BB, or OX40). A "fourth generation CAR" (also known as a "TRUCK") refers to a CAR T-cell further engineered to secrete an additional factor (e.g., proinflammatory cytokine IL-12). A The term "transduce" or "transduction" as it is applied to the production of chimeric antigen receptor cells refers to the process whereby a foreign nucleotide sequence is introduced into a cell. Transduction may be done via a vector.

As may be used herein, the term "vector" refers to a nucleic acid construct deigned for transfer between different hosts, including but not limited to a plasmid, a virus, a cosmid, a phage, a BAC, a YAC, etc. A "viral vector" is defined as a recombinantly produced virus or viral particle that comprises a polynucleotide to be delivered into a host cell, either in vivo, ex vivo or in vitro. Plasmid vectors may be prepared from commercially available vectors. Viral vectors may alternatively be produced from baculoviruses, retroviruses, adenoviruses, AAVs, etc. according to techniques known in the art. The viral vector may be a lentiviral vector. Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) *PNAS USA*, 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) *Curr. Opin. Biotechnol.*, 5:434-439 and Ying et al. (1999) *Nat. Med.*, 5(7):823-827. Where gene transfer is mediated by a retroviral vector, a vector construct refers to the polynucleotide comprising the retroviral genome or part thereof, and a gene of interest such as a polynucleotide encoding a CAR. Further details as to modern methods of vectors for use in gene transfer may be found in, for example, Kotterman, et al., (2015) "Viral Vectors for Gene Therapy: Translational and Clinical Outlook," *Annual Review of Biomedical Engineering*, 17. Vectors that contain both a promoter and a cloning site into which a polynucleotide can be operatively linked are well known in the art. Such vectors are capable of transcribing RNA in vitro or in vivo, and are commercially available from sources such as Agilent Technologies (Santa Clara, Calif.) and Promega Biotech (Madison, Wis.).

As may be used herein, the term "culturing" refers to growing cells in a culture medium under conditions that favor expansion and proliferation of the cell. The term "culture medium" or "medium" is recognized in the art and refers generally to any substance or preparation used for the cultivation of living cells. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase to which cells growing on a petri dish or other solid or semisolid support are exposed. The term "medium" also refers to material that is intended for use in a cell culture, even if it has not yet been contacted with cells. In other words, a nutrient rich liquid prepared for culture is a medium. Similarly, a powder mixture that when mixed with water or other liquid becomes suitable for cell culture may be termed a "powdered medium." "Defined medium" refers to media that are made of chemically defined (usually purified) components. "Defined media" do not contain poorly characterized biological extracts such as yeast extract and beef broth. "Rich medium" includes media that are designed to support growth of most or all viable forms of a particular species. Rich media often include complex biological extracts. A "medium suitable for growth of a high-density culture" is any medium that allows a cell culture to reach an OD600 of 3 or greater when other conditions (such as temperature and oxygen transfer rate) permit such growth. The term "basal medium" refers to a medium which promotes the growth of many types of microorganisms which do not require any special nutrient supplements. Most basal media generally comprise of four basic chemical groups: amino acids, carbohydrates, inorganic salts, and vitamins. A basal medium generally serves as the basis for a more complex medium, to which supplements such as serum, buffers, growth factors, lipids, and the like are added. In one aspect, the growth medium may be a complex medium with the necessary growth factors to support the growth and expansion of the cells of the disclosure while maintaining their self-renewal capability. Examples of basal media include, but are not limited to, Eagles Basal Medium, Minimum Essential Medium, Dulbecco's Modified Eagle's Medium, Medium 199, Nutrient Mixtures Ham's F-10 and Ham's F-12, McCoy's 5A, Dulbecco's MEM/F-I 2, RPMI 1640, and Iscove's Modified Dulbecco's Medium (IMDM).

Aspects of the Disclosure

In one aspect, a method of identifying a neoantigen peptide candidate is disclosed. The method involves generating tumor sequence reads from a tumor sample and normal sequence reads from a normal control sample; comparing the tumor sequence reads with the normal sequence reads to identify one or more exome variants; selecting from the one or more exome variants a set of exome variants that satisfy a variant calling policy; generating for at least one exome variant of the set of exome variants that satisfy the variant calling policy one or more peptides, each peptide having one or more mutated amino acids at one or more pre-selected locations of the peptide; and (e) evaluating immunogenicity for one or more of the peptides. In certain embodiments, the peptides are synthetic peptides.

In embodiments, the method further involves identifying at least one peptide demonstrating a predetermined immunogenic activity as a neoantigen peptide candidate. In embodiments, the method is devoid of an in silico epitope binding prediction algorithm. In embodiments, the tumor sequence reads are tumor mRNA sequence reads, tumor exome sequence reads, or both. In embodiments, the non-tumor sequence reads are non-tumor exome sequence reads. In embodiments, the predetermined immunogenic activity comprises stimulation of a T cell response by the at least one peptide. In embodiments, the predetermined immunogenic activity comprises production of IFN-γ or IL-5 by a T cell. In embodiments, the T cell response is predominantly a CD4+ T cell response. In embodiments, the CD4+ T cell response is a Th1 or Th2 response. In embodiments, the T cell response is predominantly a CD8+ T cell response. In embodiments, the T cell response is both a CD4+ T cell response and a CD8+ T cell response. In embodiments, the method further involves producing the at least one identified peptide. In further embodiments, the method further involves treating an individual associated with the tumor sample with a composition comprising the at least one identified peptide, or an engineered immune cell that biologically recognizes the at least one peptide.

As detailed herein, the described algorithms can be used to select preferred neoantigen peptides for use as treatments, including personal anti-cancer vaccines. There are other potential uses of the described algorithms, including but not limited to use for predicting the efficacy of checkpoint blockades and other immune-activating treatments for a tumor in question related to the availability of targets for treating said tumor. Additionally, the described algorithms can be used to select peptides that can be used for immune monitoring of the response of a given patient who is being treated with a peptide-based vaccine or any other immune-based interventions. Further, the described algorithms can also be used for non-cancer purposes, such as for predicting transplant compatibility or identifying antigens associated with autoimmune diseases, including targets for treatment (including tolerogenic therapies) or prevention of autoimmune diseases, e.g., identification of targets of autoimmune effector cells.

In another aspect, a neoantigen peptide is disclosed. The neoantigen peptide is produced based on the method of identification detailed herein. In another aspect, an engineered immune cell is disclosed. The engineered immune cell is configured to biologically recognize the neoantigen peptide detailed herein. In embodiments, the engineered immune cell comprises a CD4+ T cell, a CD8+ T cell, a tissue-resident memory cell ($T_{RM}$), a NKT cell, or a NK cell. In embodiments, the engineered immune cell comprises an engineered TCR, modified TCR, or a chimeric antigen receptor (CAR). In embodiments, the CAR further comprises one or more costimulatory signaling regions. In embodiments, the engineered immune cell is disclosed for use in treating an individual having cancer.

In embodiments, the neoantigen peptide or the engineered immune cell detailed herein is used to treat an individual having cancer.

In another aspect, an immune composition is disclosed. In embodiments, the immune composition includes a pharmaceutically acceptable carrier, diluent, or excipient; an adjuvant; and the at least one identified peptide detailed herein, or the engineered immune cell detailed herein. In another aspect, a method of treating cancer is disclosed. The method involves delivering a therapeutically effective amount of the immune composition detailed herein to an individual in need thereof. In another aspect, a prophylactic method of preventing cancer is disclosed. The method involves delivering a prophylactically effective amount of the composition described herein to an individual in need thereof.

In further embodiments, a treatment protocol makes use of a personalized cancer vaccine by making use of the peptides selected using the methods described herein. Up to 1, or 2, or 3, or 4, or 5, or 6, or 7, or 8, or 9, or 10, or 11, or 12, or 13, or 14, or 15, or 16, or 17, or 18, or 19, or 20, or 21, or 22, or 23, or 24, or more neoantigen peptides selected using the methods described herein are administered to an individual in need thereof. In embodiments, the neoantigen peptides are delivered intramuscularly but other routes of administration are also contemplated as will be understood by those skilled in the relevant art. In certain embodiments, up to 8 neoantigen peptides per injection are injected to an individual such that three injections will accommodate up to 24 neoantigen peptides. Such injections occur about every 7 days or every 7 days for about 2 to about 4 weeks. In certain embodiments, such injections are then administered about once or about twice every three weeks for an additional $10^{-24}$ or $10^{-22}$, or $10^{-20}$ weeks. These injections may be combined with other compositions, including but not limited to polyinosinic-polycytidylic acid stabilized with polylysine and carboxymethylcellulose, starting, for e.g., at week one. In further embodiments, these described injections are combined with checkpoint-inhibition treatments, such as anti-PD-1 (Nivolumab® or Pembrolizumab®) or anti-PD-L1 (Atezolizumab® or Durvalumab®), starting at about week 1, or week 2, or week 3 (when the injections are given every 7 days for only 2 weeks), or starting at about week 4, or week 5, or week 6 (when the injections are given every 7 days for 4 weeks).

In another aspect of the disclosure, neoantigens are selected for functional immunological testing and for inclusion in a peptide vaccine as follows. Once the list of ranked putative neoantigens is obtained from the algorithm/bioinformatics, neoantigens are selected for functional testing. Up to 24 antigens can be included in the vaccine. Since only ~40% of antigens tested will be validated by the functional assays, the aim is to test ~50 antigens in the functional assays to end up with approximately 24 neoantigens for the vaccine. The 50 antigens for functional assay testing are selected as follows: 1) the top 50 ranked Level 4 neoantigens are selected; and 2) if there are not 50 μLevel 4s, Level 3 neoantigens are selected base on which Level 3s are in cancer associated genes identified in COSMIC or TCGA. Following the functional assay, if there are more than 24 neoantigens validated from the functional assays, those antigens previously verified as neoantigen or that are in cancer associated genes in COSMIC or TCGA are selected.

In another aspect, methods of identifying a neoantigen peptide candidate, and systems capable of carrying out such methods, are described herein. The systems may incorporate a computer processor and the methods may be carried out by a computer processor. The methods may comprise generating tumor sequence reads from a tumor sample and normal sequence reads from a normal control sample comparing the tumor sequence reads with the normal sequence reads to identify one or more exome variants; selecting from the one or more exome variants a set of exome variants that satisfy a variant calling policy; generating for at least one exome variant of the set of exome variants that satisfy the variant calling policy one or more peptides, each peptide having one or more mutated amino acids at one or more pre-selected locations of the peptide; evaluating immunogenicity for one or more of the peptides; and identifying at least one peptide demonstrating a predetermined immunogenic activity as a neoantigen peptide candidate. The tumor sequence reads may be tumor mRNA sequence reads, tumor exome sequence reads, or both. The non-tumor sequence reads may be non-tumor exome sequence reads. The predetermined immunogenic activity may comprise the peptide stimulating a T-cell response. The one or more peptides may comprise one or more 20-mer peptides having a non-synonymous mutation at the $6^{th}$ or $15^{th}$ position. The set of peptides may comprise one or more frameshift peptides, wherein the one or more frameshift peptides are generated by first synthesizing one or more long peptides, each with mutated amino acid at a $6^{th}$ or a $15^{th}$ position and ending at a first stop codon, and then breaking the one or more long peptides into 20-mers.

The methods may comprise selecting the set of exome variants that satisfy the variant calling policy comprises selecting one or more exome variants that have characteristics of the group of: read depth at SNP position of the variant is at least about 1 in a normal exome, a tumor exome and a tumor transcriptome; variant allele frequency in the normal exome is equal to about 50% or less; variant allele frequency in the tumor exome is at least about 1%; variant alternate allele reads in the tumor RNA is at least about 1; and variant is protein changing.

Generating the one or more peptides may comprise: generating two or more SNV (single nucleotide variant) peptides each having mutated amino acids at pre-selected locations; and/or (b) generating two frameshift variant peptides identified (FRP) each having mutated amino acids at pre-selected locations. The method may further comprise re-stimulating a peripheral blood mononuclear cell with the SNV and/or FRP peptides that generated an IFN-γ and/or an IL-5 response and measuring the IFN-γ and IL-5 responses generated by said peptides upon re-stimulation. Every step of the method may exclude in silico epitope binding prediction algorithms, e.g. in silico MHC binding prediction algorithms. It is preferred that each step of the method exclude in silico epitope binding prediction algorithms, e.g., in silico MHC binding prediction algorithms. Methods of identifying a neoantigen peptide candidate that excludes in silico binding epitope binding prediction algorithms may comprise performing whole-exome sequencing (WES) and RNA sequencing (RNA-seq) of a tumor sample and a normal control sample and selecting one or more exome variants according to a predetermined variant selection policy.

Methods and systems described herein may also be employed to prepare peptides and engineered immune cells. Peptides (neoantigens; peptides or proteins comprising neoepitopes) may be identified by methods and/or systems summarized in the foregoing paragraph. Engineered immune cells that target identified peptides are also taught herein. The engineered immune cells may comprise a CD4 T cell, a CD8 T cell, a tissue-resident memory cells ($T_{RM}$) and/or a Natural Killer (NK) T cell. The engineered immune cells may comprise an engineered TCR, modified TCR, or chimeric antigen receptor (CAR). The engineered immune cells may be such that the chimeric antigen receptor (CAR) comprises: an antigen binding domain; a hinge domain; a transmembrane domain; and an intracellular domain.

The engineered immune cells may be such that the CAR further comprises one or more costimulatory signaling regions. The CAR may comprise: an antigen binding domain targeting the identified peptide; a hinge domain; a CD28 or a CD8 α transmembrane domain; one or more costimulatory regions selected from a CD28 costimulatory signaling region, a 4-1BB costimulatory signaling region, an ICOS costimulatory signaling region, and an OX40 costimulatory region; and a CD3 zeta signaling domain. The antigen binding domain targeting the peptide of the CAR may comprise a single-chain variable fragment (scFv). The scFv of the CAR may comprise a heavy chain variable region and a light chain variable region. The antigen binding domain targeting the peptides of the CAR may further comprise a linker polypeptide located between the scFv heavy chain variable region and the scFv light chain variable region. The linker polypeptide of the CAR may comprise a polypeptide of the sequence (GGGGS)n wherein n is an integer from 1 to 6 (SEQ ID NO:34). The CAR may further comprise a detectable marker attached to the CAR. The CAR may further comprise a purification marker attached to the CAR. The modified T-cell may comprise a polynucleotide encoding the CAR, and optionally, the polynucleotide may encode an antigen binding domain targeting the engineered peptide. The polynucleotide may further comprise a promoter operatively linked to the polynucleotide to express the polynucleotide in said modified T-cell. The polynucleotide may further comprise a 2A self-cleaving peptide (T2A) encoding polynucleotide sequence located upstream of a polynucleotide encoding the antigen binding domain targeting the identified peptide (neoantigen; peptide or protein comprising a neoepitope). The polynucleotide may further comprise a polynucleotide encoding a signal peptide located upstream of a polynucleotide encoding the antigen binding domain targeting the identified peptide. The polynucleotide may further comprise a vector, e.g., a plasmid or a viral vector selected from the group of a retroviral vector, a lentiviral vector, an adenoviral vector, and an adeno-associated viral vector. Methods and systems described herein, e.g., those summarized in the foregoing paragraph, may also be employed to prepare substantially homogeneous population of the engineered immune cells and/or a heterogeneous population of the engineered immune cells. Thus, further provided herein are peptides, engineered immune cells, and/or populations of engineered immune cells produced by one or more methods, or obtained using one or more systems, as described herein.

Methods and systems described herein may also be employed, in addition to preparing peptides and engineered immune cells, to prepare compositions of matter comprising the peptides and/or engineered immune cells. Compositions described herein may comprise peptides (neoantigens; peptides or proteins comprising neoepitopes), e.g., as identified by methods and/or systems summarized in the foregoing paragraphs. Compositions may also comprise engineered immune cells that target identified peptides, e.g., CD4 T cells, a CD8 T cells, tissue-resident memory cells ($T_{RM}$) and/or a Natural Killer (NK) T cells. Compositions may comprise a carrier and one or more of: engineered immune cells, one or more populations of cells, and/or one or more identified peptides. Carriers may be pharmaceutically acceptable carriers, which may further comprise one or more cryoprotectants.

Also described herein are methods of treating cancer, eliciting an anti-tumor response and/or providing anti-tumor immunity in a subject. Such methods may comprise administering to the subject an effective amount of one or more of the following: a population of immune cells; one or more engineered immune cells; a composition, e.g., a pharmaceutical composition; an antibody; and/or an antigen binding fragment that targets one or more identified peptides summarized in the foregoing paragraphs. The immune cell may be a CD4 T cell, a CD8 T cell, a tissue-resident memory cells ($T_{RM}$) or a Natural Killer (NK) T cell. The T-cells may be autologous to the subject being treated. The antibody may be an IgG, IgA, IgM, IgE or IgD, or a subclass thereof. The antibody may be an IgG selected from the group of IgG1, IgG2, IgG3 or IgG4. The antigen binding fragment may be selected from the group of an Fab, Fab', F(ab')2, Fv, Fd, single-chain Fvs (scFv), disulfide-linked Fvs (sdFv) or VL or VH.

Also described herein is a method of diagnosing a subject having cancer, comprising contacting a sample with an agent that detects the presence of an identified peptide, e.g., as described in the foregoing four paragraphs, wherein the presence of the one or more neoantigen peptide is diagnostic of cancer. Also described herein is a method of diagnosing a subject having cancer, comprising contacting a sample with an agent that detects an immune response, e.g. a T cell response, to an identified peptide, wherein such an immune response to one or more neoantigen peptide is diagnostic of cancer. Also described herein is a method of determining prognosis of a subject having cancer comprising contacting a sample with an agent that detects the presence of the identified peptide in the sample, wherein the presence of the one or more neoantigen peptide indicates a decreased probability and/or duration of survival. Also described herein is a method of determining prognosis of a subject having cancer, comprising contacting a sample with an agent that detects an immune response, e.g. a T cell response, to an identified peptide, wherein such an immune response to one or more neoantigen peptides indicates an increased probability and/or duration of survival. In either diagnosis or treatment, a sample may comprise a cell, tissue, an organ biopsy, an epithelial tissue, a lung, respiratory or airway tissue or organ, a circulatory tissue or organ, a skin tissue, bone tissue, muscle tissue, head, neck, brain, skin, bone and/or blood sample. The cancer or tumor may comprise a cancer or tumor with a low mutational burden. The cancer or tumor may be an epithelial, a head, neck, lung, lung, prostate, colon, pancreas, esophagus, liver, skin, kidney, adrenal gland, brain, or comprises a lymphoma, breast, endometrium, uterus, ovary, testes, lung, prostate, colon, pancreas, esophagus, liver, skin, kidney, adrenal gland and/or brain cancer or tumor, a microsatellite-stable colorectal adenocarcinoma, neuroendocrine carcinoma, a metastasis or recurring tumor, cancer or neoplasia, a non-small cell lung cancer (NSCLC) and/or head and neck squamous cell cancer (HNSCC). The diagnostic or treatment method may further comprise administering to the subject an effective amount of a cancer therapy. The cancer therapy may be one or more of chemotherapy, immunotherapy, or radiation therapy. The subject may be a mammal, e.g., a human, canine, feline, simian, bovine, ovine, or other mammalian animal.

Also provided herein are kits comprising instructions for use and one or more of: the engineered immune cells, the populations of cells, the identified peptides, and/or the compositions, each as summarized herein. The instructions for use may provide directions to conduct the methods summarized herein.

A method described herein, e.g., a method of identifying candidate neoantigens, as summarized in one of the foregoing six paragraphs, may comprise: filtering, e.g., by a processor, an input data stream of variants to remove variants associated with somatic cells; identifying, e.g., by the processor, the input data stream to remove synonymous variants; associating, e.g., by the processor, variants in the input data stream associated with a tumor; observing, e.g., by the processor, RNA in a sample and identifying variants in the input data stream corresponding to the RNA. Each of foregoing steps may preferably be performed by the processor or using the processor. The method may further comprise gathering, e.g., by the processor, all or substantially all (e.g., +/−1%, 2%, 5% or 10%) variants taken from the sample. The step of associating may further comprise filtering, by the processor, variants in the input data stream for a predetermined depth. The method may further comprise sorting, e.g., by the processer and after the observing, basing variants in the input data stream, for e.g., by the processor, upon at least one of the observing, associating, or filtering to form a sorted list. The step of associating may comprise matching the ratio of a 95% confidence interval for a lower bound of a frequency of a variant in the tumor sample to a 95% confidence interval for an upper bound of a SNP frequency in a somatic sample. The method may comprise cross checking, e.g., by the processor, the sorted list against a cancer genomic repository. In any of the foregoing methods, each step may preferably be performed by or with a processor.

In another aspect, a method is described herein, e.g., a method of identifying candidate neoantigens, as summarized in one of the foregoing six paragraphs, may comprise: removing, e.g., by a processor, from an input data stream of variants, variants that are synonymous; filtering, e.g., by the processor, the input data stream of variants for sequencing errors; associating, e.g., by the processor, the input data stream of variants for associations with somatic cells; observing, e.g., by the processor, RNA in a sample and identifying variants in the input data stream corresponding to the RNA. Each of foregoing steps may preferably be performed by the processor or using the processor. The method may further comprise gathering, e.g., by the processor, all or substantially all (e.g., +/−1%, 2%, 5% or 10%) variants taken from the sample. The step of filtering the input data stream of variants for sequencing errors may comprise filtering the input data stream for a predetermined depth. The method may further comprise sorting, e.g., by the processer and after the observing, basing variants in the input data stream, for e.g., by the processor, upon at least one of the observing, removing, associating, or filtering. The associating step may comprise matching the ratio of a 95% confidence interval for a lower bound of a frequency of a variant in the tumor sample to a 95% confidence interval for an upper bound of a SNP frequency in a somatic sample.

Described herein are systems and methods embodying an unbiased approach to neoantigen identification and discovery. In some embodiments, all tumor-related mutations identified by exome sequencing may be synthesized. In some embodiments, some or all of the mutations may be tested in vitro for immunogenicity by co-culture with autologous lymphocytes derived from peripheral blood specimens.

Further described herein are systems and methods embodying a functional neoantigen identification pipeline that permits rapid identification and validation of tumor-specific neoantigens, which may be devoid of in silico epitope binding prediction algorithms. For moderately mutated malignancies, such as microsatellite-stable colorectal adenocarcinoma, pancreatic adenocarcinoma, neuroendocrine carcinoma and head/neck squamous cell carcinoma, direct testing of all candidate neoantigens may be feasible due to a more limited repertoire of candidate neoantigens. The results reported herein indicate that a functional approach to tumor neoantigen identification and validation may promptly identify neoantigens from limited patient biospecimens, may be more sensitive than existing methodologies for neoantigen identification, may detect both MHC class I and class II neoepitopes, and may be amenable to high throughput screening for patients with a diversity of cancer histologies.

Thus, additional aspects disclosed herein provide methods and systems of identifying a neoantigen peptide candidate comprising, or consisting essentially of, or yet further consisting of: generating, e.g. by one or more processors, tumor sequence reads from a tumor sample and normal sequence reads from a normal control sample; comparing, e.g., by one or more processors, the tumor sequence reads with the normal sequence reads to identify one or more exome variants; selecting, e.g., by one or more processors, from the plurality of exome variants a set of exome variants that satisfy a variant calling policy; generating for at least one exome variant of the set of exome variants that satisfy the variant calling policy one or more peptides, each peptide having one or more mutated amino acids at one or more pre-selected locations of the peptide; and identifying at least one peptide demonstrating a predetermined immunogenic activity as a neoantigen peptide candidate. The immunogenic activity measured in the method may comprise release of IFN-γ and/or IL-5 by PBMCs. Such methods may exclude in silico epitope binding prediction algorithms.

Also disclosed herein are methods of identifying one or more neoantigen peptide candidates, which may exclude in silico epitope binding prediction algorithms, comprising performing whole-exome sequencing (WES) and RNA sequencing (RNA-seq) of a tumor sample and a normal control sample and selecting one or more exome variants according to a predetermined variant selection policy. The neoantigen peptide may stimulate a T-cell response when presented by the MHC class I or class II molecules on a surface of a cancer cell. Selecting the set of exome variants that satisfy the variant calling policy may comprise, or consist essentially of, or yet further consist of selecting one or more exome variants that have one or more characteristics of the group of: read depth at a SNP (single nucleotide polymorphism) position of the variant is at least about 1 in a normal exome, a tumor exome and a tumor transcriptome; variant allele frequency in the normal exome is equal to about 50% or less; variant allele frequency in the tumor exome is at least about 1%; variant alternate allele reads in the tumor RNA is at least about 1; and variant is protein changing.

Generating the one or more peptides may comprise, or consist essentially of, or yet further consist of: generating one or more, e.g., two or more SNV (single nucleotide variant) peptides each having mutated amino acids at pre-selected locations, e.g., at positions 6 and/or 15; and/or (b) generating one or more, e.g., two or more FRP (frameshift variant peptides) identified each having mutated amino acids at pre-selected locations, e.g., at positions 6 and/or 15.

Selecting the set of exome variants that satisfy the variant calling policy may comprise, or consist essentially of, or yet further consist of selecting one or more exome variants that meet the criteria for variant calling set out hereinafter. In certain specific embodiments, the variants selected may satisfy the following criteria:

min_tum_depth: 10
min_nrm_depth: 10
min_tum_alt_freq: 0.05
max_nrm_alt_freq: 0.05
min_tum2nrm_alt_freq_min_to_max_CI_ratio: 1
critical_ratio_fold_difference: 20

The "critical_ratio_fold_difference" may be at least about 10, between 10 and 100, or not more than 100.

The method of identifying a neoantigen peptide candidate may further comprise, or consist essentially of, or yet further consist of re-stimulating a peripheral blood mononuclear cell with one or more SNV peptides and/or one or more FRP peptides that generated an IFN-γ and/or an IL-5 response and measuring the IFN-γ and IL-5 responses generated by said peptides upon re-stimulation.

Every step of the methods described herein may exclude in silico epitope binding prediction algorithms, wherein the in silico binding prediction may be or comprise, e.g., an in silico MHC epitope binding prediction. The exome variants may be assigned a code indicating a confidence level that the given variant is somatic and expressed below levels of carcinogenesis; and/or the exome variants may be filtered based on the assigned code. The variants may be sorted by at least one of the assigned code, a ratio of the alternate frequency in the tumor sample to that of the normal control sample, Transcripts Per Kilobase Million (TPM) of the gene in which an identified single nucleotide polymorphism occurs, or a tumor genotype ranking. For the methods of identifying a neoantigen peptide described herein, the sequence reads may first be generated in a fastq file, then may be aligned to a reference genome of the normal control sample in a .BAM or .CRAM file, and then may be output and processed to a .VCF file format to identify where any aligned reads differ from the reference genome. Immunogenicity may be evaluated in vitro by co-culture with autologous lymphocytes derived from blood specimens.

As will be appreciated by one skilled in the art, various embodiments and aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "engine," "module" or "system." Furthermore, aspects of the present disclosure may take the form of a computer program product embodied in one or more computer readable medium(s) having computer readable program code embodied thereon. Aspects of the present disclosure may be implemented using one or more analog and/or digital electrical or electronic components, and may include a microprocessor, a microcontroller, an application-specific integrated circuit (ASIC), a field programmable gate array (FPGA), programmable logic and/or other analog and/or digital circuit elements configured to perform various input/output, control, analysis and other functions described herein, such as by executing instructions of a computer program product.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Bioinformatics

Systems and methods in various embodiments may provide an ability to sort, rank, order, or otherwise prioritize and/or categorize potential variants associated with tumor expressed proteins. By identifying variants by the strength of association with tumor cells, a variety of research and clinical actions may be taken. For example, in the clinic, identity of certain variants may be compared to known characteristics of the tumor to better tailor a treatment protocol. This personalization of treatment may be associated with improved medical outcomes as therapeutic protocols may by guided by evidence-based decisions informed by the particular characteristics of the tumor cells. By identifying variants associated with tumor cells, further research may be directed, guided by the variant identity.

Identifying variants associated with tumor cells heretofore, however, has been difficult or impossible. Sequencing genetic material from a patient yields a large number of variants, some of which may be somatic, or not be expressed/expressed at very low levels, or represent sequencing errors. Thus, these obstacles, among others, have prohibited effective identification and sorting of variants associated with tumor cells.

In that regard, in various embodiments, a sample of biological material may be taken. The biological material may contain tumor cells from a subject (e.g., a human or animal), along with somatic cells from the same subject. The genetic material may be amplified and/or sequenced in accordance with methods described herein as well as method known in the industry. Though in various embodiments DNA is sequenced, in further embodiments RNA is sequenced, as well as a combination of DNA and RNA. The resulting sequences may be input into a structured or unstructured data format. Thus, an input file may be created containing many records of genetic sequences.

Figure 7:
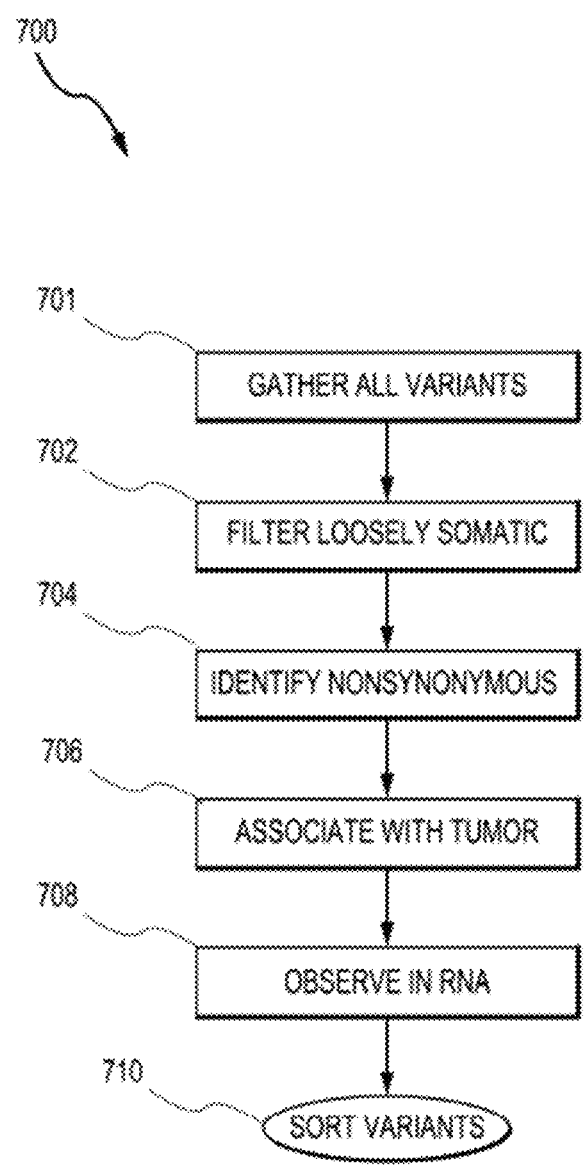
FIG. 7 depicts a method of sorting variants based on association with tumor cells according to aspects of the present disclosure.

With reference to FIG. 7, method 700 is disclosed illustrating a method of sorting variants based on association with tumor cells. In step 701, all variants are gathered into an input data stream. Such data stream may comprise an unstructured data format or a structured data format, such as contained within a relational database or a delimited file, or a metadata tagged file such as XML or JSON. In that regard, step 701 produces an input data stream listing all variants sequenced. In step 702, all sequences are filtered to determine association with somatic cells. In various embodiments, the sequences may be run through a genetic variant detector such as FreeBayes, which is a Bayesian genetic variant detector designed to find small polymorphisms, for example, SNPs (single-nucleotide polymorphisms), as well as other variants. The genetic variant detector may determine a somatic score (SSC) that relates the likelihood of the sequence being associated with a tumor and the likelihood of the sequence being somatic. For example, the somatic score may comprise the sum of the log odds ratios of the tumor (LODT) and normal (LODN) based on the genotype likelihood probabilities from FreeBayes. Step 702 may discard variants with SSCs below a given threshold. For example, those with a score under a predetermined threshold may be discarded, though any suitable threshold may be set. The term discarded, in this context only, means that the discarded variants will not pass through additional filtering steps. These variants may be retained in the input data stream and/or exported to another file. However, discarded variants would not pass to further processing.

In step 704, all variants that meet the predetermined threshold of step 702 are filtered so that only variants that are likely to result in a change at the protein level are passed to further processing. Stated another way, the approach is to remove variants from the input data stream that do not result in changes at the protein level. Such variants may be referred to herein as nonsynonymous variants, and thus only nonsynonymous variants pass to the next level of processing from step 704. As used in this context only, "nonsynonymous" is defined as those variants that result in a change at the protein level. The classification of a variant as "nonsynonymous" may be accomplished by any suitable manner known in the art. For example, various software packages are available for making this determination. In various embodiment, the SNPEff open source tool is used to filter for nonsynonymous variants. SnpEff annotates variants based on their genomic locations and predicts coding effects. Annotated genomic locations include intronic, untranslated region, upstream, downstream, splice site, or intergenic regions. Coding effects such as synonymous or nonsynonymous amino acid replacement, start codon gains or losses, stop codon gains or losses, or frame shifts can be predicted. In various embodiments, SNPEff may update the 'hgvs_protein' annotation and that the protein reference sequence (proteinref) is different from the alternate sequence (proteinalt). In this regard, step 704 removes synonymous variants from the input data stream, passing only or nearly only nonsynonymous variants on to further steps. In various embodiments, where it is difficult, impossible, or impractical to classify a variant as synonymous or nonsynonymous, step 704 may nonetheless include such variants in its output.

As described, step 704 may filters for nonsynonymous variants, and thus there is confidence that the output data stream from step 704 contains variants that lead to changes at the protein level. Thus, at the completion of step 704, the input data stream has been purged or mostly purged of variants that have no effect at the protein level and have some association with tumor cells. In step 706, association with tumor cells is refined further to clarify the association of the variant with tumor cells.

In various embodiments, in step 706, a minimum depth is set for variants associate with tumor cells and variants associated with typical (somatic) cells. The depth thresholds help to separate SNPs from sequence errors. Depth thresholds may be any reasonable threshold, for example between 3 and 50, between 5 and 25, and between 9 and 12. Variants under the depth threshold may be removed from the input data stream.

In various embodiments, step 706 may weigh the frequency of a particular SNP in the tumor sample against frequency of the SNP in a typical (somatic) sample. This ratio may be calculated in any suitable way. In various embodiments, the ratio is that of the 95% confidence interval for the lower bound of the frequency in the tumor sample to the 95% confidence interval for the upper bound of the SNP frequency in the typical (somatic) sample. Setting the minimum for this ratio to 1 ensures 95% confidence that the frequency of the SNP in the tumor sample is greater than that of the normal sample. This may be referred to as the tumor to typical frequency minimum to maximum frequency.

In addition to this ratio of 1, an additional ratio may be calculated that represents the tumor to typical frequency minimum to maximum frequency at the actual tumor and normal depths for the given SNP, if the frequencies were at least a minimum difference, for example, 20%.

At the output of step 706, the input data stream now holds variants that are also more closely associated with tumor cells as opposed to typical cells. In step 708, variants are filtered against those known to exist in RNA. In that regard, in step 708, the biological material sample may have its RNA sequenced. Presence in RNA is indicative of protein expression. Thus, the presence of RNA in the sample that is associated with (i.e., generated from) a variant in the input data stream shows that the variant is not only present, affects the resultant protein, associated with tumor cells, but is being expressed and manufactured by the tumor cell. Variants may be annotated or ranked by the relative amounts of RNA present in a cell, meaning that variants are ranked higher when their respective RNA is found in the sample at relatively higher levels.

Step 708 may output a resultant data set in a ranked or otherwise sorted order. This order may be influenced one or more attributes associated with the variant, for example, a composite score aggregating relationships quantified in any of the preceding steps, a frequency of RNA expression, the ratio of the frequency in the tumor to that in a typical exome sample, the TPM of the gene in which the SNP occurs and/or a tumor genotype rank which is assigned to the various genotype calls made by, for example, Freebayes. In assigning a genotype rank, homozygous for the SNP gets the best rank (1), while homozygous for the reference allele (0/0) gets the lowest rank (6). Intermediate genotypes fall in between. These values, among others may be combined and used to sort the variants.

In step 710, the variants are sorted or otherwise ranked. This order may be influenced one or more attributes associated with the variant, for example, a composite score aggregating relationships quantified in any of the preceding steps, a frequency of RNA expression, the ratio of the frequency in the tumor to that in a typical exome sample, the TPM of the gene in which the SNP occurs and/or a tumor genotype rank which is assigned to the various genotype calls made by, for example, Freebayes. In assigning a genotype rank, homozygous for the SNP gets the best rank (1), while homozygous for the reference allele (0/0) gets the lowest rank (6). Intermediate genotypes fall in between. These values, among others may be combined and used to sort the variants. In various embodiments, these factors, whether alone or in weighted format, may be combined to form a composite ranking score to assist in sorting. For example, frequency of RNA expression may be assigned a numerical value and the ratio of the frequency in the tumor to that in a typical exome sample may be given a numerical value and the two numerical values may be added to create a sorting order. In various embodiments, these factors are instead ordered in cascading order in a predetermined order of attributes. Stated another way, variants may be sorted by frequency of RNA expression and then, within that sorting, sorted by ratio of the frequency in the tumor to that in a typical exome sample.

Figure 8:
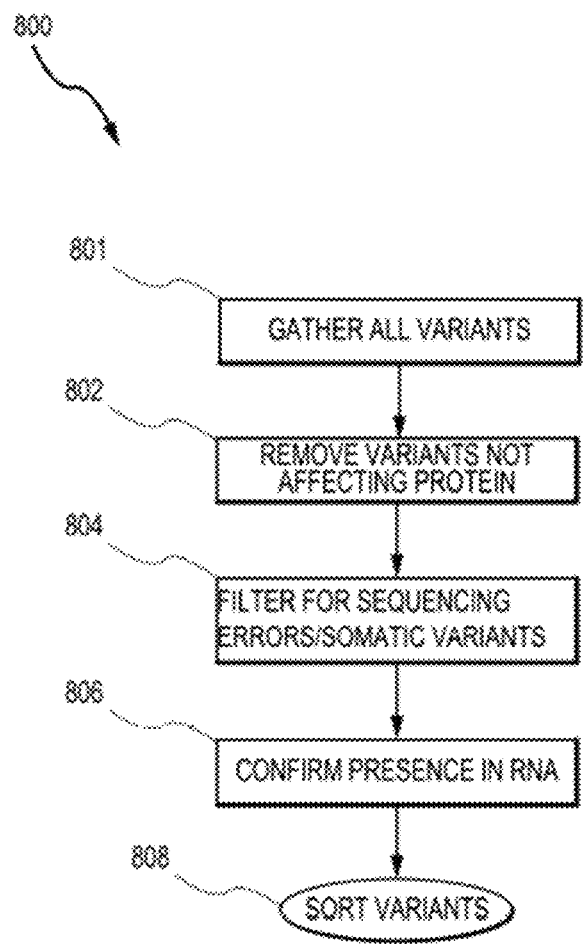
FIG. 8 depicts a method of sorting variants based on association with tumor cells according to aspects of the present disclosure.

With reference to FIG. 8, method 800 is disclosed illustrating a method of sorting variants based on association with tumor cells. In step 801, all variants are gathered into an input data stream. Such data stream may comprise an unstructured data format or a structured data format, such as contained within a relational database or a delimited file, or a metadata tagged file such as XML or JSON. In that regard, step 801 produces an input data stream listing all variants sequenced.

Step 802 is performed on the input data stream prepared by step 801. In step 802, all variants from an input data stream as described above are filtered so that only variants that are likely to result in a change at the protein level are passed to further processing. Stated another way, the approach is to remove variants from the input data stream that do not result in changes at the protein level. Such variants may be referred to herein as nonsynonymous variants, and thus only nonsynonymous variants pass to the next level of processing from step 802. As used in this context only, "nonsynonymous" is defined as those variants that result in a change at the protein level. The classification of a variant as "nonsynonymous" may be accomplished by any suitable manner known in the art. For example, various software packages are available for making this determination. In various embodiment, the SNPEff open source tool is used to filter for nonsynonymous variants. SnpEff annotates variants based on their genomic locations and predicts coding effects. Annotated genomic locations include intronic, untranslated region, upstream, downstream, splice site, or intergenic regions. Coding effects such as synonymous or nonsynonymous amino acid replacement, start codon gains or losses, stop codon gains or losses, or frame shifts can be predicted. In various embodiments, SNPEff may update the 'hgvs_protein' annotation and that the protein reference sequence (proteinref) is different from the alternate sequence (proteinalt). In this regard, step 802 removes synonymous variants from the input data stream, passing only or nearly only nonsynonymous variants on to further steps. In various embodiments, where it is difficult, impossible, or impractical to classify a variant as synonymous or nonsynonymous, step 802 may nonetheless include such variants in its output.

As described, step 802 may filter for nonsynonymous variants, and thus there is confidence that the output data stream from step 802 contains variants that lead to changes at the protein level. Thus, at the completion of step 802, the input data stream has been purged or mostly purged of variants that have no effect at the protein level and have some association with tumor cells. The output data from step 802 is given to step 804. In step 804, association with tumor cells is refined further to clarify the association of the variant with tumor cells.

In step 804, all variants are filtered to increase confidence that the variants are not the result of sequencing errors and to determine association with somatic cells. In various embodiments, the sequences may be run through a genetic variant detector such as FreeBayes, which is a Bayesian genetic variant detector designed to find small polymorphisms, for example, SNPs (single-nucleotide polymorphisms), as well as other variants. The genetic variant detector may determine a somatic score (SSC) that relates the likelihood of the sequence being associated with a tumor and the likelihood of the sequence being somatic. For example, the somatic score may comprise the sum of the log odds ratios of the tumor (LODT) and normal (LODN) based on the genotype likelihood probabilities from FreeBayes. Step 804 may discard variants with SSCs below a given threshold. For example, those with a score under a predetermined threshold may be discarded, though any suitable threshold may be set. The term discarded, in this context only, means that the discarded variants will not pass through additional filtering steps. These variants may be retained in the input data stream and/or exported to another file. However, discarded variants would not pass to further processing. Also in step 804, a minimum depth is set for variants associate with tumor cells and variants associated with typical (somatic) cells. The depth thresholds help to separate SNPs from sequence errors. Depth thresholds may be any reasonable threshold, for example between 3 and 50, between 5 and 25, and between 9 and 12. Variants under the depth threshold may be removed from the input data stream. It is further noted that the sample from which the typical (somatic) cells are derived is from an individual patient, allowing the process to individualize and personalize the delivery and selection of therapy.

Further, step 804 may weigh the frequency of a particular SNP in the tumor sample against frequency of the SNP in a typical (somatic) sample. This ratio may be calculated in any suitable way. In various embodiments, the ratio is that of the 95% confidence interval for the lower bound of the frequency in the tumor sample to the 95% confidence interval for the upper bound of the SNP frequency in the typical (somatic) sample. Setting the minimum for this ratio to 1 ensures 95% confidence that the frequency of the SNP in the tumor sample is greater than that of the normal sample. This may be referred to as the tumor to typical frequency minimum to maximum frequency.

In addition to this ratio of 1, an additional ratio may be calculated that represents the tumor to typical frequency minimum to maximum frequency at the actual tumor and normal depths for the given SNP, if the frequencies were at least a minimum difference, for example, 20%.

At the input of step 806, variants are filtered against those known to exist in RNA. In that regard, in step 806, the biological material sample may have its RNA sequenced. Presence in RNA is indicative of protein expression. Thus, the presence of RNA in the sample that is associated with (i.e., generated from) a variant in the input data stream shows that the variant is not only present, affects the resultant protein, associated with tumor cells, but is being expressed and manufactured by the tumor cell. Variants may be annotated or ranked by the relative amounts of RNA present in a cell, meaning that variants are ranked higher when their respective RNA is found in the sample at relatively higher levels.

Step 806 may output a resultant data set to step 808 where the variants are ranked or otherwise sorted. This order may be influenced one or more attributes associated with the variant, for example, a composite score aggregating relationships quantified in any of the preceding steps, a frequency of RNA expression, the ratio of the frequency in the tumor to that in a typical exome sample, the TPM of the gene in which the SNP occurs and/or a tumor genotype rank which is assigned to the various genotype calls made by, for example, Freebayes. In assigning a genotype rank, homozygous for the SNP gets the best rank (1), while homozygous for the reference allele (0/0) gets the lowest rank (6). Intermediate genotypes fall in between. These values, among others may be combined and used to sort the variants. These values, among others may be combined and used to sort the variants. In various embodiments, these factors, whether alone or in weighted format, may be combined to form a composite ranking score to assist in sorting. For example, frequency of RNA expression may be assigned a numerical value and the ratio of the frequency in the tumor to that in a typical exome sample may be given a numerical value and the two numerical values may be added to create a sorting order. In various embodiments, these factors are instead ordered in cascading order in a predetermined order of attributes. Stated another way, variants may be sorted by frequency of RNA expression and then, within that sorting, sorted by ratio of the frequency in the tumor to that in a typical exome sample.

Figure 9:
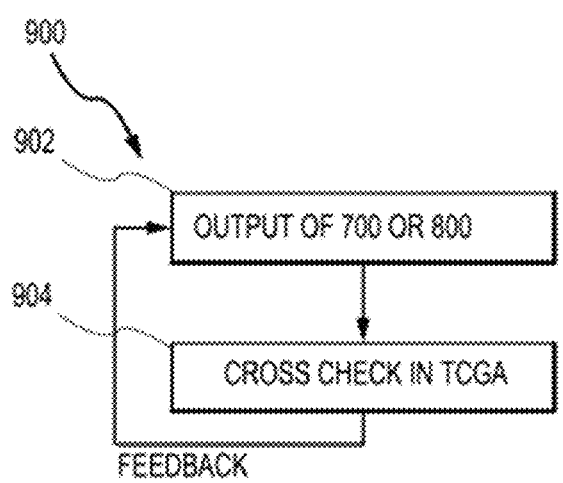
FIG. 9 depicts a method of incorporating the output from methods 700 and/or 800 for cross-checking and/or feedback purposes.
Figure 10:
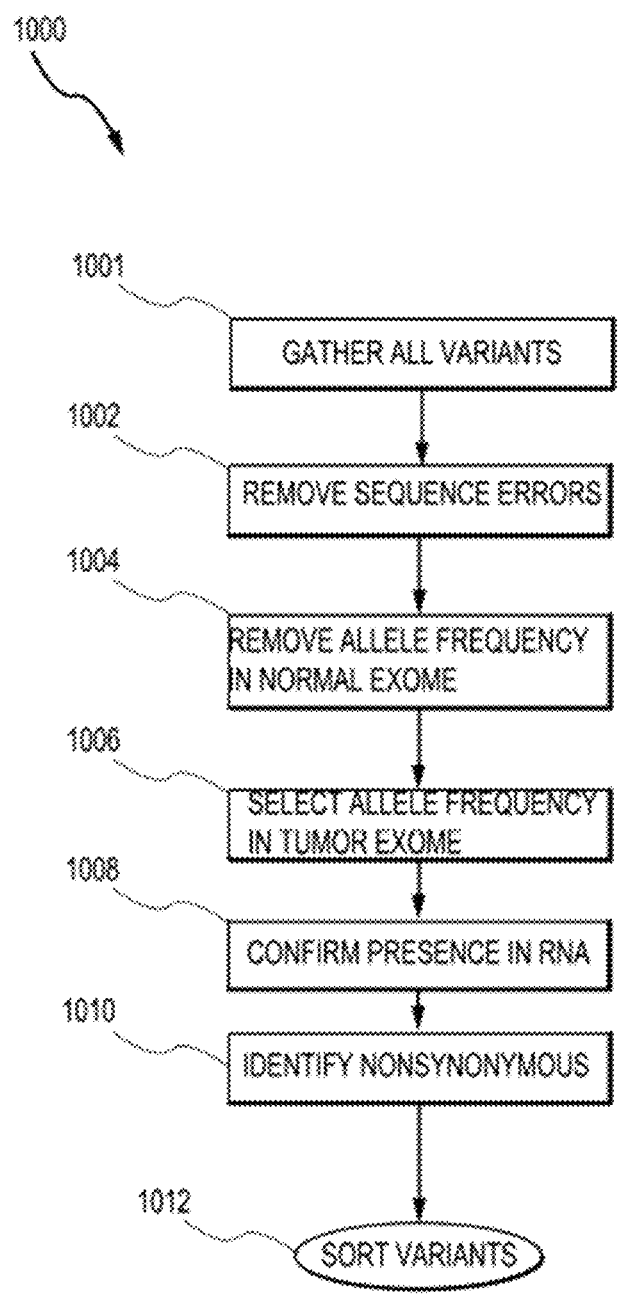
FIG. 10 depicts a method of sorting variants based on association with tumor cells according to aspects of the present disclosure.

The output of methods 700 and 800 may be used in method 900 as shown in FIG. 9. In method 900, the output of methods 700 and 800 (labeled 902) is input into step 904 for cross checking with a cancer genomic repository such as The Cancer Genome Atlas (TCGA). The TCGA molecularly characterized over 20,000 primary cancer and matched normal samples spanning 33 cancer types. The TCGA contains over 2.5 petabytes of genomic, epigenomic, transcriptomic, and proteomic data that is freely accessible to researchers. By linking the output of methods 700 and 800 with data from the TCGA, further insight may be obtained regarding the sorted list of variants from methods 700 and 800. For example, improved characterization of the tumor of a particular subject may be achieved, and, in turn, this may guide selection of therapeutic protocols for the subject. This brings a level of personalization not previously present, as well as allows for improved treatment efficacy. Feedback from the treatment of the subject may input back into methods 700 and 800 to further improve the future sorting process.

For example, with reference to the examples and description herein, all variants are gathered (step 1001). As discussed herein 1, the variants were derived from genomic DNA (gDNA) and total RNA that was purified from fresh tumor specimens using the Qiagen AllPrep DNA/RNA kit (Qiagen) per the manufacturer's protocol. Both Exome and RNA-enrichment libraries were deep sequenced on the Illumina 2500 in Rapid Run mode in a 100×100 paired-end configuration. Sequence reads from Exome-Seq of the tumor and normal samples were aligned to the reference genome GRCh38 using SpeedSeq Align (v0.1.0). Exome variants were identified using SpeedSeq Somatic and variants were annotated using SNPeff (v4.3i). Reads from RNA-Seq of the patient's tumor were aligned using STAR aligner (v2.4.1c). In order to confirm the expression of exome variants in the tumor, the aligned RNA data was compared with the reference genome to check the presence of exome variants using Freebayes software (v0.9.21).

In method 1000, variants are filtered (i.e., removed) from an input data stream and send to further processing. Thus, the resultant data is more likely to include variants that affect protein coding, are protein changing, are present in the tumor, and are being expressed by tumor cells. In that regard, at step 1001, both exome variants in the tumor are present in the input data set.

As a preliminary step (1002), sequence errors are removed. The depth thresholds help to separate SNPs from sequence errors. Depth thresholds may be any reasonable threshold, for example between 3 and 50, between 5 and 25, and between 9 and 12. In various embodiments, the depth threshold of 10 reads, as described herein. Variants under the depth threshold may be removed from the input data stream.

In step 1004, variant allele frequency in the normal exome is determined and variants above a predetermined threshold are removed from the input data stream. This step thus removed variants associated with the normal exome. In various embodiments, 0 is used as a predetermined threshold, meaning that all normal exome variants are removed from the input data stream.

In step 1006, variant allele frequency in the tumor exome is determined and variants below a predetermined threshold are removed from the input data stream. This step thus removes variants associated with the tumor exome that appear less frequently than a predetermined threshold. In that regard, step 1006 identifies variants that frequently occur in the tumor exome. Frequency in tumor exome may be set to any reasonable threshold, for example between 1% to 50%, between 5% and 25%, and between 10% and 20%. In various embodiments, the frequency in tumor exome is greater than or equal to 10%, as described herein. In various embodiments, 20% is used as the threshold for frequency in tumor exome, meaning that variants having a frequency in tumor exome of 20% or greater are selected to remain in the input data stream and those less than 20% are removed.

In step 1008, variant allele frequency in tumor RNA is determined and variants below a predetermined threshold are removed from the input data stream. This step thus removes variants associated with RNA that is expressed less frequently than a predetermined threshold. In that regard, step 1008 identifies variants that frequently occur in the RNA expressed by the tumor. Frequency in tumor RNA may be set to any reasonable threshold, for example between 1% to 50%, between 5% and 25%, and between 10% and 20%. In various embodiments, the frequency in tumor RNA is greater than or equal to 10%, as described herein. In various embodiments, 20% is used as the threshold for frequency in tumor RNA, meaning that variants having a frequency in tumor RNA of 20% or greater are selected to remain in the input data stream and those less than 20% are removed.

In step 1010, variants remaining in the input data stream are filtered so that only variants that are likely to result in a change at the protein level are passed to further processing. Stated another way, the approach is to remove variants from the input data stream that do not result in changes at the protein level. Such variants may be referred to herein as nonsynonymous variants, and thus only nonsynonymous variants pass to the next level of processing. As used in this context only, "nonsynonymous" is defined as those variants that result in a change at the protein level. The classification of a variant as "nonsynonymous" may be accomplished by any suitable manner known in the art, as described above. In this regard, step 1010 removes synonymous variants from the input data stream, passing only or nearly only nonsynonymous variants on to further steps. In various embodiments, where it is difficult, impossible, or impractical to classify a variant as synonymous or nonsynonymous, step 1010 may nonetheless include such variants in its output.

Finally, in step 1012, variants remining in the input data stream are sorted as described above. In this manner, methods 700, 800, 900 and 1000 produce variants that are tumor-expressed (somatic), tumor-specific, protein-changing (non-synonymous) mutations. Such method allow for a highly personalized and targeted approach to therapy. As discussed above, the total number of somatic mutations in these patients ranged from 438 to 3326 mutations, thus highlighting the diversity of targets within a patient population.

The technologies described herein may be incorporated into any of the components, devices, and systems described herein.

In various embodiments, methods 700, 800, 900 and 1000 incorporate hardware and/or software components. For example, a server, a processor, and/or a web client that may execute or cause the execution of methods 700, 800, 900 and 1000, or the like may comprise a server appliance running a suitable server operating system (e.g., MICROSOFT INTERNET INFORMATION SERVICES or, "IIS"). A web client may be any device that allows a user to communicate with a network (e.g., a personal computer, personal digital assistant (e.g., IPHONE®), tablet, cellular phone, kiosk, and/or the like). Devices includes any device (e.g., personal computer, mobile device, etc.) which communicates via any network, for example such as those discussed herein. In various embodiments, systems that execute methods 700, 800, 900 and 1000 systems may comprise and/or run a browser, such as MICROSOFT® INTERNET EXPLORER®, MOZILLA® FIREFOX®, GOOGLE® CHROME®, APPLE® Safari, or any other of the software packages available for browsing the internet. For example, the browser may communicate with a server via network by using Internet browsing software installed in the browser. The browser may comprise Internet browsing software installed within a computing unit or a system to conduct online transactions and/or communications. These computing units or systems may take the form of a computer or set of computers, although other types of computing units or systems may be used, including laptops, notebooks, tablets, handheld computers, personal digital assistants, set-top boxes, workstations, computer-servers, mainframe computers, mini-computers, PC servers, pervasive computers, network sets of computers, personal computers, such as IPADS®, IMACS®, and MACBOOKS®, kiosks, terminals, point of sale (POS) devices and/or terminals, televisions, or any other device capable of receiving data over a network. In various embodiments, browser may be configured to display an electronic channel.

Systems, methods and computer program products are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

As used herein, "satisfy", "meet", "match", "associated with" or similar phrases may include an identical match, a partial match, meeting certain criteria, matching a subset of data, a correlation, satisfying certain criteria, a correspondence, an association, an algorithmic relationship and/or the like.

Terms and phrases similar to "associate" and/or "associating" may include tagging, flagging, correlating, using a look-up table or any other method or system for indicating or creating a relationship between elements, such as, for example, (i) a payment form and (ii) an address. Moreover, the associating may occur at any point, in response to any suitable action, event, or period of time. The associating may occur at pre-determined intervals, periodic, randomly, once, more than once, or in response to a suitable request or action. Any of the information may be distributed and/or accessed via a software enabled link, wherein the link may be sent via an email, text, post, social network input and/or any other method known in the art.

Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

For example, a server executing methods 700, 800, 900 and 1000 may comprise a server appliance running a suitable server operating system (e.g., MICROSOFT INTERNET INFORMATION SERVICES or, "IIS") and having database software (e.g., ORACLE) installed thereon. Methods 700 and 800 may be executed on multiple systems that may be in electronic communication with one another, either directly or through various intermediaries and/or networks.

As used herein, the term "network" includes any cloud, cloud computing system or electronic communications system or method which incorporates hardware and/or software components. Communication among the parties may be accomplished through any suitable communication channels, such as, for example, a telephone network, an extranet, an intranet, Internet, point of interaction device (point of sale device, personal digital assistant (e.g., IPHONE®, BLACKBERRY®), cellular phone, kiosk, etc.), online communications, satellite communications, off-line communications, wireless communications, transponder communications, local area network (LAN), wide area network (WAN), virtual private network (VPN), networked or linked devices, keyboard, mouse and/or any suitable communication or data input modality. Moreover, although the system is frequently described herein as being implemented with TCP/IP communications protocols, the system may also be implemented using IPX, APPLE®talk, IP-6, NetBIOS®, OSI, any tunneling protocol (e.g., IPsec, SSH), or any number of existing or future protocols. If the network is in the nature of a public network, such as the Internet, it may be advantageous to presume the network to be insecure and open to eavesdroppers. Specific information related to the protocols, standards, and application software utilized in connection with the Internet is generally known to those skilled in the art.

For the sake of brevity, conventional data networking, application development, and other functional aspects of the system may not be described in detail herein. Furthermore, the connecting lines shown in the various figures contained herein are intended to represent exemplary functional relationships and/or electronic communications between the various elements. It should be noted that many alternative or additional functional relationships or electronic communications may be present in a practical system.

The system and method may be described herein in terms of functional block components, screen shots, optional selections and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C#, JAVA®, JAVASCRIPT, VBScript, Macromedia Cold Fusion, COBOL, MICROSOFT® Active Server Pages, assembly, PERL, PUP, awk, Python, Visual Basic, SQL Stored Procedures, PL/SQL, any UNIX shell script, and extensible markup language (XML) with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JAVASCRIPT, VBScript or the like.

The various system components may be independently, separately or collectively suitably coupled to the network via data links which includes, for example, a connection to an Internet Service Provider (ISP) over the local loop as is typically used in connection with standard modem communication, cable modem, Dish Networks®, ISDN, Digital Subscriber Line (DSL), or various wireless communication methods, all of which are hereby incorporated by reference. It is noted that the network may be implemented as other types of networks, such as an interactive television (ITV) network. Moreover, the system contemplates the use, sale or distribution of any goods, services or information over any network having similar functionality described herein.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases may be used herein and may include: transaction card data and/or like data useful in the operation of the system. As those skilled in the art will appreciate, user computer may include an operating system (e.g., WINDOWS®, OS2, UNIX®, LINUX®, SOLARIS®, MacOS, etc.) as well as various conventional support software and drivers typically associated with computers.

The present system or any part(s) or function(s) thereof may be implemented using hardware, software or a combination thereof and may be implemented in one or more computer systems or other processing systems. However, the manipulations performed by embodiments were often referred to in terms, such as matching or selecting, which are commonly associated with mental operations performed by a human operator. No such capability of a human operator is necessary, or desirable in most cases, in any of the operations described herein. Rather, the operations may be machine operations or any of the operations may be conducted or enhanced by artificial intelligence (AI) or machine learning. Artificial intelligence may refer generally to the study of agents (e.g., machines, computer-based systems, etc.) that perceive the world around them, form plans, and make decisions to achieve their goals. Foundations of AI include mathematics, logic, philosophy, probability, linguistics, neuroscience, and decision theory. Many fields fall under the umbrella of AI, such as computer vision, robotics, machine learning, and natural language processing. Useful machines for performing the various embodiments include general purpose digital computers or similar devices.

In fact, in various embodiments, the embodiments are directed toward one or more computer systems capable of carrying out the functionality described herein. The computer system includes one or more processors, such as processor. The processor is connected to a communication infrastructure (e.g., a communications bus, cross-over bar, or network). Various software embodiments are described in terms of this exemplary computer system. After reading this description, it will become apparent to a person skilled in the relevant art(s) how to implement various embodiments using other computer systems and/or architectures. Computer system can include a display interface that forwards graphics, text, and other data from the communication infrastructure (or from a frame buffer not shown) for display on a display unit.

Any communication, transmission, communications channel, channel, and/or the like discussed herein may include any system or method for delivering content (e.g., data, information, metadata, etc.), and/or the content itself. The content may be presented in any form or medium, and in various embodiments, the content may be delivered electronically and/or capable of being presented electronically. For example, a channel may comprise a website, mobile application, or device (e.g., FACEBOOK©, APPLE TV©, MICRO SOFT© XBOX©, ROKU©, AMAZON FIRE©, GOOGLE CHROMECAST™, SONY© PLAYSTATION©, NINTENDO© SWITCH©, etc.) a uniform resource locator ("URL"), a document (e.g., a MICROSOFT© Word™ or EXCEL©, an ADOBE© Portable Document Format (PDF) document, etc.), an "ebook," an "emagazine," an application or microapplication (as described herein), an SMS or other type of text message, an email, a FACEBOOK© message, a multimedia message, and/or other type of communication technology.

The systems, computers, computer-based systems, and the like disclosed herein may provide a suitable website or other internet-based graphical user interface which is accessible by users. Practitioners will appreciate that there are a number of methods for displaying data within a browser-based document. Data may be represented as standard text or within a fixed list, scrollable list, drop-down list, editable text field, fixed text field, pop-up window, and the like.

Likewise, there are a number of methods available for modifying data in a web page such as, for example, free text entry using a keyboard, selection of menu items, check boxes, option boxes, and the like.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand. For more information regarding cloud computing, see the NIST's (National Institute of Standards and Technology) definition of cloud computing at http://csrc.nist.gov/publications/nistpubs/800-145/SP800-145.pdf, which is hereby incorporated by reference in its entirety.

In various embodiments, the system and various components may integrate with one or more smart digital assistant technologies. For example, exemplary smart digital assistant technologies may include the ALEXA system developed by AMAZON®, GOOGLE HOME®, APPLE® HOMEPOD®, and/or similar digital assistant technologies. AMAZON® ALEXA, GOOGLE HOME®, and APPLE® HOMEPOD®, may each provide cloud-based voice activation services that can assist with tasks, entertainment, general information, and more. All AMAZON® ALEXA devices, such as the AMAZON ECHO®, AMAZON ECHO DOT®, AMAZON TAP®, and AMAZON FIRE® TV, have access to the ALEXA system. The ALEXA, GOOGLE HOME®, and APPLE® HOMEPOD® systems may receive voice commands via its voice activation technology, and activate other functions, control smart devices, and/or gather information. For example, the smart digital assistant technologies may be used to interact with music, emails, texts, calling, question answering, home improvement information, smart home communication/activation, games, shopping, making to-do lists, setting alarms, streaming podcasts, playing audiobooks, and providing weather, traffic, and other real time information, such as news. The ALEXA, GOOGLE HOME®, and APPLE® HOMEPOD® systems may also allow the user to access information about eligible transaction accounts linked to an online account across all digital assistant-enabled devices.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, JAVA© applets, JAVASCRIPT© programs, active server pages (ASP), common gateway interface scripts (CGI), extensible markup language (XML), dynamic HTML, cascading style sheets (CSS), AJAX (Asynchronous JAVASCRIPT and XML) programs, helper applications, plug-ins, and the like. A server may include a web service that receives a request from a web server, the request including a URL and an IP address (192.168.1.1). The web server retrieves the appropriate web pages and sends the data or applications for the web pages to the IP address. Web services are applications that are capable of interacting with other applications over a communications means, such as the internet. Web services are typically based on standards or protocols such as XML, SOAP, AJAX, WSDL and UDDI. Web services methods are well known in the art, and are covered in many standard texts. As a further example, representational state transfer (REST), or RESTful, web services may provide one way of enabling interoperability between applications.

In various embodiments, one or more servers discussed herein may include application servers (e.g., WEBSPHERE®, WEBLOGIC®, JBOSS©, POSTGRES PLUS ADVANCED SERVER®, etc.). In various embodiments, the server may include web servers (e.g. Apache, IIS, GOOGLE® Web Server, SUN JAVA© System Web Server, JAVA® Virtual Machine running on LINUX® or WINDOWS® operating systems, etc.).

A firewall may include any hardware and/or software suitably configured to protect CMS components and/or enterprise computing resources from users of other networks. Further, the firewall may be configured to limit or restrict access to various systems and components behind the firewall for web clients connecting through a web server. The firewall may reside in varying configurations including Stateful Inspection, Proxy based, access control lists, and Packet Filtering among others. The firewall may be integrated within a web server or any other CMS components or may further reside as a separate entity. The firewall may implement network address translation ("NAT") and/or network address port translation ("NAPT"). The firewall may accommodate various tunneling protocols to facilitate secure communications, such as those used in virtual private networking. The firewall may implement a demilitarized zone ("DMZ") to facilitate communications with a public network such as the internet. The firewall may be integrated as software within an internet server, integrated into any other application server components, reside within another computing device, or take the form of a standalone hardware component.

In various embodiments, the software elements of the system may also be implemented using a JAVASCRIPT® run-time environment configured to execute JAVASCRIPT® code outside of a web browser. For example, the software elements of the system may also be implemented using NODE.JS© components. NODE.JS© programs may implement several modules to handle various core functionalities. For example, a package management module, such as NPM©, may be implemented as an open source library to aid in organizing the installation and management of third-party NODE.JS© programs. NODE.JS© programs may also implement a process manager such as, for example, Parallel Multithreaded Machine ("PM2"); a resource and performance monitoring tool such as, for example, Node Application Metrics ("appmetrics"); a library module for building user interfaces, and/or any other suitable and/or desired module.

Further, illustrations of the process flows and the descriptions thereof may make reference to user WINDOWS© applications, webpages, websites, web forms, prompts, etc. Practitioners will appreciate that the illustrated steps described herein may comprise in any number of configurations including the use of WINDOWS© applications, webpages, web forms, popup WINDOWS© applications, prompts, and the like. It should be further appreciated that the multiple steps as illustrated and described may be combined into single webpages and/or WINDOWS© applications but have been expanded for the sake of simplicity. In other cases, steps illustrated and described as single process steps may be separated into multiple webpages and/or WINDOWS© applications but have been combined for simplicity.

As will be appreciated by one of ordinary skill in the art, the system or any of its components may be embodied as a customization of an existing system, an add-on product, a processing apparatus executing upgraded software, a standalone system, a distributed system, a method, a data processing system, a device for data processing, and/or a computer program product. Accordingly, any portion of the system or a module may take the form of a processing apparatus executing code, an internet-based embodiment, an entirely hardware embodiment, or an embodiment combining aspects of the internet, software and hardware. Furthermore, the system may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

The system and method is described herein with reference to screen shots, block diagrams and flowchart illustrations of methods, apparatus (e.g., systems), and computer program products according to various embodiments. It will be understood that each functional block of the block diagrams and the flowchart illustrations, and combinations of functional blocks in the block diagrams and flowchart illustrations, respectively, can be implemented by computer program instructions.

These computer program instructions may be loaded onto a general-purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user WINDOWS®, webpages, websites, web forms, prompts, etc. Practitioners will appreciate that the illustrated steps described herein may comprise in any number of configurations including the use of WINDOWS®, webpages, web forms, popup WINDOWS®, prompts and the like. It should be further appreciated that the multiple steps as illustrated and described may be combined into single webpages and/or WINDOWS® but have been expanded for the sake of simplicity. In other cases, steps illustrated and described as single process steps may be separated into multiple webpages and/or WINDOWS® but have been combined for simplicity.

In various embodiments, the software elements of the system may also be implemented using a JAVASCRIPT run-time environment configured to execute JAVASCRIPT© code outside of a web browser. For example, the software elements of the system may also be implemented using NODE.JS© components. NODE.JS© programs may implement several modules to handle various core functionalities. For example, a package management module, such as NPM©, may be implemented as an open source library to aid in organizing the installation and management of third-party NODE.JS© programs. NODE.JS© programs may also implement a process manager such as, for example, Parallel Multithreaded Machine ("PM2"); a resource and performance monitoring tool such as, for example, Node Application Metrics ("appmetrics"); a library module for building user interfaces, and/or any other suitable and/or desired module.

As may be used herein, "electronic communication" may comprise a physical coupling and/or non-physical coupling capable of enabling system components to transmit and receive data. For example, "electronic communication" may refer to a wired or wireless protocol such as a CAN bus protocol, an Ethernet physical layer protocol (e.g., those using 10BASE-T, 100BASE-T, 1000BASE-T, etc.), an IEEE 1394 interface (e.g., FireWire), Integrated Services for Digital Network (ISDN), a digital subscriber line (DSL), an 802.11a/b/g/n/ac signal (e.g., Wi-Fi), a wireless communications protocol using short wavelength UHF radio waves and defined at least in part by IEEE 802.15.1 (e.g., the BLUETOOTH© protocol maintained by Bluetooth Special Interest Group), a wireless communications protocol defined at least in part by IEEE 802.15.4 (e.g., the ZIGBEE© protocol maintained by the ZigBee alliance), a cellular protocol, an infrared protocol, an optical protocol, or any other protocol capable of transmitting information via a wired or wireless connection.

As may be used herein, "transmit" may include sending electronic data from one system component to another over a network connection. Additionally, as used herein, "data" or "information" may include encompassing information such as commands, queries, files, data for storage, and the like in digital or any other form.

EXAMPLES

Example 1: Materials & Methods

The following materials and methods were utilized for data generated in this disclosure.
Whole-Exome Sequencing (WES) and RNA Sequencing (RNA-Seq)
WES and RNA-seq were performed at the La Jolla Institute For Immunology sequencing core. Patients consented to UCSD IRB #090401 and biospecimens were prospectively collected and distributed by the Moores Cancer Center Biorepository. Briefly, genomic DNA (gDNA) and total RNA was purified from fresh tumor specimens using the Qiagen AllPrep DNA/RNA kit (Qiagen) per the manufacturer's protocol. Matched reference DNA from each patient was purified from peripheral blood specimens using the Qiagen QIAamp Blood mini kit (Qiagen).

Exome libraries were prepared, according to manufacturer's instructions, using the SureSelect QXT Target Enrichment library preparation kit (G9684B, Agilent). The upfront whole-genome libraries were generated using 50 ng of DNA, fragmented and tagged via the transposase-based QXT enzyme and the subsequent exome enrichments were performed using the SureSelectXT Human All Exon V6 capture probes (5190-8864, Agilent). Tumor RNA was prepared into libraries using the Truseq RNA Access kit (RS-301-2002, Illumina), following manufacturer's instructions with the exception of quartering volumes during the enrichment steps to establish a single-plex protocol. Both Exome and RNA-enrichment libraries were deep sequenced on the Illumina 2500 in Rapid Run mode in a 100×100 paired-end configuration.

Sequence reads from Exome-Seq of the tumor and normal samples were aligned to the reference genome GRCh38 using SpeedSeq Align (v0.1.0). Exome variants were identified using SpeedSeq Somatic and variants were annotated using SNPeff (v4.3i). Reads from RNA-Seq of the patient's tumor were aligned using STAR aligner (v2.4.1c). In order to confirm the expression of exome variants in the tumor, the aligned RNA data was compared with the reference genome to check the presence of exome variants using Freebayes software (v0.9.21).
Variant Calling and Generation of Neoantigen Peptides Variants were considered for further analysis only if they met following criteria: 1) sequencing depth at position of variant ≥10 in normal exome as well as in tumor exome and transcriptome; 2) variant allele frequency in normal exome=0; 3) variant allele frequency in tumor exome ≥10%; 4) variant allele frequency in tumor RNA≥20%; and 5) variant is protein coding and protein changing.

For each SNV (single nucleotide variant) defined somatic (tumor-expressed), two 20-mer peptides containing the mutation at positions 6 and 15, respectively, were generated using a peptide generation pipeline as described herein. For each frameshift, two long peptides, each with mutated amino acid at $6^{th}$ and $15^{th}$ position, respectively, were generated in such a way that the long peptide ends at the first found stop codon in the mutated sequence. These long peptides were then broken into short 20-mers, with overlapping amino acids acting like a bridge between consecutively separated 20-mers. The peptide generation also included validation steps for each peptide, to check for possible errors in the generated mutant peptides.
HLA Binding Prediction Patient HLA genotype was determined computationally using OptiType (v1.3.1) using each patient's exome sequencing and RNA-Seq data as input. Allele-specific HLA binding prediction was performed using NetMHCpan (v4.0) for each 9-11mer peptide containing a mutation. Peptides were considered as predicted binders if the predicted affinity was <500 nM or the predicted percentile rank was <2.
IFN-γ Enzyme-Linked Immunospot (ELISPOT) Assay IFN-γ ELISPOT assays were performed in Multi-ScreenHTS filter plates (Fisher Scientific). Each plate was pretreated with 30 μl of 70% ethanol/well for <1 min, washed 3× with ultra-pure water (Quality Biological) and then coated with 5 μg/ml of IFN-γ capture antibody (50 l/well, clone: 1-D1K, Mabtech, diluted in PBS) and 5 μg/mL of IL-5 capture antibody (50 L/well: clone: TRFK5, Mabetch, diluted in PBS) overnight at 4° C. Anti-CD3 antibody (clone: OKT3, 1-10 μg/ml) was added to the positive-control wells. At the day of co-culture, each plate was washed 5× with PBS and blocked with complete medium without IL-2 for at least 30 min at room temperature. After overnight co-culture (18-24 h), the cells were harvested and transferred into a round-bottom 96-well plate for flow cytometry staining and analysis. Each ELISPOT plate was washed 5× with PBS containing 0.05% Tween 20 (MP Biomedicals) and then incubated for 2 h at 37° C. with anti-Hs IFN-γ-HRP Ab (Mabtech #3420-9H) at 1:200 dilution and anti-Hs IL-5-HRP (Mabtech #3490-6-1000) at 1:1000 dilution. Next, each plate was washed 6× with PBS and incubated for 1 hour with Dual Vectastain (100 μL/well), followed by six washes with ddH$_2$O. Each plate was then developed by adding 100 l/well of vector blue solution at room temperature for 5-10 min followed by six washes with ddH$_2$O and then adding 100 μL/well of AEC substrate for 10 min at room temperature. The reaction was stopped by rinsing thoroughly with cold tap water. After they completely dried, each ELISPOT plate was scanned and counted using an ImmunoSpot plate reader and associated software (Cellular Technologies).

IFN-γ and IL-5 Cytokine Release Assays

Cytokine secretion assays were performed using IFN-γ (Miltenyi Biotec #130-054-202) and IL-5 (Miltenyi Biotec #130-091-624) secretion assay detection kits (Miltenyi Biotec). Human peripheral blood mononuclear cells (PBMC) were stimulated for 3 hours at 37° C. 5% CO$_2$ with 10 g/mL of peptide in 24 well plates at $10^6$ cells/mL of culture medium. Cells were subsequently washed with 10 mL of cold culture medium and then labeled with IFN-γ and IL-5 catch reagent antibodies prior to re-suspension in 10 mL of warm culture medium and incubation for 45 min at 37° C. under slow continuous rotation using a tube rotator. After incubation, cells were washed 2× with warm culture media followed by transfer into 96 well plates, washing with PBS and staining with IFN-γ and IL-5 catch reagent antibodies (10 μL per $10^6$ total cells) in addition to CD4-V500 (BD Biosciences #560768, 1:200 μL), CD8-PB (Biolegend #344718, 1:200 μL) and live/dead fixable viability dye eFluor780 (Invitrogen #65-0865-14, 1:1000) prior to analysis by flow cytometry.

Flow Cytometry Antibodies and Procedures

Cells were stained with fluorescent-labeled antibodies (BioLegend, San Diego, CA; BD-Bioscience Pharmingen, San Diego, CA; or eBiosciences, San Diego, CA) and analyzed by either FACSCalibur or LSR II flow cytometer (BD, San Diego, CA). Gates and quadrants were set based on isotype control staining unless otherwise indicated.

Whole Transcriptome Single-Cell Paired-End RNA-Seq

This assay was adapted from the Smart-seq2 protocol (e.g., Picelli et al. (2013) *Nat. Methods*). Single cells were sorted into wells of 96-well PCR plates containing 4 μL cell lysis buffer composed by 0.2% Triton X-100, 2 U/μL of recombinant RNase inhibitor (Clontech/Takara), 5 mM dNTP mix (Life Technologies). The sort stream was calibrated carefully to ensure that the cells landed in the liquid interface. RNA loss was minimized by performing on-plate RNA reverse-transcription and whole transcriptome amplification to generate ~1-10 ng of cDNA. Briefly, mRNA was captured using poly-dT oligos and directly reverse-transcribed into full-length double stranded cDNA using the described template-switching LNA oligo (Picelli et al. (2013) *Nat. Methods*). Whole transcriptome cDNA was amplified by PCR for 24 cycles and purified using AMPure XP magnetic bead solution (0.9:1 (vol:vol) ratio, Beckman Coulter) twice. The number of PCR cycles for optimal cDNA amplification was determined by qPCR. Quality and quantity of cDNA amplification were assessed by Fragment Analyzer (Advance Analytical) and fluorescent dsDNA intercalating-dye based assay (Picogreen, Invitrogen). Samples that failed quality control steps as described (Rosales et al. (2018)*Methods Mol. Biol.*) were eliminated from downstream steps. Standard qPCR was performed for housekeeping genes to ensure comparable amplification of all single-cell samples. 0.4 ng of cDNA was used to prepare a standard Nextera XT sequencing library (NextEra XT DNA library prep kit and index kits; Illumina), using an automated platform (Biomek FXp, Beckman Coulter). Before sequencing, all libraries were purified using AMPure XP beads and quality control steps performed as listed previously. Samples that passed strict quality controls were pooled at equimolar concentration, loaded on flow cells and sequenced on the Illumina Sequencing platform, HiSeq2500 (Illumina). Libraries were sequenced to obtain more than 0.3 million 150×150 bp paired-end reads (HiSeq Rapid Run PE Cluster and SBS Kit V2; Illumina) mapping uniquely to mRNA reference.

Statistical Analysis

Statistical analysis was performed using Prism 5 (GraphPad, La Jolla, CA). One-way ANOVA and unpaired two-tailed t-tests were conducted and considered statistically significant at p-values≤0.05 (*), 0.01 () and 0.001 (*).

Example 2. Variant Classifications and Ranking

With respect to an aspect of the methods described herein, all variants are assigned an evidence code from 0 through 4, indicating the level of confidence that the given variant is somatic and expressed at a reasonable level. In the output files, this will be found in the column called 'max evidence threshold'. The filters and classifications are as follows:

Level 0—all reported variants
freq threshold: 0.02
Any variants reported by the initial pass through Freebayes will be assigned at least level 0. This is meant as a catch-all and variants with a frequency of at least 0.02 in the tumor sample will be reported here.

Level 1—loosely somatic
min_ssc: 0
All variants that meet the criteria for level 0, plus have a minimum SSC of 0 will be in this category. The is a log-odds sum with a higher score indicating that the variant is more likely associated with the tumor than the normal sample. The recommended cutoff is 6 as described here. However, this is a loose cutoff of 0 as additional filters are applied in level 3 to ensure confidence in tumor association.

Level 2—nonsynonymous
hgvs_protein !=' '
protein ref !=protein_alt
All variants that meet the criteria for level 1, and are nonsynonymous will make it through this filter. The term "nonsynonymous" is defined as those variants that result in a change at the protein level, as reported by SNPEff in the "hgvs_protein' annotation and that the protein reference sequence (proteinref) is different from the alternate sequence (proteinalt).

Level 3—confident variant call and strong somatic evidence
min_depth: 10
min_nrm_depth: 10
min_tum_alt_freq: 0.05
max_nrm_freq: 0.05
min_tum2nrm_alt_freq_min_to_CI_ratio: 1
critical_ratio_fold_difference: 20
Variants that meet the criteria for level 2 and have additional evidence that the variant is real and tumor-associated will pass these filters. The depth filters ensure a position is reasonably covered to make a variant call. The min_tum_alt_freq ensures that the SNP is present at reasonable levels in the tumor sample, while the max_nrm_alt_freq ensures it is present at low levels in the normal sample. If the tumor purity is known, the min_tum_alt_freq filter can be adjusted accordingly.

tum2nrm_alt_freq_min_to_max_CI_ratio and the critical_ratio

These last two filters ensure that the frequency of the SNP in the tumor sample is greater the frequency of the SNP in the normal sample.

This is the ratio of the tum alt_freq_min_CI (the 95% confidence interval for the lower bound of the frequency in the tumor sample) to the nrm_alt_freq_max_CI (the 95% confidence interval for the upper bound of the SNP frequency in the normal sample). Setting the minimum for this ratio to 1 ensures 95% confidence that the frequency of the SNP in the tumor sample is greater than that of the normal sample.

In addition to this minimum of 1, we also define the 'critical ratio'. This is the theoretical tum2nrm_alt_freq_min_to_max_CI_ratio calculated at the actual tumor and normal depths for the given SNP, if the frequencies were 20% (or whatever is defined as the 'critical ratio fold difference' and 1%, respectively. The tum2nrm_alt_freq_min_to_max_CI_ratio must also be greater than this value to make it to level 3.

Level 4—observed in RNA min_rma_alt_obs: 1

Variants that make it through to this level have passed all filters for level 3 and have been observed in the tumor RNA at least once.

Variant Sorting

All variant and peptide output files are sorted/ranked using the following criteria:

Max. evidence threshold (descending order)

RNA_alt_freq_min_CI (descending order)—the 95% CI lower bound of expression in the tumor RNA.

tum2nrm_alt_freq_ratio (descending order)—the ratio of the alternate frequency in the tumor to that of the normal exome sample. This is calculated by adding a pseudocount of 1 to the alt_obs and a pseudocount of 2 to the depth.

gene TPM (descending order)—the TPM of the gene in which the SNP occurs.

Tumor genotype rank (ascending order)—A rank is assigned to the various genotype calls made by Freebayes. Homozygous for the SNP (1/1) gets the best rank (1), while homozygous for the reference allele (0/0) gets the wort rank (6). Intermediate genotypes fall somewhere in between.

Example 3. Mutanome Pipeline

With respect to an aspect of the methods described herein, the code in this repository has been developed as described herein. Given a certain run configuration file that defines the inputs (normal & tumor exome fastqs, tumor RNA fastqs, etc.), it will validate all inputs and run the samples through the mutanome pipeline, ultimately generating a ranked list of peptides as output.

Input

The only input necessary for running the pipeline is the run configuration file, which specifies the patient_id and fastq files for each sample, including paths & MD5SUMs.

Config File Parameters

Parameters with meanings that are not obvious are described here:

SKIP_FASTQ_READ_COUNTS—By default, the run will die before it gets started if the read counts are not above the limits set in the pipeline config file. Setting this value to '1' will prevent this from occurring and only a Warning message will be printed in the summary report.

Running the Pipeline

To start a pipeline run, it is recommended to run a 'screen' session on a login node. Then, issue the command: perl run_pipeline.pl CONFIG_FILE Output will be printed to the terminal and also captured in a temporary log file. The name of the file will be printed as one of the first outputs on the screen. At the end of the run, this fill will be moved into the pipeline output folder and renamed to 'main.log'.

Configuring the Run Database

A 'run log' database called 'run_log.sqlite' must exist one level up from the base output directory, specified in the config file as, e.g.: base_output_dir: /path/to/pipeline_output If no such file exists, it can be created with the run_log_schema.sgl file as follows: sqlite3 /path/to/pipeline-e_output/../run_log.sqlite <db/run_log_schema.sql This file must have privileges set so that all users that will be running the pipeline are able to read & write.

The Pipeline Workflow

The overall workflow for the pipeline code is: run validation on various inputs; create shell scripts to execute each step; submit the shell scripts to the cluster; monitor for job completion/failures; and summarize output.

Directory Structure

Top Level Directories and Files

'Test' and 'production' runs will save output to different directories. Each type of run will have the following 'ROOT' directory:

production: /mnt/turnstone test (interactive): /mnt/BioAdHoc/Groups/core/pipeline_development/turnstone test (automated):/mnt/BioAdHoc/Groups/core/pipeline_development/gitlab-runner/turnst one The toplevel directory will generally look like:

all_runs_status.html
pipeline_runs/
raw_data/
run log.sqlite

Run-Level Directories and Files

Each pipeline run directory contains several subdirectories, one corresponding to each step that is run and prefixed with a zero-padded number that indicates the order in which the step was run. The toplevel directory of a typical run will look similar to below when the run is complete (trailing '/' indicates a directory):

001-exome-merge-fastq/
002-exome-run-speedseq/
003-exome-extract-data/
004-rnaseq-merge_fastq/
005-rnaseq_align/
006-rnaseq_count/
007-rnaseq_TPM/
008_rnaseq_prepare_bams/
009_rnaseq compare variants/
010_load_database/
_peptide_generation/
_igv_session/
all_params_post_run.json all_params_pre_run.json
    pipeline_config.yaml
    run_config.yaml
    run_status.html
    scratch/
    summaryhtml Validations The following validations are run before the pipeline creates the shell scripts. Should any of these validations fail, the pipeline will exit with an error code and update the run status in the run database.

run config filename: Config filename is in expected format.

patient ID exists: Check that the patient ID exists in the patient database.

patient run ID is new: This run ID for this patient has not been previously run.

patient run ID in order: The patient run ID is in the expected order.

missing run parameters: All expected parameters in the run config file are present.

missing input files: All input files exist and are readable by the current user.

free space is sufficient: Check that there is at least 1 TB of free space on the output volume.

fastq md5s match expectation: The fastqs specified in the config file have MD5SUMs that match what is specified.

fastq header format is known: The fastq headers are in the expected format.

minimum reads: More than the minimum number of reads are present.

Create the Shell Scripts and Submit the Jobs

After the validations have completed (and passed), the output directory structure for the run and its shell scripts are created. Each step directory will have a file called run_step.sh that includes the code for the run and will get submitted to the cluster.

Once all shell scripts are successfully created, each job will be submitted to the cluster with a call to qsub. The job ID for each step is recorded and is specified as a dependency for the next downstream step. For example, if the 001 exome_merge_fastq step is submitted and becomes job ID 100, the next step 002_exome_run_speedseq will be submitted with a dependency on job ID 100 and will not run until this job completes.

Expected Output Files

Expected output files can be specified for each step by creating an 'expected_outputs' property on the step. This is a hashref, keyed by a unique name for the output. The contents include the 'path' to the file (required) and several optional parameters, including but not limited to min_lines; min_MB; and descr.0

Figure 1B:
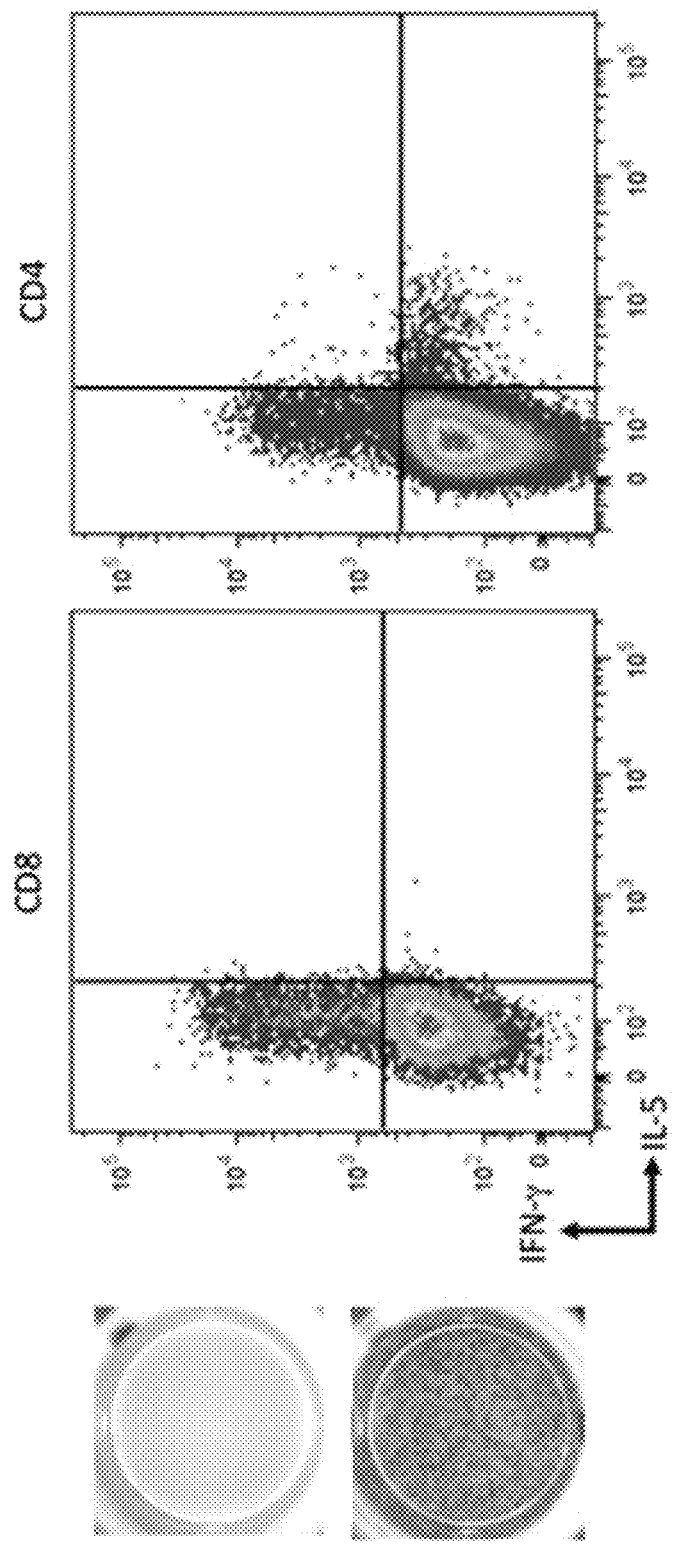

Example 4. Tumor Neoantigens can be Identified Using a Functional Approach to Detection and Validation that Excludes in Silico Epitope Binding Predictions To identify candidate neoantigens in patients with low mutational burden malignancies, a functional neoantigen identification pipeline that eliminates in silico epitope binding prediction was developed (see: FIGS. 1A-B). As shown in FIGS. 1A-B, the functional neoantigen identification pipeline starts with tumor and autologous cells being obtained from a subject. The cells from the subject are then sequenced to identify the transcriptome of both tumor cells and normal cells from the subject. One or more bioinformatics steps, as described herein, are then applied to the tumor cell and normal cell transcriptomes to detect tumor-expressed (somatic), tumor-specific, protein-changing (non-synonymous) mutations, which are then expressed as peptides (e.g., 20-mers; and including synthetic peptides in certain embodiments) and subjected to immunological analysis or screening to identify immunostimulatory peptides, thereby identifying neoantigens.

An exemplary, illustrative application of the functional neoantigen identification pipeline follows. One skilled in the art will recognize that this general methodology may be applied to a variety of tumors and subjects and that the following is illustrative of a methodology, with appropriate adjustment based on the subject(s) and/or tumor(s), that may have general application.

Figure 2A:
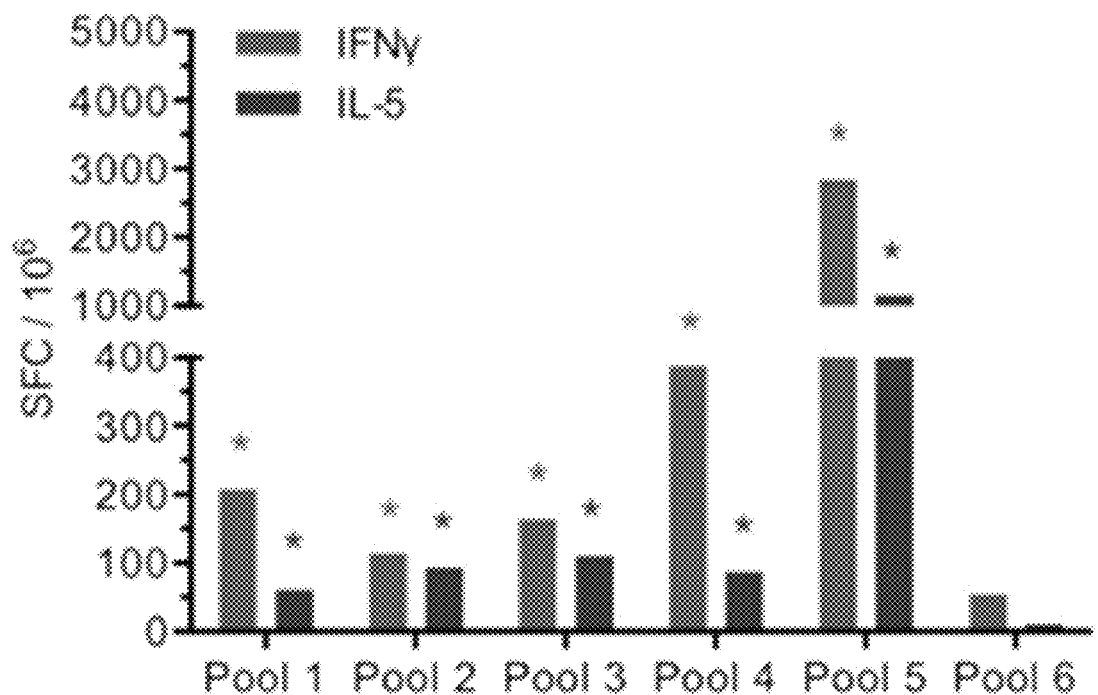
Figure 2B:
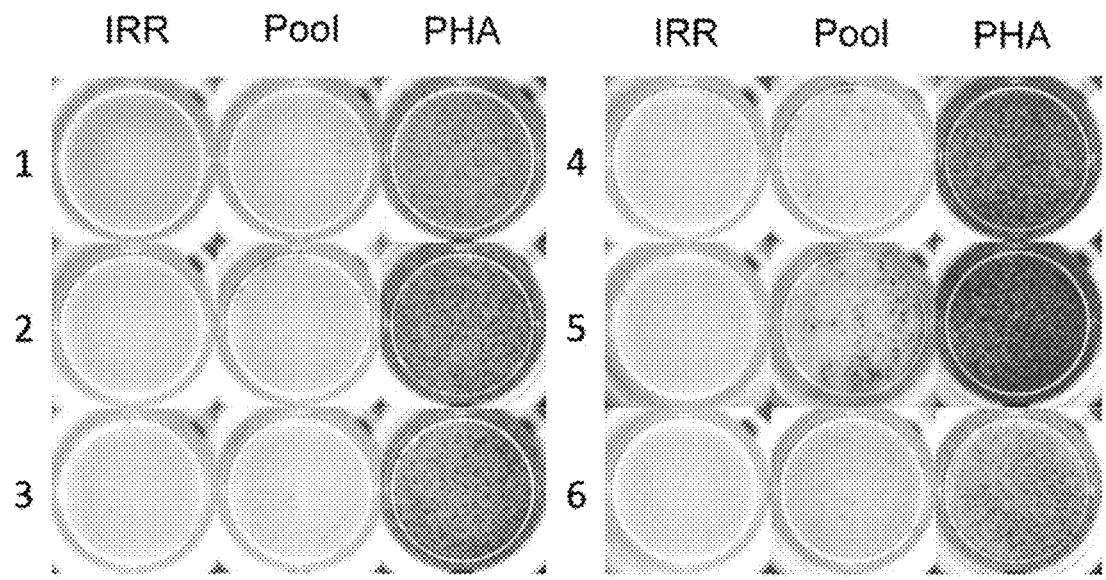
Figure 3A:
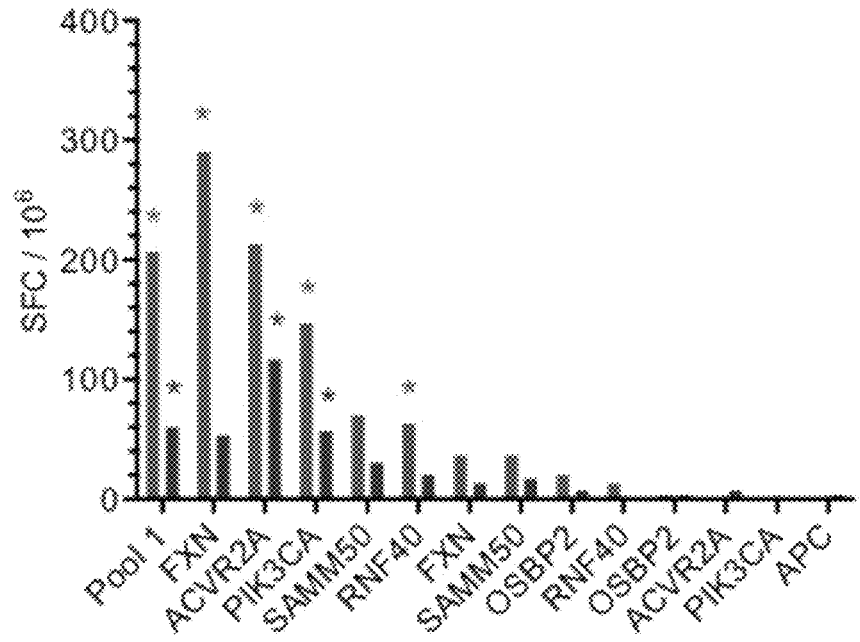
Figure 3A:
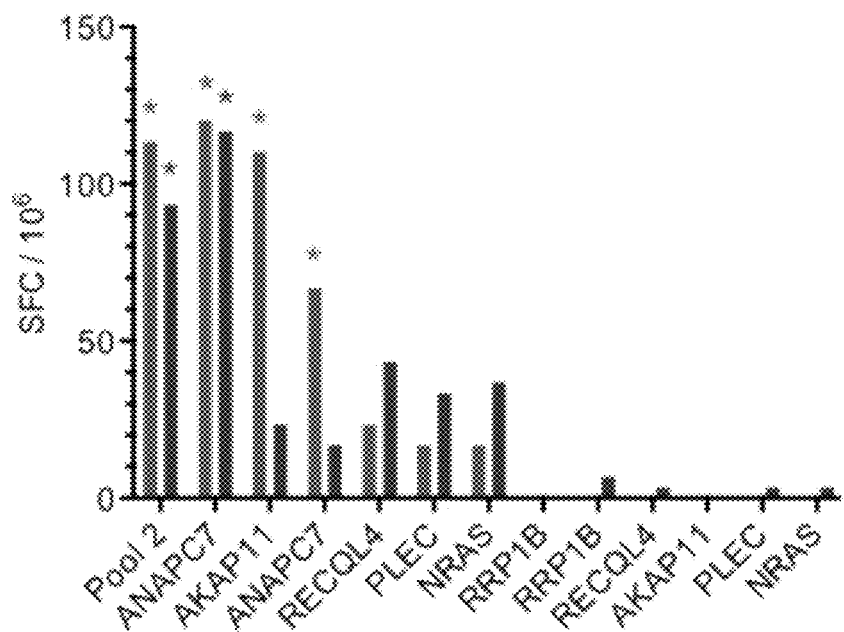
Figure 3B:
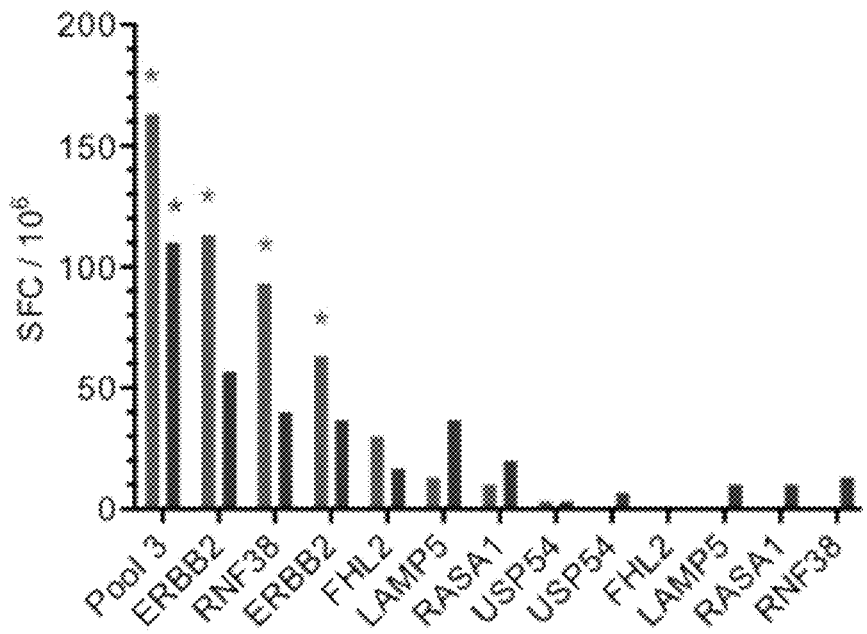
Figure 3B:
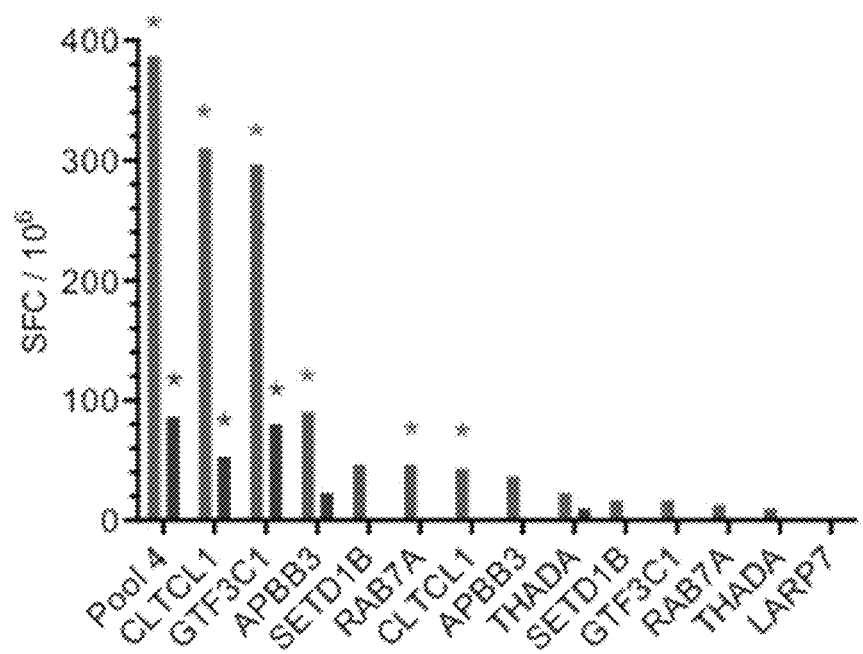
Figure 3C:
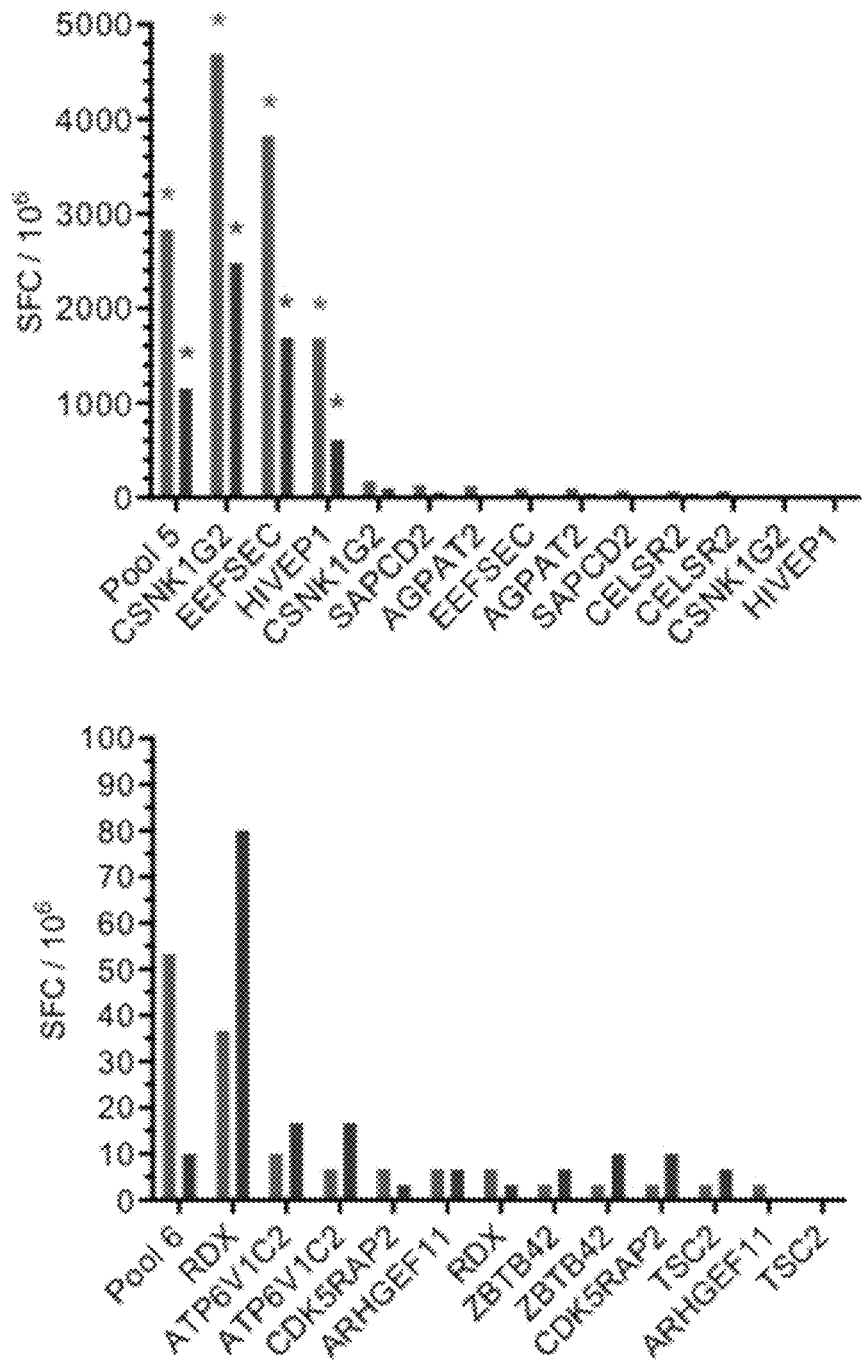
Figure 4A:
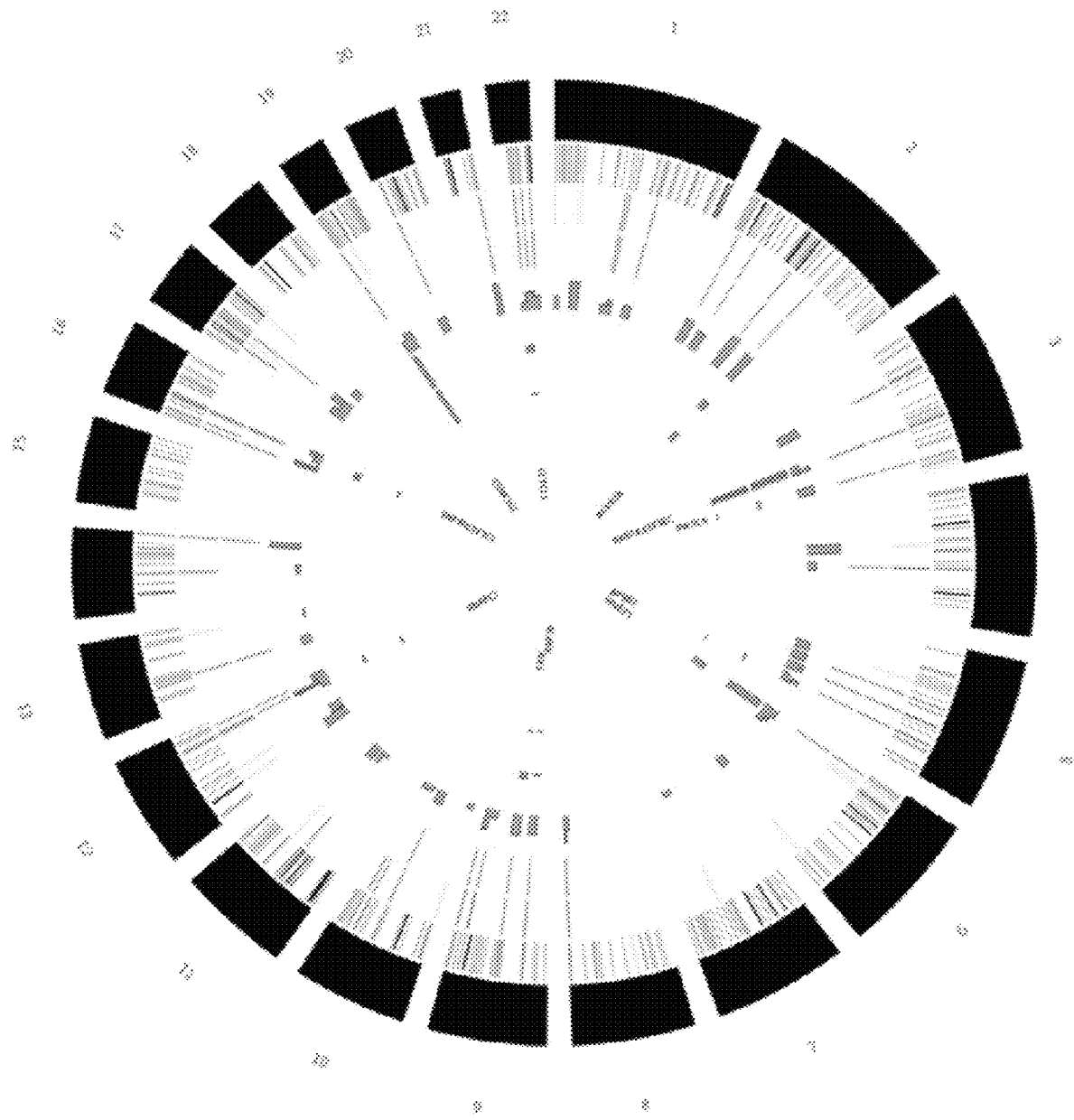
Figure 4B:
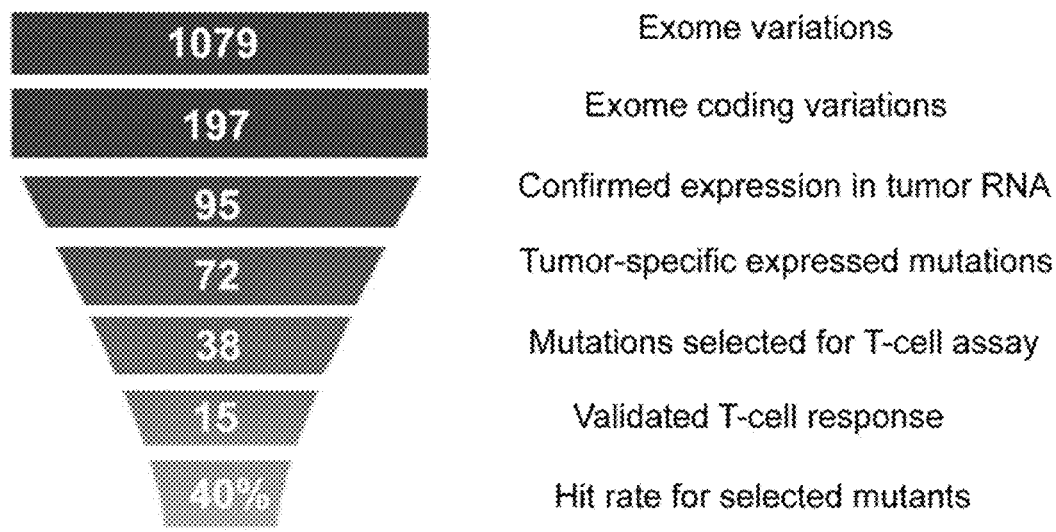

Nucleic acid extraction from fresh frozen tumor specimens with concomitant extraction of nucleic acids from peripheral blood mononuclear cells (PBMC) as the reference genome for each patient. Whole exome sequencing (WES) was performed on the tumor and PBMC DNA at a read depth of 50-100× along with tandem RNAseq on the tumor RNA with a minimum of $5 \times 10^7$ reads. This WES/RNAseq approach identified tumor-specific non-synonymous mutations that are expressed in the transcriptome of the tumor. Those tumor-specific mutations with a minimum of 10 reads and frequency of the mutation of >20% of the total reads were then synthesized into two 20-mer peptides with the mutation at position 6 and position 15 and subjected to a 14-day co-culture with autologous PBMC followed by ELISPOT assays for IFN-γ and IL-5 production in response to the mutant peptides to determine the immunogenicity of the candidate peptides. For example, tumor tissue acquired from a patient with metastatic microsatellite-stable colorectal cancer (MSS-mCRC), PT-37 (Hu_037), and identified 1,079 exome variants with 197 confirmed to be coding variants and 72 shown to be detectable in tumor RNA. Of these 72 candidates, 38 were selected for immunogenicity testing in ELSIPOT assays based on the read depth and variant allele expression frequency in the tumor tissue. Peptide pools consisting of 8-10 20-mer candidate peptides were then co-cultured with autologous PBMC for 14 days prior to performing IFN-γ and IL-5 ELISPOT assays using irrelevant peptide and PHA as negative and positive controls. For PT-37, five of the six peptide pools elicited autologous T-cell responses, including responses of both Th1 and Th2 polarity (see: FIGS. 2A and 2B). De-convolution of the pool responses to single peptides showed that 15 of the 38 neoantigen candidates identified by the neoantigen identification pipeline method stimulated T cell responses (see: FIGS. 3A-C). These included responses against NRAS Q61R, ERBB2 R46Q and PIK3CA E542K mutant peptides. Remarkably, 40% of the candidate neoantigens stimulated T-cell responses as shown in FIGS. 4A-B.

Example 5. Neoantigens are Detected and Identified at High Efficiency in Low Mutational Burden Malignancies Using the Functional Identification Pipeline The functional neoantigen identification pipeline was next applied to eight (8) additional patients with low mutational burden malignancies, including pancreatic neuroendocrine carcinoma (PT-48 (Hu_048)), head and neck squamous cells carcinoma (PT-56 (Hu_056)) and pancreatic adenocarcinoma (PT-159 (Hu_159)) to determine the reproducibility of this approach at identifying T cell responses to candidate neoantigens in a broader population of patients. As shown in Table 1, the functional neoantigen identification approach successfully identified T cell responses to 19-77% of the candidate neoantigens selected for testing (see: Table 1 and Table 2, which shows the results from one patient, which were excluded from Table 1, because no mutations met the predetermined RNA criteria, though they were tested for T-cell response). The total number of somatic mutations in these patients ranged from 438 to 3326 mutations, thus highlighting the sensitivity of this approach in detecting biologically relevant neoantigens. In addition, the neoantigen identification pipeline detected T-cells polarized to produce both Th2 (IL-5) and Th1 (IFN-γ) cytokines, whereas most existing methods of neoantigen identification and discovery are biased toward the identification of Th1 responses. Finally, the neoantigen identification pipeline identified functional T-cell responses against driver mutations in TP53, APC, RB1, PIK3CA, NRAS, ERBB2, KRAS and MEN1, which represent attractive targets for T cell directed therapies due to their critical roles in cancer pathogenesis. For two of the patients (PT-37 (Hu_037) and PT-48 (Hu_048)), expression of immunogenic neoantigens was detected in the tumor RNA from spatially distinct sites of disease and serve as ideal therapeutic targets due to their conserved expression across sites of disease.

Figure 5A:
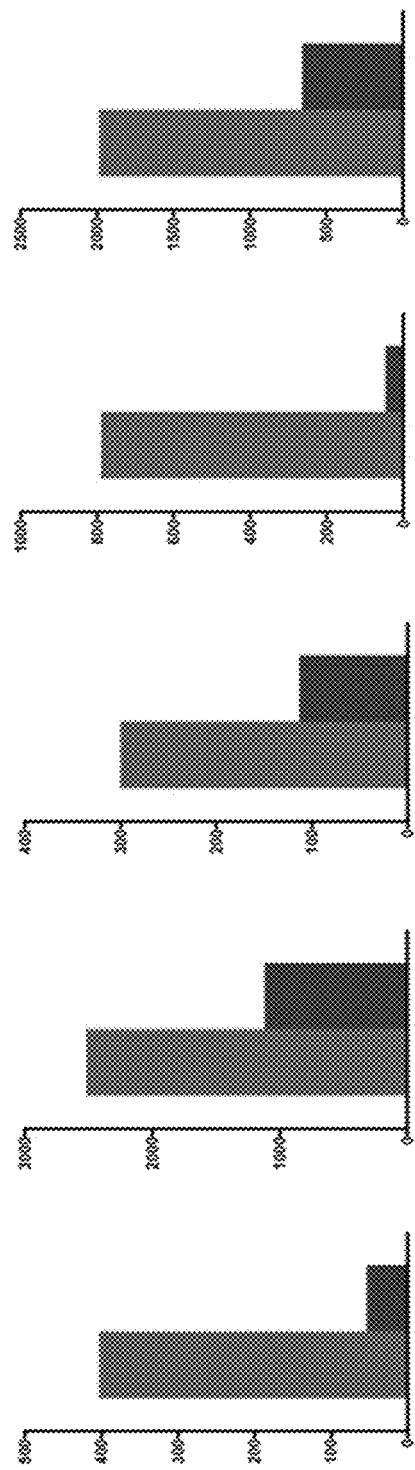
FIGS. 5A-D depict results of ELISPOT assays. More specifically.
Figure 5B:
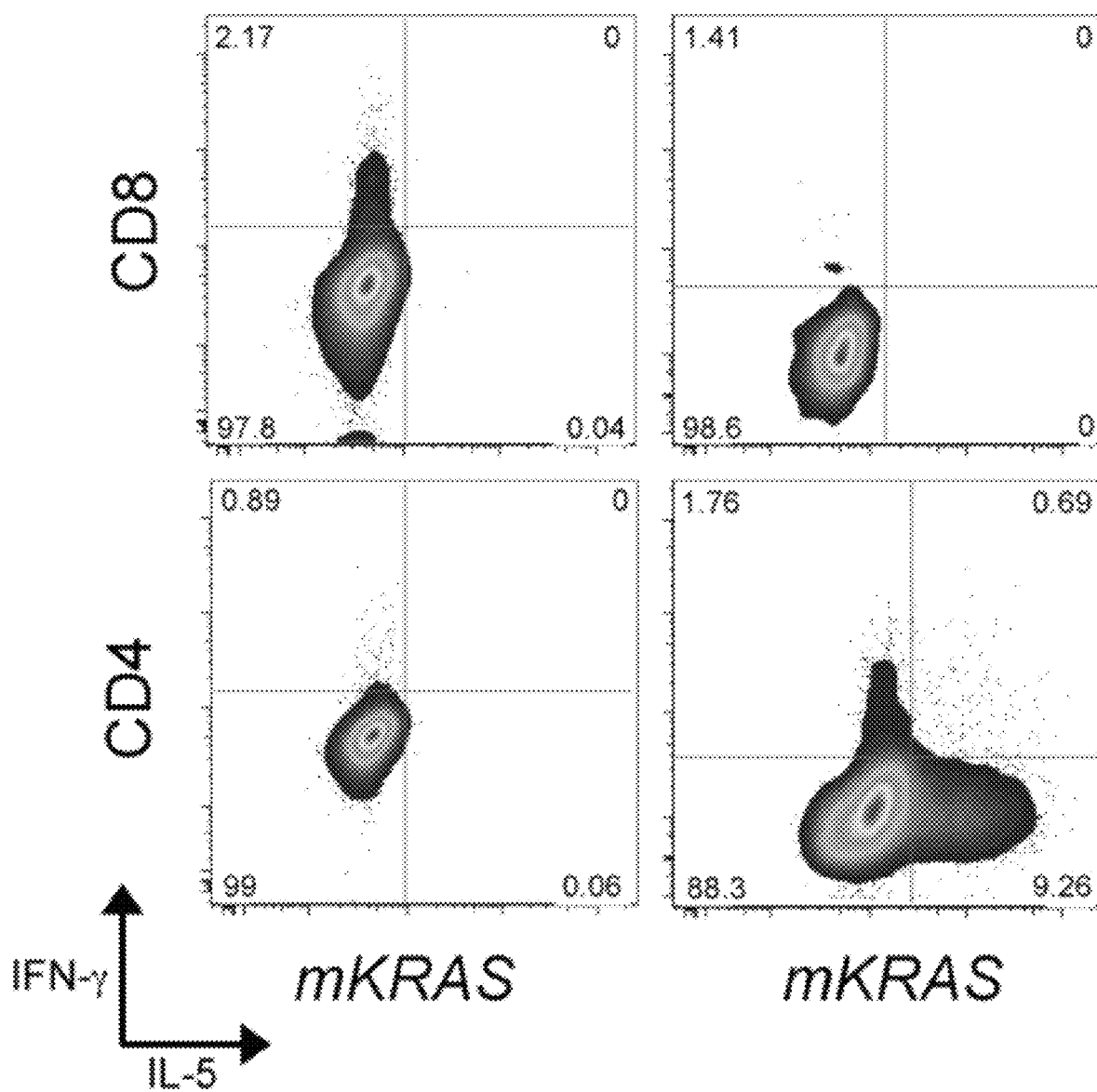
Figure 5C:
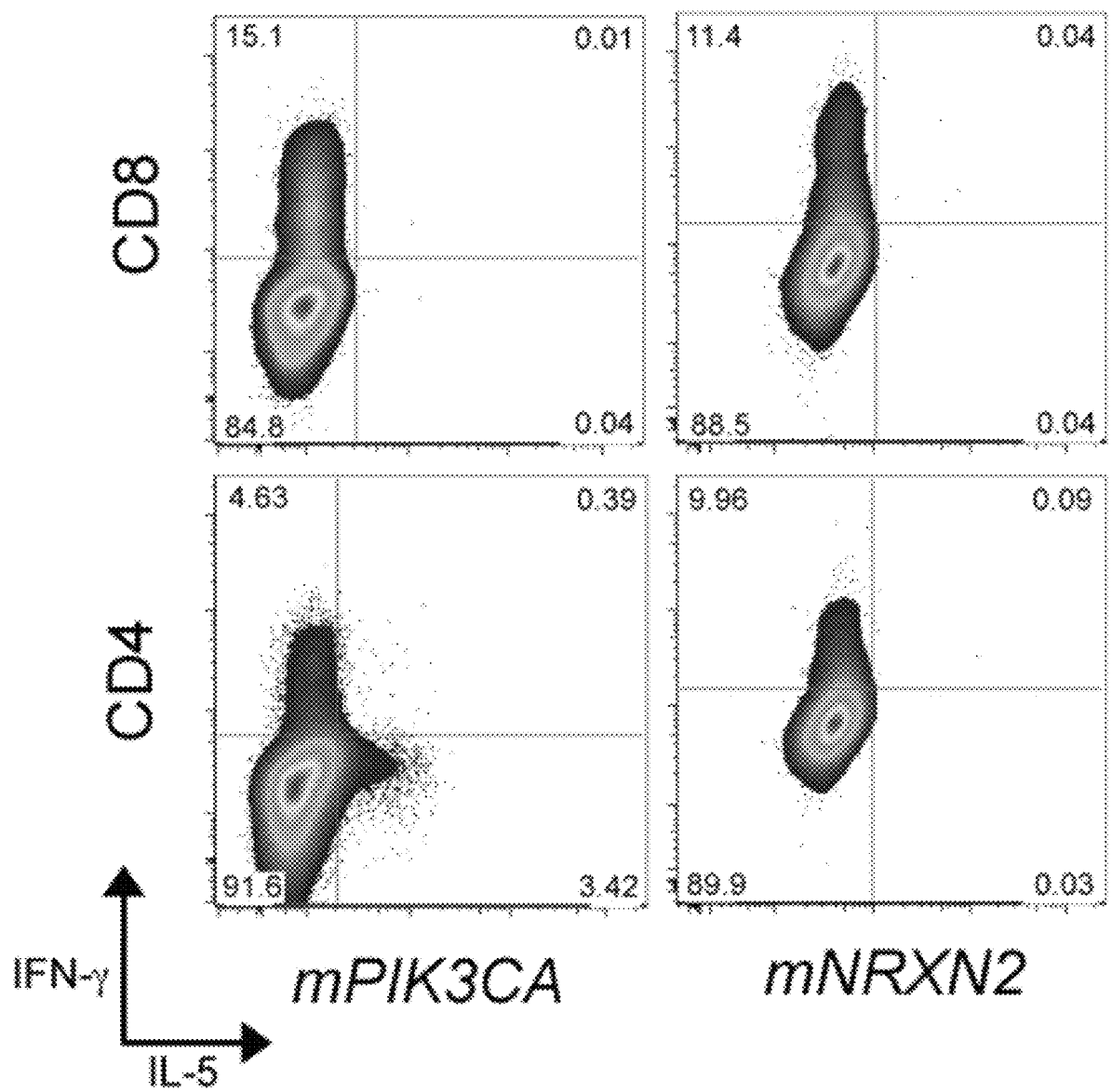
Figure 5D:
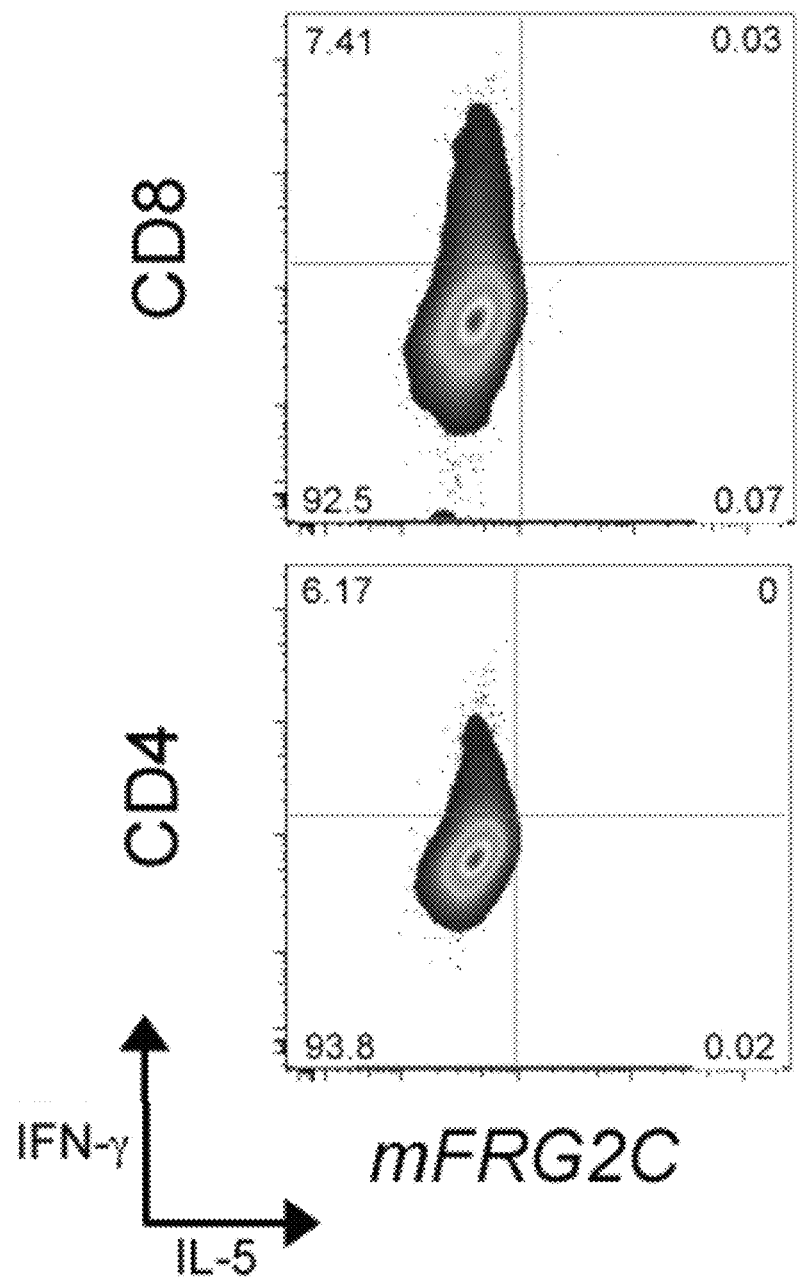

Example 6. The Functional Neoantigen Identification Pipeline can be Used to Identify MHC Class I Neoantigens, Class II Neoantigens, or Both The foregoing results demonstrate the immunogenicity of candidate neoantigens by ELISPOT. The functional neoantigen identification pipeline can also delineate CD4- and CD8-specific responses against candidate neoantigens using cytokine secretion assays. For these experiments, T-cells derived from peripheral blood were subjected to a 14-day co-culture with pools of candidate neoantigen peptides and subsequently re-stimulated on day 17 with the mutant neoantigen peptides that were shown to be immunogenic on the day 14 ELSIPOT. Briefly, cells were labeled with both IFN-γ and IL-5 cytokine capture antibodies, along with CD4 and CD8 surface staining, and the amplitude of effector cytokine release from these T cell subsets was determined following a 3-h incubation with mutant peptide (neoantigens). For example, ELISPOT assays identified functional T cell responses against the driver mutations KRAS G12V and passenger mutations NRXN2 R861 W and FRG2C Ni 19S (FIGS. 5A-D). Re-stimulation of T cells from the 14-day co-culture with single mutant peptides on day 17 discerned distinct populations of CD8 and CD4 T cells producing IFN-γ and IL-5 that correlate with the ELISPOT results (FIGS. 5B-D, and as shown in FIG. 5A, which shows IFN-γ (left) and IL-5 (right) levels).

TABLE 1

The functional neoantigen identification pipeline successfully identified T-cell responses to 19-77% of the candidate neoantigens selected for testing

| Patient | A | B | C | D | E | F | G | H | I | J | K | L |
|---|---|---|---|---|---|---|---|---|---|---|---|---|
| Hu_195 | 67 | 20 | 30% | 139 | 27 | 112 | 19% | 12 | 15 | 0 | 5500 | 371 |
| Hu_250 | 3 | 2 | 67% | 9 | 3 | 6 | 33% | 3 | 0 | 0 | 354 | 25 |
| Hu_254 | 23 | 10 | 43% | 51 | 12 | 39 | 24% | 1 | 10 | 1 | 1898 | 217 |
| Hu_060 | 5 | 5 | 100% | 13 | 10 | 3 | 77% | 4 | 5 | 1 | 474 | 73 |
| Hu_159 | 4 | 3 | 75% | 11 | 4 | 7 | 36% | 3 | 1 | 0 | 414 | 15 |
| Hu_006 | 20 | 7 | 35% | 41 | 8 | 33 | 20% | 3 | 2 | 3 | 1652 | 154 |
| Hu_037 | 32 | 14 | 44% | 64 | 16 | 48 | 25% | 6 | 10 | 0 | 2604 | 235 |
| Hu_048 | 3 | 2 | 67% | 6 | 2 | 4 | 33% | 1 | 0 | 1 | 246 | 13 |
| Hu_056 | 7 | 7 | 100% | 14 | 8 | 6 | 57% | 2 | 6 | 0 | 566 | 56 |
| Total | 164 | 70 | 43% | 348 | 90 | 258 | 36% | 35 | 49 | 6 | 13708 | 1159 |

TABLE 2

Tested but excluded, because no mutations met RNA criteria

| Patient | A | B | C | D | E | F | G | H | I | J | K | L |
|---|---|---|---|---|---|---|---|---|---|---|---|---|
| Hu_150 | 0 | 0 | 0% | 0 | 0 | 0 | 0% | 0 | 0 | 0 | 0 | 0 |

Key to Tables 1 and 2:
- A: Number of mutations tested that met predetermined criteria
- B: Number of mutations that had a positive peptide
- C: Percent positive mutations
- D: Number of 20-mers tested that met predetermined criteria
- E: Number of positive 20-mers (any IFN-γ or IL5 response)
- F: Number of negative 20-mers
- G: Hit Rate
- H: Number of 20-mers with both IFN-γ and IL5
- I: Number of 20-mers with IFN-γ only
- J: Number of 20-mers with IL5 only
- K: Number of short peptides (8-11-mers) that span a mutation
- L: Number of short peptides predicted binders

Figure 6A:
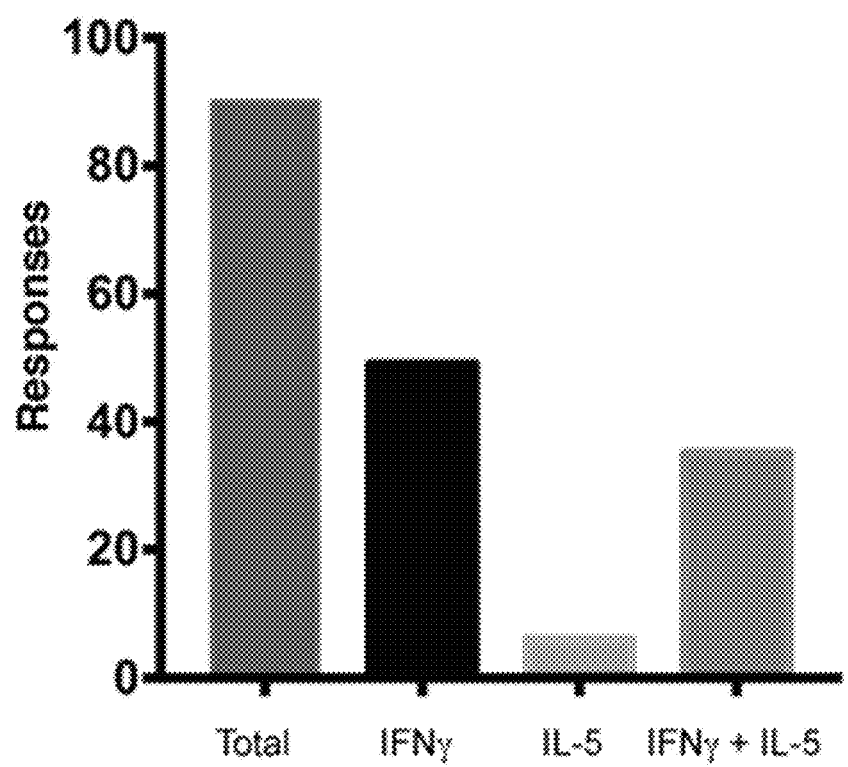
FIGS. 6A and 6B depict a comparison between the neoantigen pipeline methods described herein as compared to conventional in silico prediction algorithms. As detailed herein, for the nine patients includes in this study, 164 non-synonymous somatic mutations expressed in the tumor RNA were identified and selected for immunogenicity testing based on their read depth and variant allele frequency. A total of 348 20-mer mutant peptides were synthesized for ELISPOT assays and 92 (36%) were shown to be immunogenic, as shown in FIG. 6A. Further, and as detailed herein, of the 49 peptides shown to have IFN-γ specific responses by ELISPOT, twelve (25%) would not have been identified by conventional in silico prediction since their predicted binding affinity was >500 nM, as shown in FIG. 6B.

Example 7. The Functional Neoantigen Identification Pipeline Detects Immunogenic Neoepitopes that Conventional Epitope Prediction Models Fail to Identify and Requires Screening of Fewer Candidate Peptides The functional neoantigen identification pipeline was next compared to conventional in silico prediction algorithms to determine the relative merits of the functional neoantigen pipeline in detecting functionally validated neoantigens. For the nine patients included in this study the neoantigen identification pipeline identified 164 non-synonymous somatic mutations expressed in the tumor RNA that were selected for immunogenicity testing based on their read depth and variant allele frequency. A total of 348 20-mer mutant peptides were synthesized for ELISPOT assays and 92 (hit rate of 36%) of the candidate peptides were shown to be immunogenic (see: FIG. 6A), whereas 256 were negative.

Figure 6B:
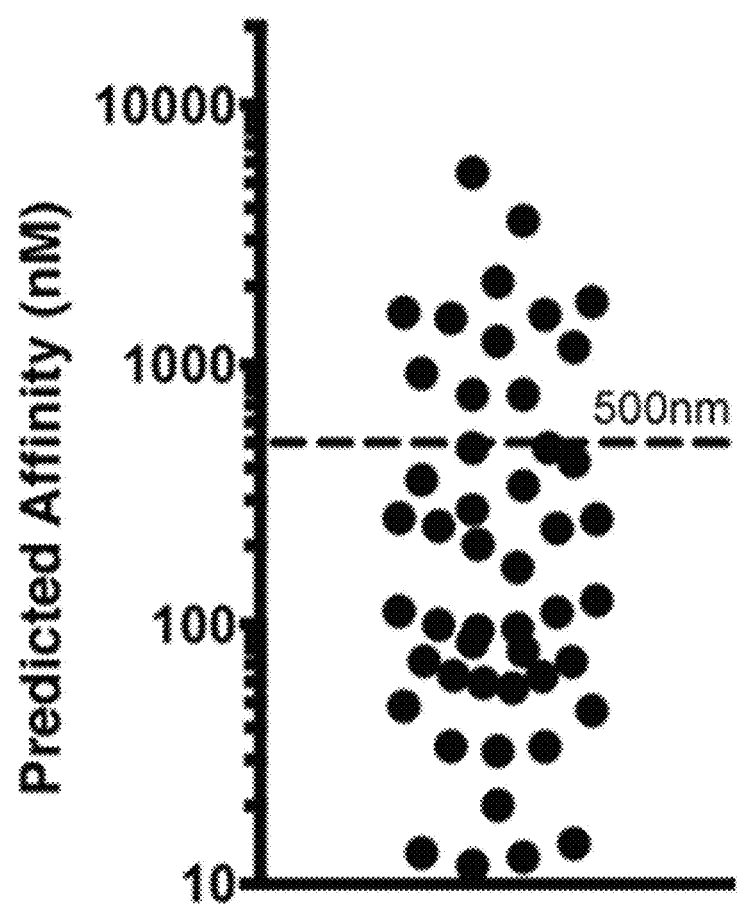

In comparison, conventional epitope prediction using netMHCpan4.0 identified 13,708 short peptides that would need to be synthesized to test these 164 variants with 1,159 peptides exhibiting a predicted binding affinity of <500 nm and/or an MHC class I rank score <2, with a resulting hit rate of about 2%. Accordingly, conventional in silico prediction would require more than three times as many peptides to be synthesized at the <500 nm binding threshold to identify the same immunogenic neoantigens as the functional neoantigen identification pipeline. More importantly, of the 49 peptides shown to have IFN-γ specific responses by ELISPOT, twelve (25%) would not have been identified by conventional in silico prediction since their predicted binding affinity was >500 nM (see: FIG. 6B; Table 3). This suggests that conventional in silico prediction models have a high rate of false negatives in detecting immunogenic neoepitopes. In addition, T-cell responses of both Th1 and Th2 polarity were detected using the neoantigen identification pipeline, as demonstrated by detection of 6 peptides that elicited IL-5 responses and 37 peptides that generated by IFN-γ and IL-5 responses (see: FIG. 6A). Of the peptides that generated IL-5 responses only, 1 had a predicted MHC Class II % Rank of <2 using class II binding algorithms (see: Table 4). This translates to an 83% false negative rate using conventional prediction to identify functionally validated class II neoantigens detected using the functional neoantigen identification pipeline approach to neoantigen identification and discovery.

TABLE 3

Twelve (25%) of 49 peptides shown to have IFN-γ specific responses by ELISPOT would not have been identified by conventional in silico prediction, since their predicted binding affinity was >500 nM

| Mutated 20-mer peptide | IC$_{50}$ | Rank | IC$_{50}$ Class II | Rank Class II |
|---|---|---|---|---|
| LLRHLGLQNRRINLHSHDYG (SEQ ID NO: 16) | 3577.8 | 1.6652 | 339.11 | 5 |
| LASYTYNIEAVSCDEALVDI (SEQ ID NO: 17) | 1165.7 | 0.2086 | 1157.78 | 16 |
| KVTGAGFVVFNGALKTSSGF (SEQ ID NO: 18) | 767 | 1.7432 | 80.79 | 1.3 |
| GQDRPIKTFQGHTNGVNAIK (SEQ ID NO: 19) | 924.2 | 0.9631 | 326.22 | 12 |
| EITAMPCNMNTQCPHGGYCM (SEQ ID NO: 20) | 1506.5 | 1.7362 | 1477.14 | 55 |
| LSPDCLGHAGLVYECTLGEE (SEQ ID NO: 21) | 1584.7 | 1.7915 | 1153.79 | 18 |
| SSGNLPGRNSFEVRVCACPG (SEQ ID NO: 22) | 767.5 | 0.4583 | 920.27 | 38 |
| GEQVLSLKSQVDAQLLTVQK (SEQ ID NO: 23) | 2080.9 | 0.5135 | 144.92 | 5 |
| RRGLRIDIDATCTPRRASSN (SEQ ID NO: 24) | 5475 | 4.9623 | 1084.45 | 24 |
| MAVFADLDLRAGCDLKALRG (SEQ ID NO: 25) | 1742.1 | 1.1331 | 619.32 | 5 |
| DLRAGCDLKALRGLVETAAH (SEQ ID NO: 26) | 1226.7 | 2.7074 | 319.5 | 18 |
| EYDDIPVRSVRVSWRPPADD (SEQ ID NO: 27) | 1556 | 0.2672 | 168.84 | 11 |

TABLE 4

IL-5 only peptides with their predicted MHC Class II IC$_{50}$ and % Rank values.

| Peptide | Predicted MHC Class II IC$_{50}$ | Predicted MHC Class II % Rank |
|---|---|---|
| QLARKMKKEAASLSQWLSAT (SEQ ID NO: 28) | 259.4 | 12 |
| YALQVYCYNSNFPKGMLLRF (SEQ ID NO: 29) | 199.57 | 16 |
| DYRTVSNLILTGPRMIVMEV (SEQ ID NO: 30) | 12.67 | 0.5 |
| APSWPLSSSVPSQKPTRAAT (SEQ ID NO: 31) | 372.68 | 50 |
| VPSQKPTRAATVSVWASCIL (SEQ ID NO: 32) | 278.69 | 11 |
| GPSGQFTHEFDGDEEFYVDL (SEQ ID NO: 33) | 6888.11 | 95 |

Example 8. SCC VII Neoantigen Identification

Figure 11A:
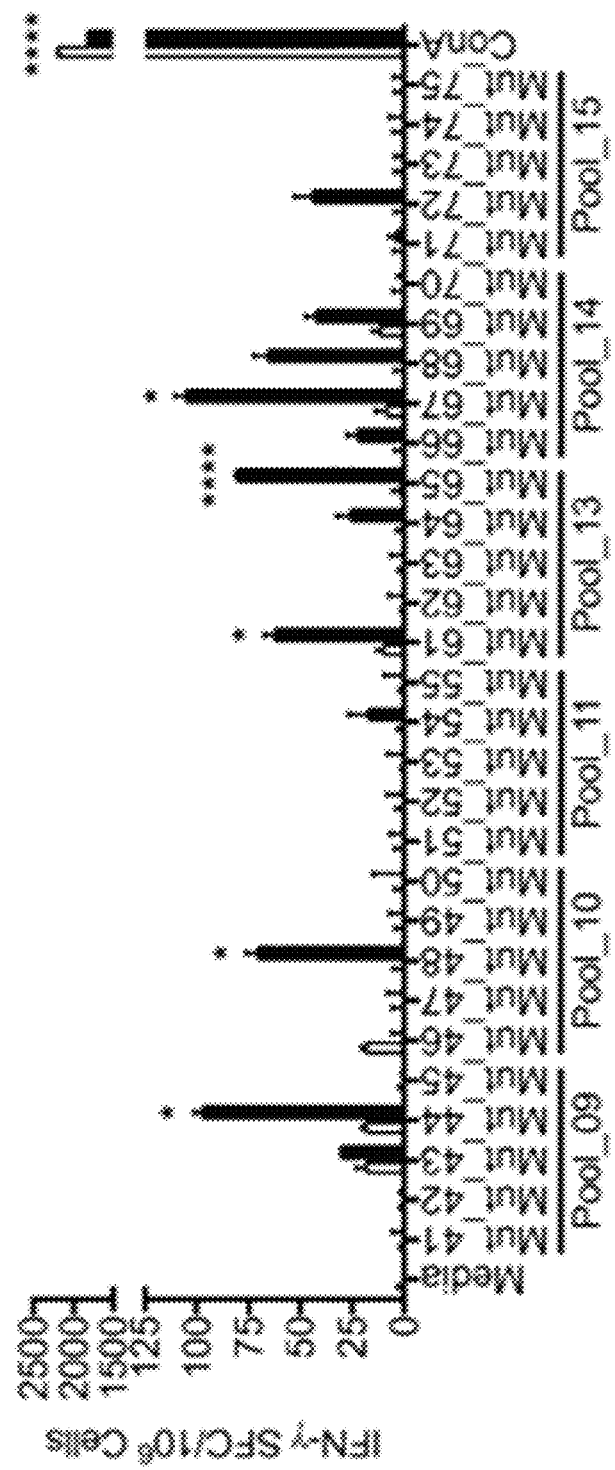
FIGS. 11A and 11B depict SCC VII neoantigen identification results. Specifically.
Figure 11B:
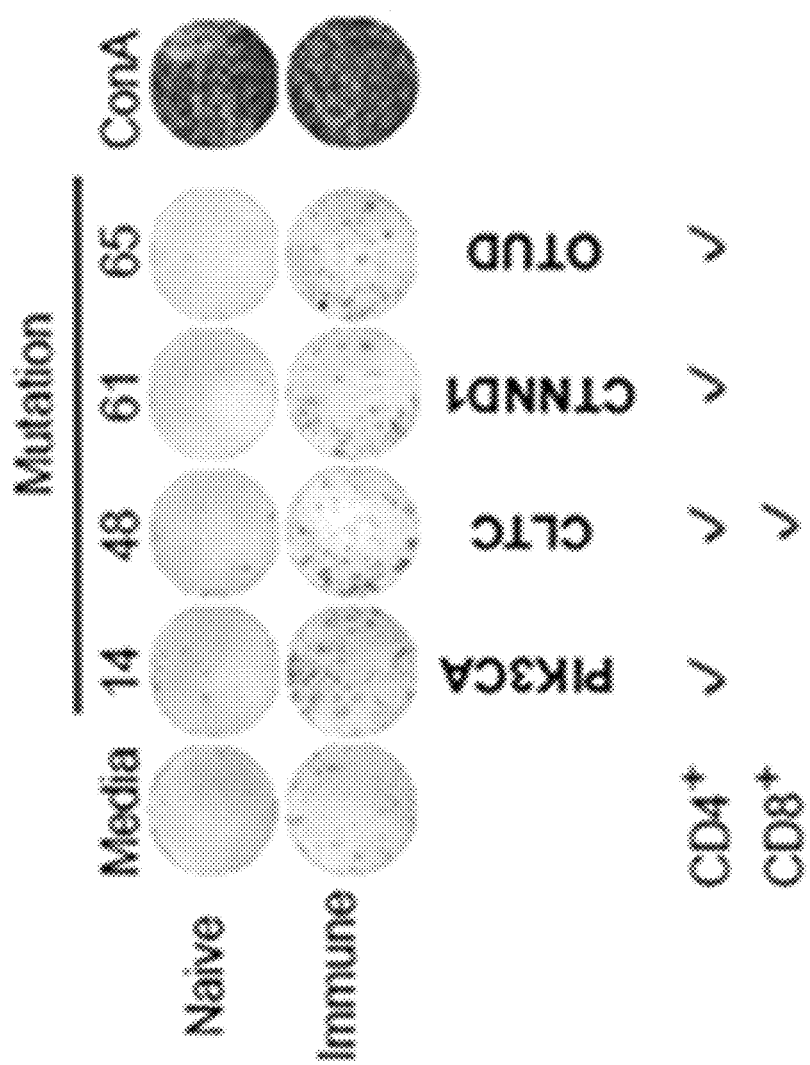

With respect to the data depicted in FIG. 11A and FIG. 11B, SCC VII tumors were isolated from C3H/J mice and subjected to our neoAg identification workflow as described herein; white bar (naïve) and black (immunized, i.e., SCCVII+PolyL:C). With respect to FIG. 11A, candidate 20mer peptides nominated for functional testing were pulsed as pools onto syngeneic DC and used to restimulate splenocytes from tumor-challenged mice one day prior to ELISPOT analysis. With respect to FIG. 11B, positive pools were subsequently deconvoluted into single peptides to reveal the specific mutations comprising the relevant neoAg. Further analysis by CCA revealed the indicated responding T cell subsets for each neoAg. Mut 65 and 67 are variant peptides from the same neoAg (OTUD). Displayed are representative results reported as spot forming cells (SFC) per 106 input cells (n=3 per group). Mean+s.e.m.; *P<0.05, P<0.01, and **P<0.0001 (t test) of data with SI>2 and Poisson<5%.

Example 9. Protection by Neoantigen Peptide Vaccine

Figure 12A:
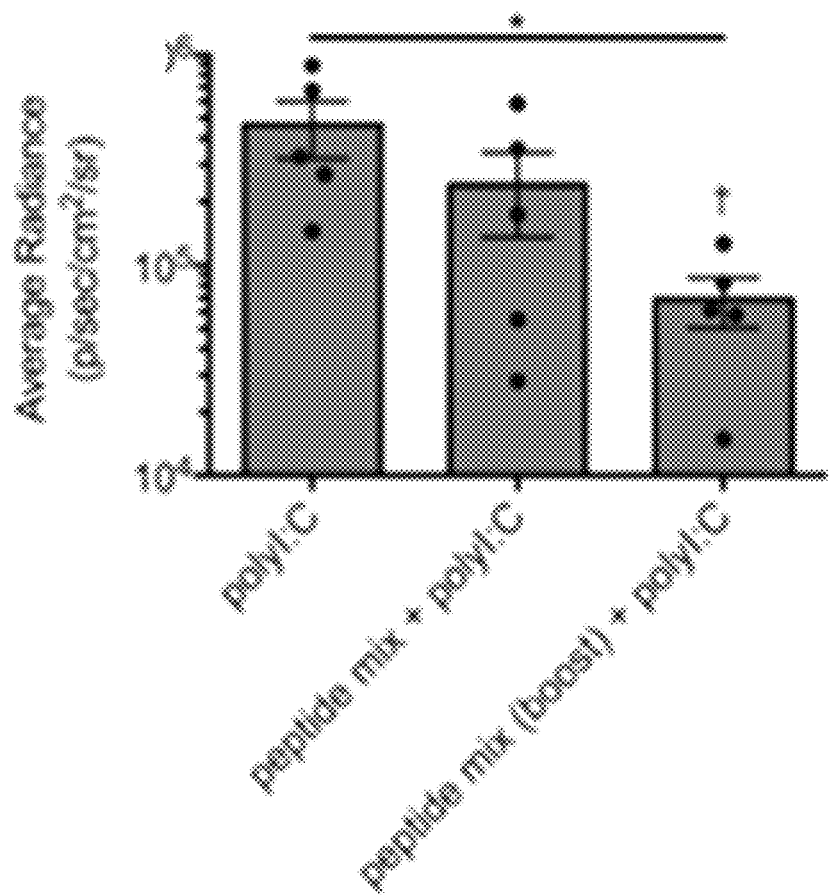
FIGS. 12A and 12B depict results demonstrating neoantigen peptide vaccine efficacy. Specifically.
Figure 12B:
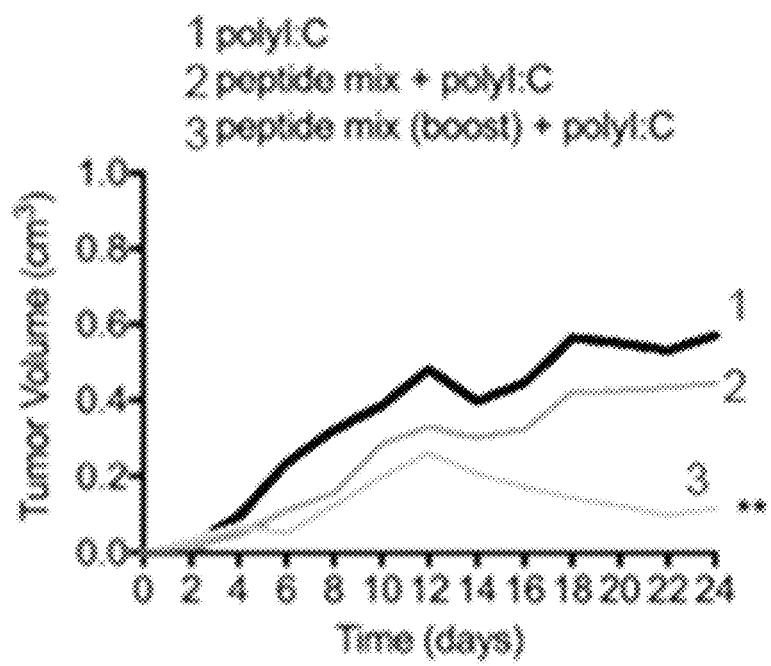

With respect to the data depicted in FIG. 12A and FIG. 12B, groups of C3H/J mice were immunized with the 4 neoAg peptides identified previously (see: FIGS. 11A and 111B) as 20mers at a dose of 5 μg each together with polyI:C (Curve 2) or boosted with the same formulation 14 days later (boost, Curve 3). All mice were the challenged at d28 with 5×10$^6$ live SCC VII cells and tumor growth was monitored by bioluminescence (FIG. 12A) and longitudinally by caliper measurement (FIG. 12B). Mean±s.e.m.; *P<0.05 and P<0.01 (t test); tP<0.05 (one-way ANOVA and Tukey's posttest relative to polyI:C); P<0.01 (two-way ANOVA and Dunnett's posttest relative to polyI:C).

Example 10. ICB Synergizes with Neoantigen Peptide Vaccination

Figure 13A:
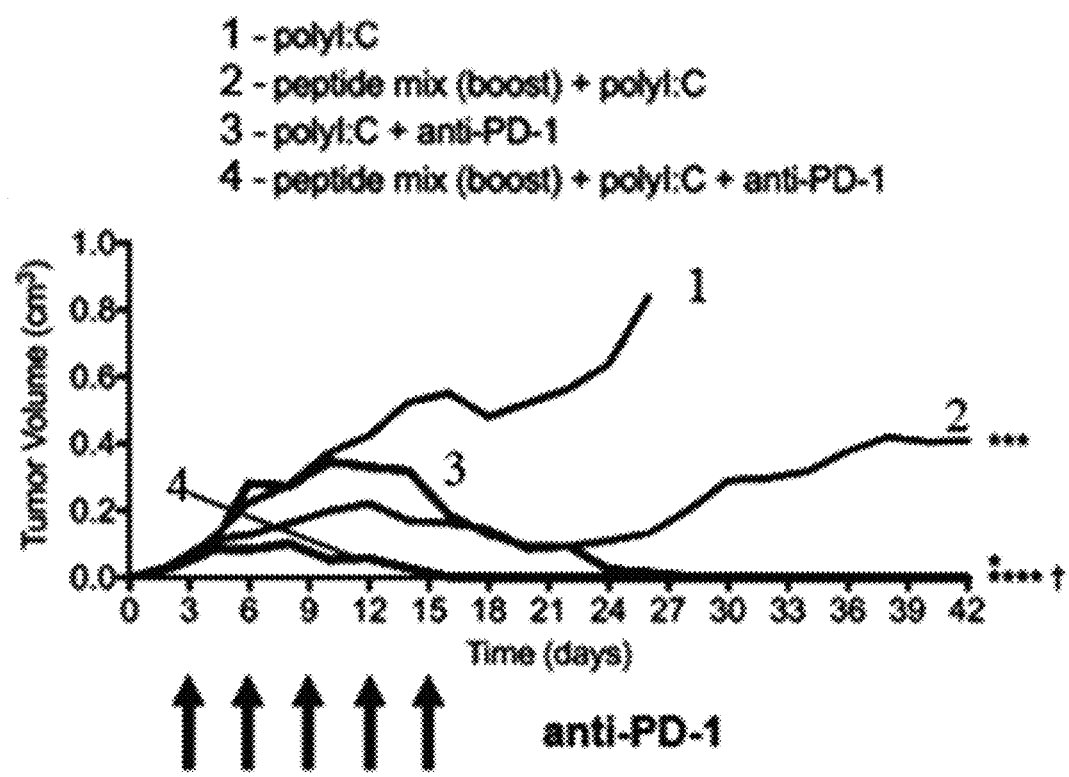
FIGS. 13A and 13B depict results demonstrating that ICB synergizes with neoantigen peptide vaccination. Specifically.
Figure 13B:
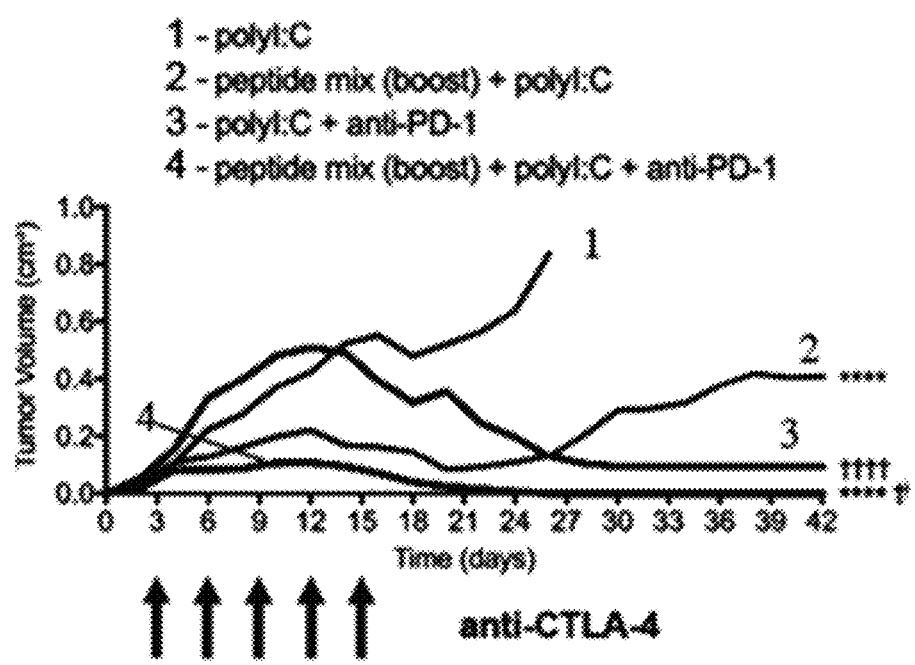

With respect to the data depicted in FIG. 13A and FIG. 13B, groups of C3H/J mice were vaccinated with pooled neoAg 20mer peptides (5 μg/peptide) plus polyI:C as indicated and challenged 14d later with 5×10$^6$ live SCC VII tumor cells. Beginning at 3d post-challenge, mice were treated every 3 days with either anti-PD-1 (FIG. 13A) or anti-CTLA-4 (FIG. 13B) antibodies according to the indicated schedule, and tumor volume was monitored longitudinally by caliper measurement. P<0.01 and *P<0.001

(t test) ††\P<0.001 (one-way ANOVA and Tukey's posttest relative to polyI. C); *P<0.05, P<0.001, and ****P<0.0001 (two-way ANOVA and Dunnett's posttest relative to polyI: C); †P<0.05 and †††\P<0.0001 (two-way ANOVA and Dunnett's posttest relative to peptide mix+polyI:C).

Figure 14A:
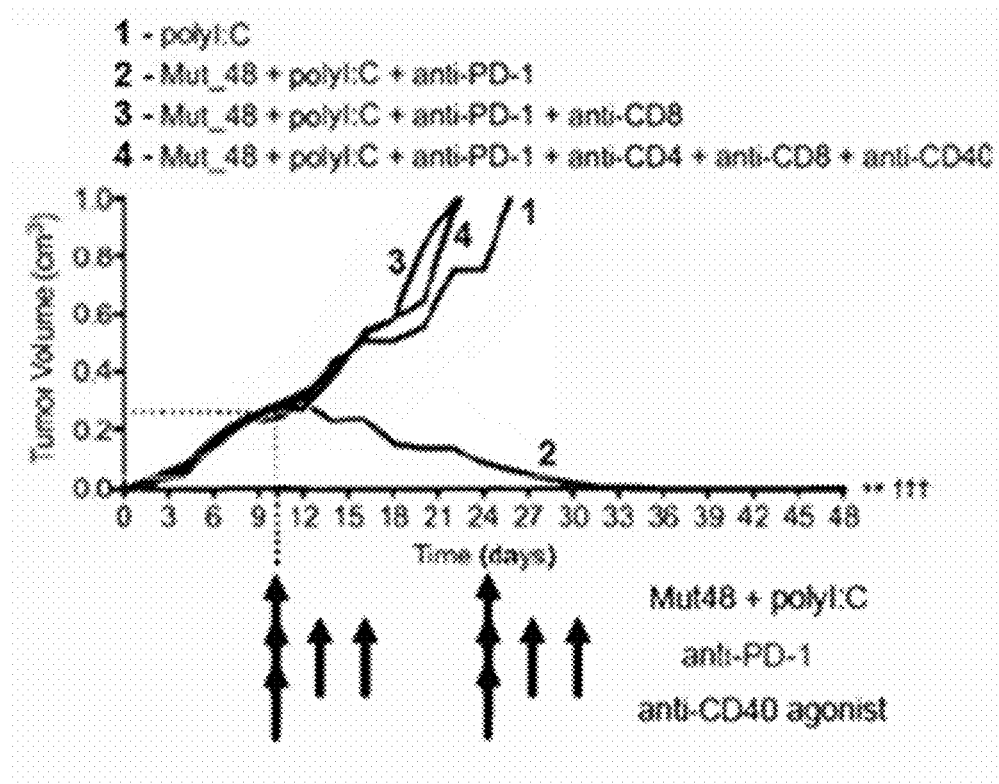
FIGS. 14A and 14B depict results demonstrating that neoantigen-specific CD4+ T cells help govern therapeutic vaccination. Specifically.
Figure 14B:
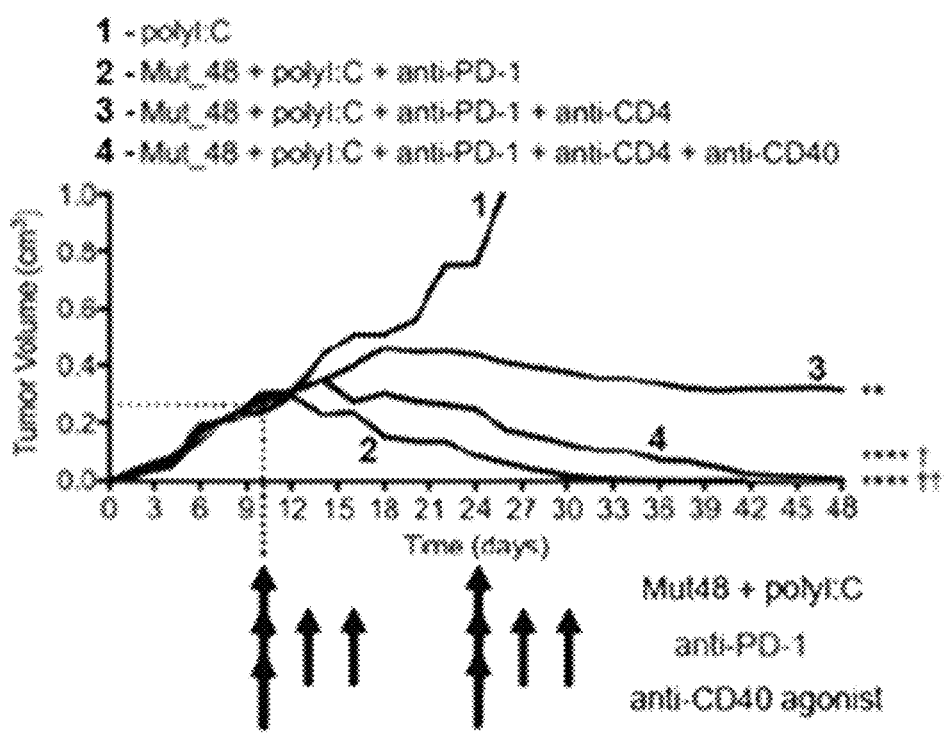

Example 11. Neoantigen-Specific CD4+ T Cells Help Govern Therapeutic Vaccination With respect to the data depicted in FIG. 14A and FIG. 14B, SCC VII tumors were established in groups of 10 C3H/J mice and the indicated treatment modalities were initiated 10d later when tumor volume averaged 300 mm$^3$. CD4+ versus CD8+ subsets were depleted prior to the initiation of the curative vaccine therapy (Mut48 peptide+ polyI:C+anti-PD-1). In the indicated groups, CD4+ or CD8+ T cells were depleted on day 9 with monoclonal antibodies (GK1.5 or 3-155; anti-CD40-FGK45. Depletion of the CD8+ subset rendered the vaccine ineffective, while removal of CD4+ T cells still allowed the treatment to mount a statistically-significant therapeutic effect (as shown in FIG. 14A and FIG. 14B).

Figure 15A:
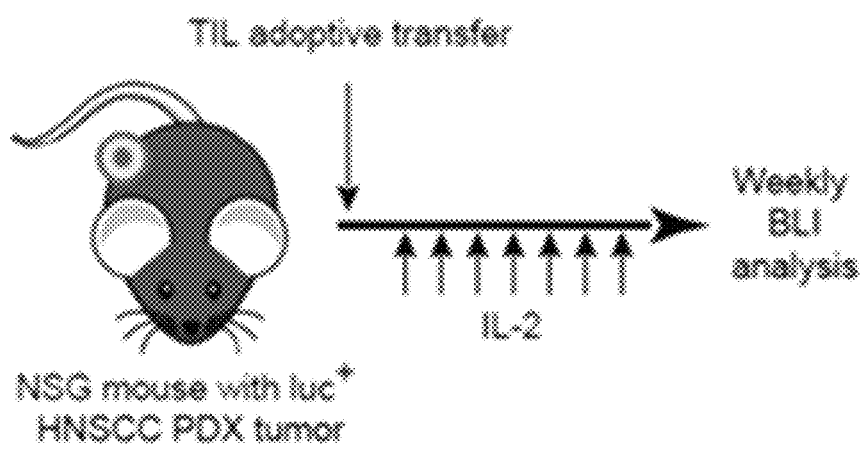
FIG. 15A depicts an adoptive cellular therapy protocol as detailed herein.
Figure 15B:
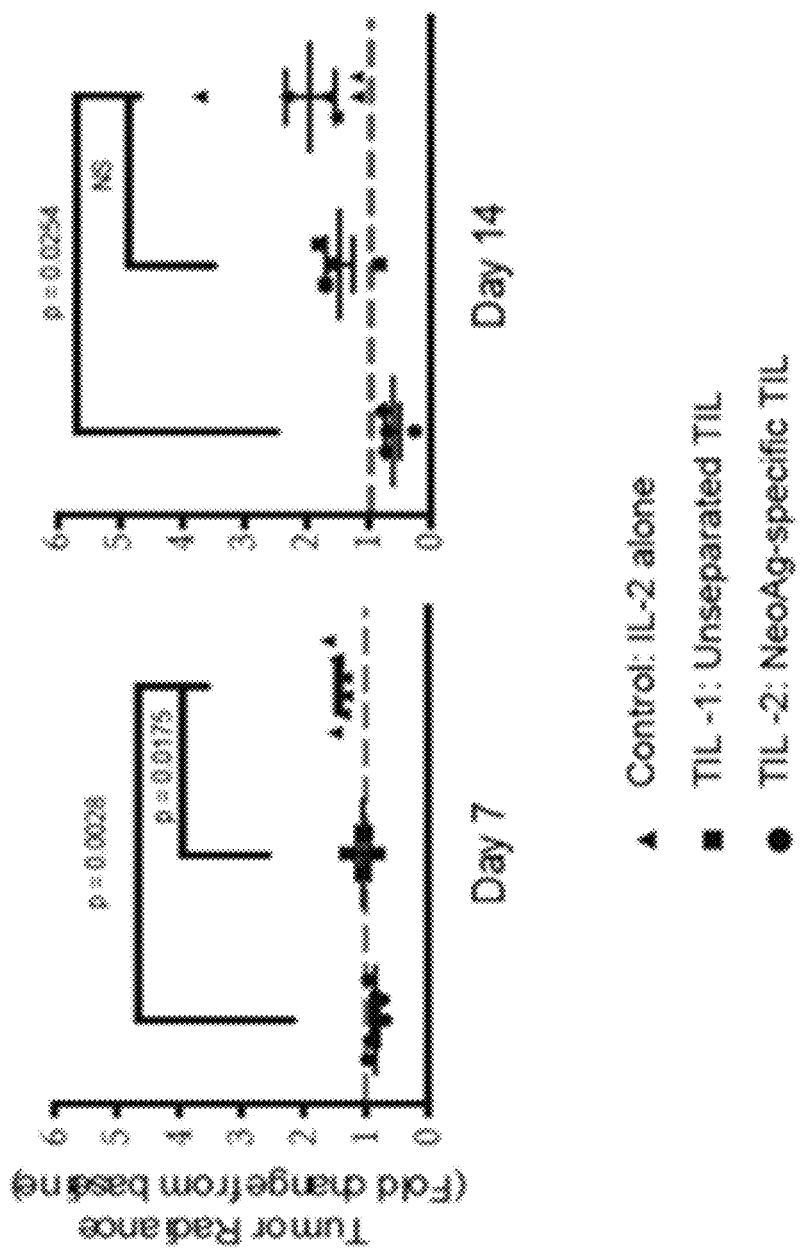
FIG. 15B depicts tumor radiance measurements for cohorts as detailed herein.

Example 12. Adoptive Immunotherapy of HNSCC PDX Tumors with Neoantigen-Specific TIL FIG. 15A outlines an adoptive cellular therapy (ACT) protocol used herein. Groups of NSG mice bearing established R/M HNSCC PDX tumors from patient Hu_009 were treated with 5×10$^6$ total ("bulk") TIL-1 or a distinct fragment culture containing 60% (by ICS assay) of CD8+T cells specific for the RPS2 Val2051le NeoAg. The graphs in FIG. 15B show the results of BLI measurements of tumor radiance that were performed at day 7 and 14. Subsequent measurements made at day 21 showed progression in the TIL-1 and Control groups, while tumors in mice receiving TIL-2 remained at or below baseline levels.

Example 13. Dynamic Monitoring of Patient-Derived Cancer Line to Assess Capacity of TCR to Kill Tumor Lines Expressing HPV E6

Figure 16A:
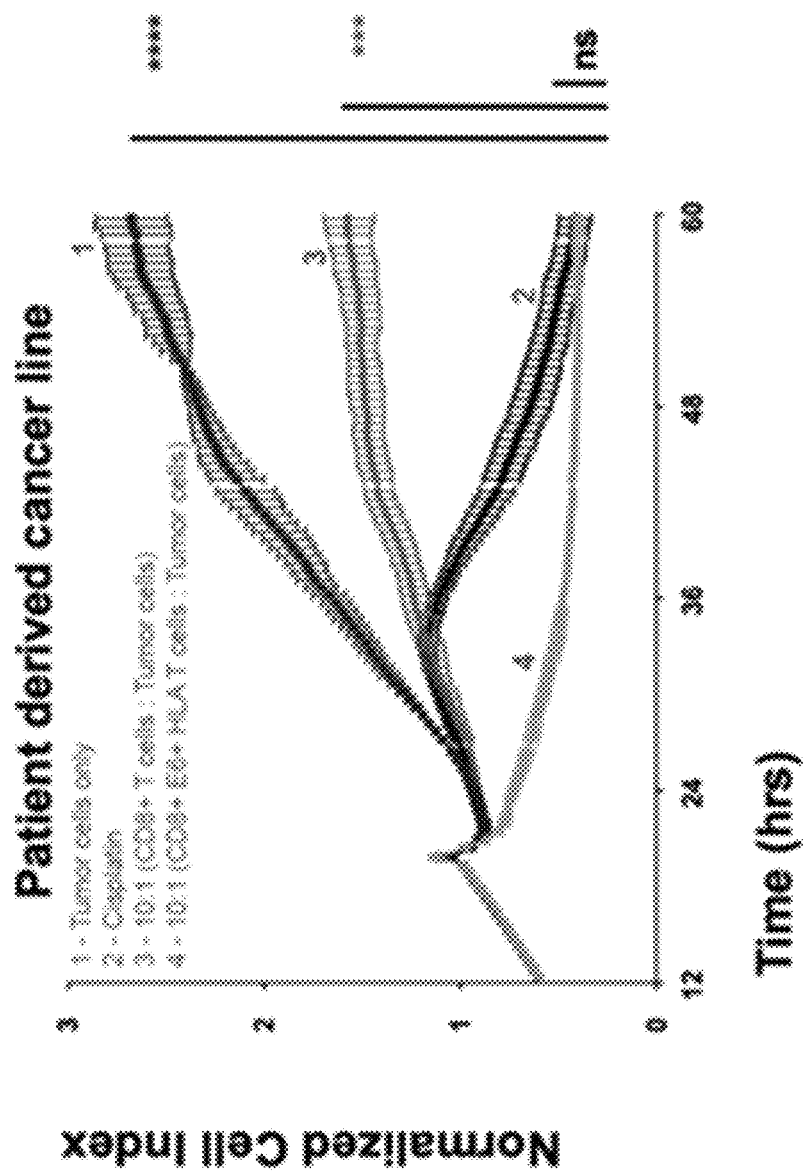
FIG. 16A depicts dynamic monitoring of a patient derived cancer as detailed herein.

FIG. 16A depicts dynamic monitoring of patient-derived cancer line to assess the capacity of the TCR to specifically kill tumor lines expressing the HPV E6 protein at 10:1 effector to target ratio. Curve 1 shows the natural growth of the tumor cells with no added effector cells. Curve 2 demonstrates that the chemotherapeutic, cisplatin, can kill these lines within 48 hours. To assess non-specific (alloreactivity) background killing by the CD8 T cells, the growth of CD8 T cells that were stimulated and expanded but not subjected to CRISPR or LV editing are represented by Curve 3. The neoantigen-engineered CD8 T cells (Curve 4) shows superior killing capacity than even chemotherapy at very early time points.

Example 14. Dynamic Monitoring of E6+HLA-A*02:01+Tumor Line to Assess Capacity of TCR to Kill Tumor Lines Expressing HPV E6

Figure 16B:
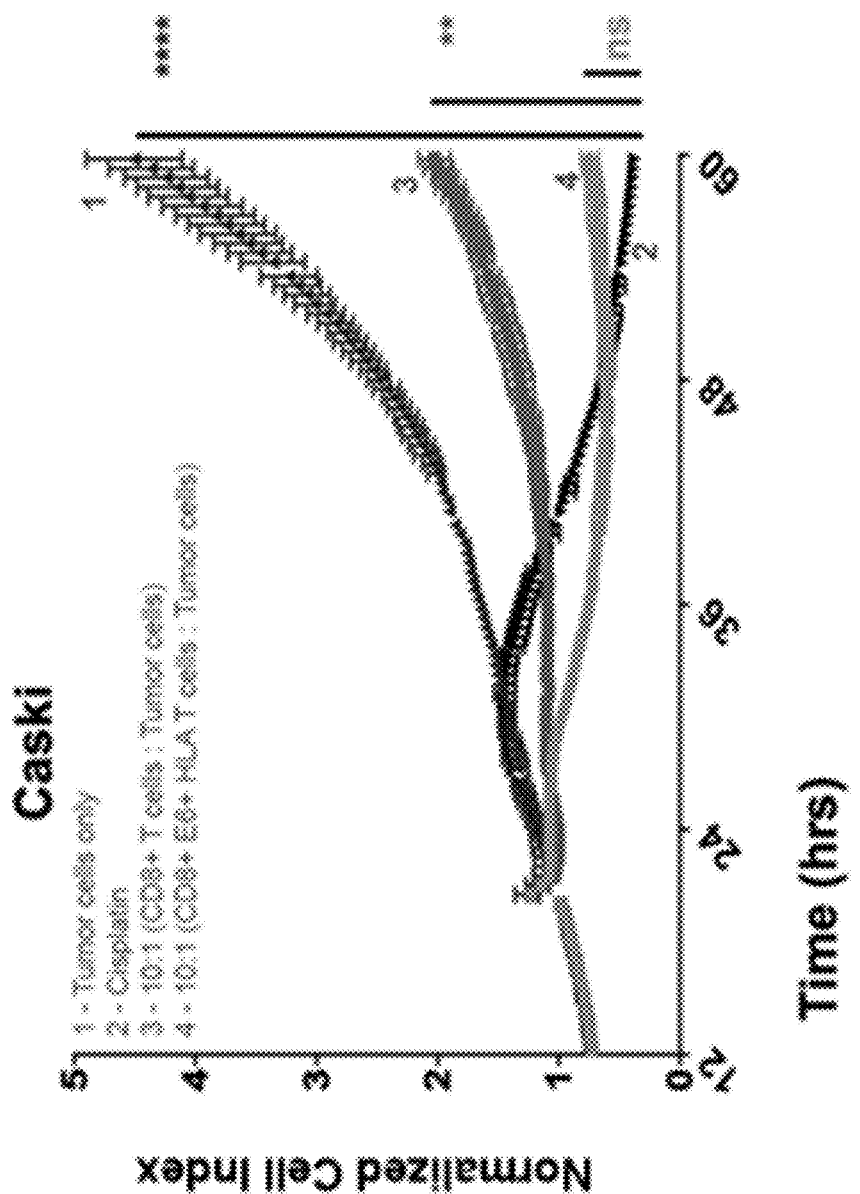
FIG. 16B depicts dynamic monitoring of a Caski tumor line as detailed herein.

FIG. 16B depicts dynamic monitoring of E6+HLA-A*02: 01+tumor line (Caski) to assess the capacity of the engineered TCR to specifically kill tumor lines expressing the HPV E6 protein at 10:1 effector to target ratio. Curve 1 shows the natural growth of the tumor cells with no added effector cells. Curve 2 demonstrates that the chemotherapeutic, Cisplatin, can kill the Caski cells within 48 hours. To assess non-specific (alloreactivity) background killing by the CD8 T cells, the growth of CD8 T cells that were stimulated and expanded but NOT subjected to CRISPR or LV editing are represented by Curve 3. The neoantigen-engineered CD8 T cells (Curve 4) shows superior killing capacity than even chemotherapy at very early time points.

Example 15. Peptide Vaccine Results in Immune Editing of Tumors

The term "immune editing' refers to the phenomenon of a tumor changing its composition in response to immune pressure. In the specific examples it was demonstrated that in two independent vaccine recipients of peptide compositions generated using the method described herein, the on-treatment biopsy showed that the tumor had lost expression of mutations targeted in the vaccine (both Pancreatic Neuroendocrine Tumor or PNET patients). This demonstrates that the neoantigen identification methods described herein and resulting peptide compositions are accurate in developing effective therapeutics in that the peptide composition was able to eradicate tumor cells that express the mutations selected by the describe neoantigen calling method as neoantigens.

Figure 17A:
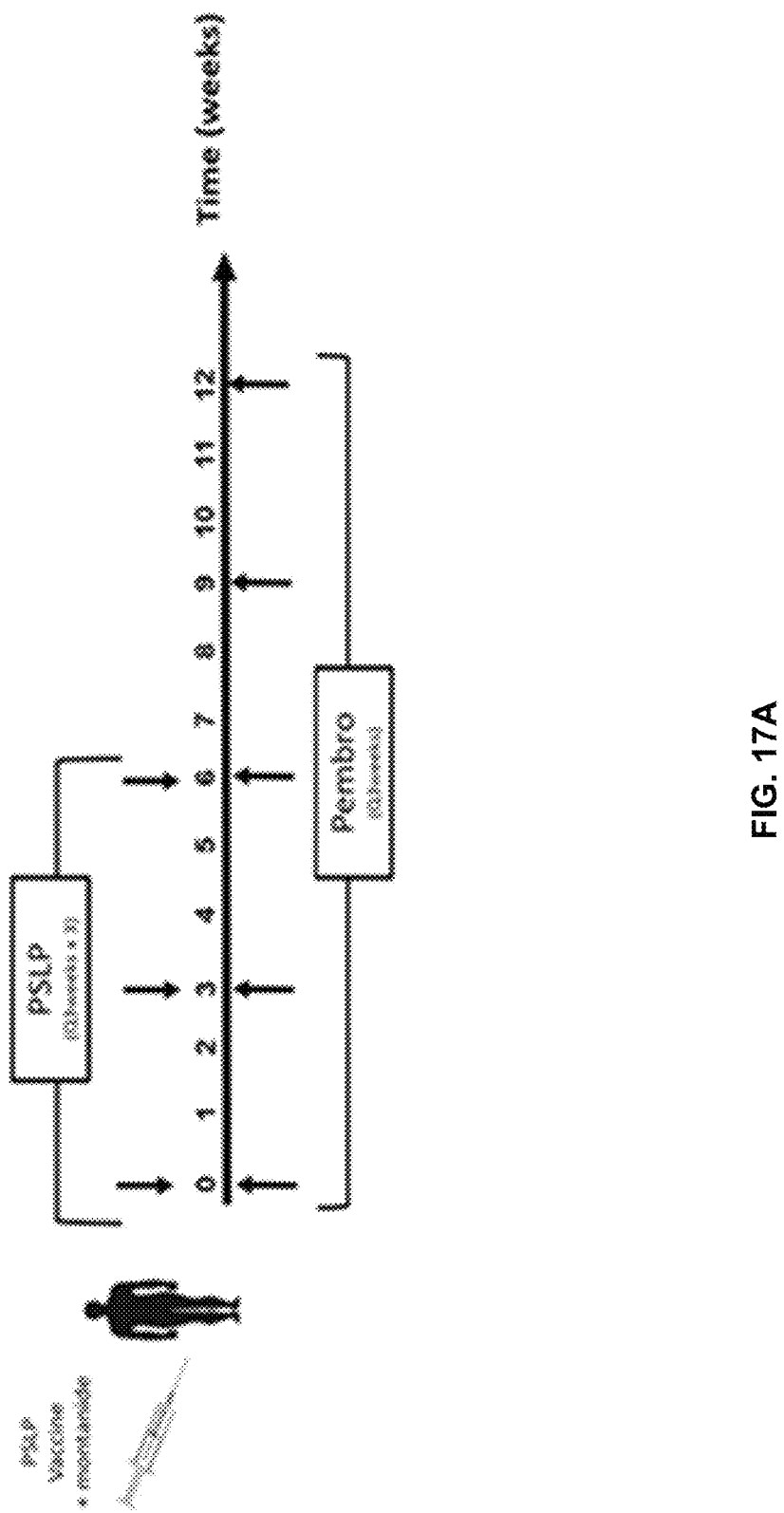
FIG. 17A depicts a treatment protocol utilized to generate the data depicted in FIG. 17B and FIG. 18, all as described herein.
Figure 17B:
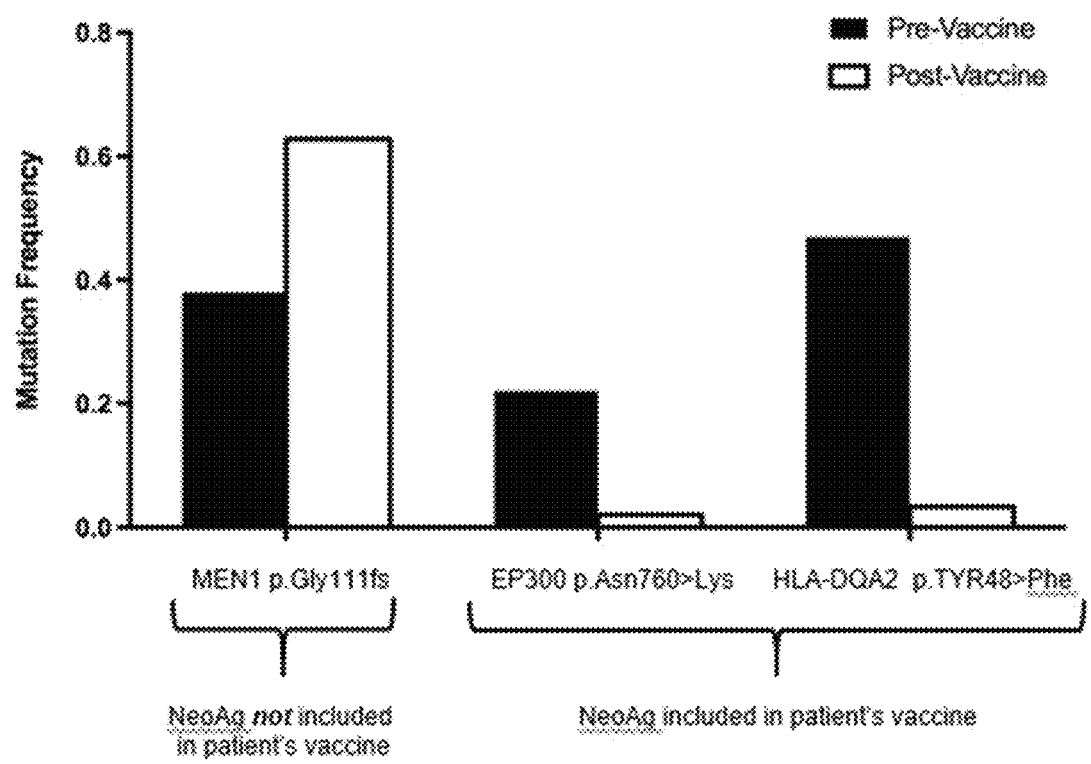
FIG. 17B depicts data from a patient demonstrating immune editing of tumors, as detailed herein.
Figure 18:
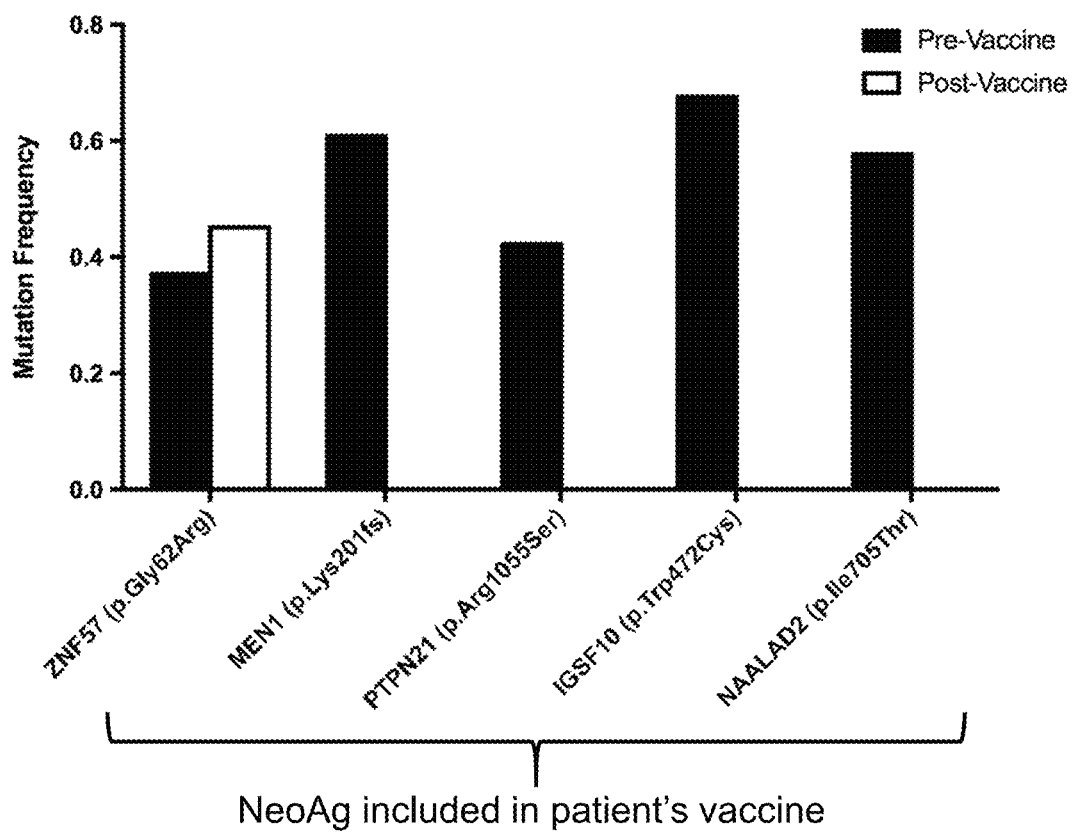
FIG. 18 depicts data from a patient demonstrating immune editing of tumors, as detailed herein.

More specifically, and as shown in FIG. 17B and FIG. 18 it was found that in two independent vaccine recipients, the on-treatment biopsy showed that the tumor had lost expression of mutations targeted in the vaccine; 2 out of 2 in Patient 1 and 4 out of 5 in Patient 5 (both are Pancreatic Neuroendocrine Tumor or PNET patients). Both patients were treated according to the timeline and vaccination schedule depicted in FIG. 17A. In each case, the patients were immunized according to this schedule with synthetic peptides corresponding to validated neoantigens detected using the described platform. In each case, the peptides were emulsified in Montanide adjuvant and delivered by subcutaneous injection at 100 μg per peptide/dose.

This indicates that the targeting that comes from the methods described herein is accurate such that the vaccine was able to eradicate tumor cells that express the mutations selected by our platform as neoantigens. This is significant because if the identification had been wrong, the tumor would be expected to continue to express the mutations in question as their targeting posed no threat. With respect to the data detailed herein, variant allele frequency analysis was performed on tumor biopsies before and after PCV administration. In both independent cases of pancreatic neuroendocrine tumors, mutations targeted by the vaccine were no longer detectable as expressed within the tumor biopsy, indicative of immune editing.

Figure 19:
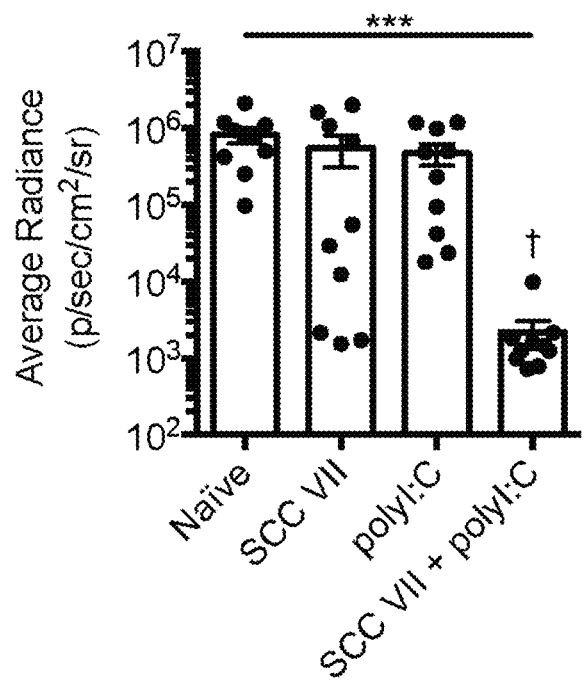
FIG. 19 depicts average radiance data under a variety of described experimental conditions, as detailed herein.
Figure 20:
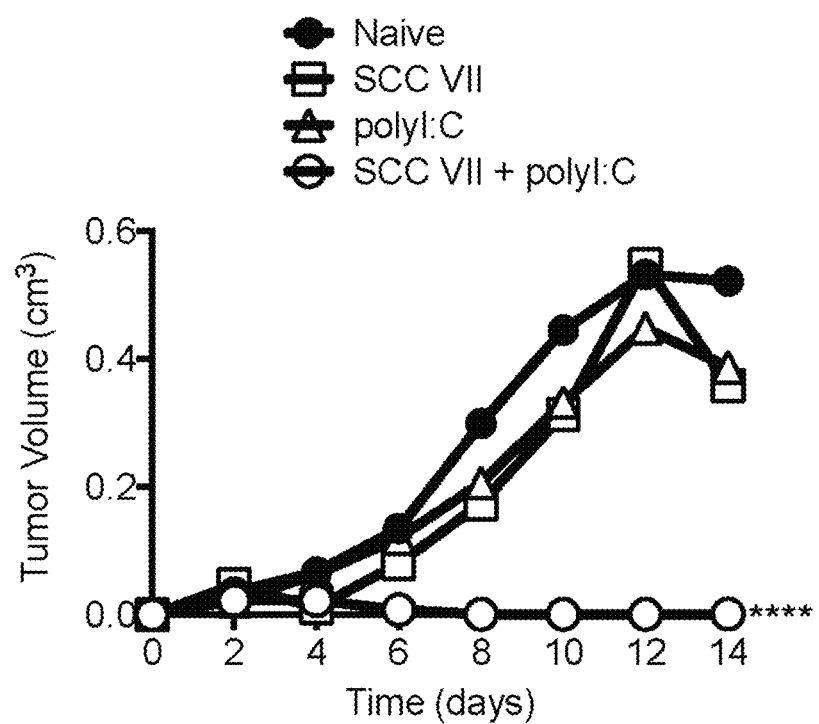
FIG. 20 depicts data demonstrating tumor volume over time under a variety of described experimental conditions.

Example 16. Squamous Cell Carcinoma Studies Indicate that Therapeutic Neoantigen Vaccination Requires Linked CD4+ T Cell Help Squamous cell carcinoma VII (SCC VII) is a spontaneously arising murine tumor which closely resembles human head and neck squamous cell carcinoma (HSNCC) in several key aspects, including pulmonary and lymph node (LN) metastasis as well as poor immunogenicity. To identify the SCC VII mutations targeted by natural immune responses, inherent immunogenicity was direst established. Briefly, C3H/HeJ mice were subcutaneously (SC) immunized with 10$^7$ irradiated (50 Gy) SCC VII cells, either alone or supplemented with 50 g of the adjuvant polyinosinic-polycytidylic acid (polyI:C), a synthetic Toll-like receptor 3 (TLR3) ligand. Immunized mice were challenged 14 days later with 5×10⁵ live SCC VII cells transduced to express luciferase and green fluorescent protein (SCC VII-Luc/GFP) to enable tracking by bioluminescence (BLI). Whereas whole-cell vaccination with irradiated SCC VII alone did not protect mice from tumor outgrowth following challenge, revealing SCC VII as a poorly-immunogenic tumor by this classical definition, prophylaxis was achievable through co-delivery of polyI:C (see, for e.g.: FIG. 19 and FIG. 20).

Figure 21:
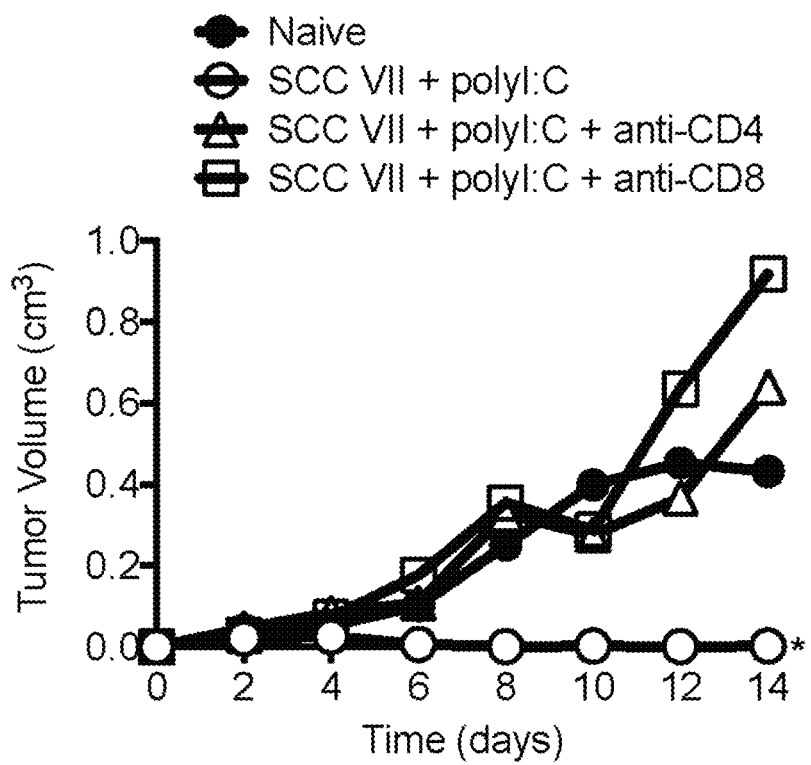
FIG. 21 depicts data demonstrating tumor volume over time under a variety of described experimental conditions.
Figure 22:
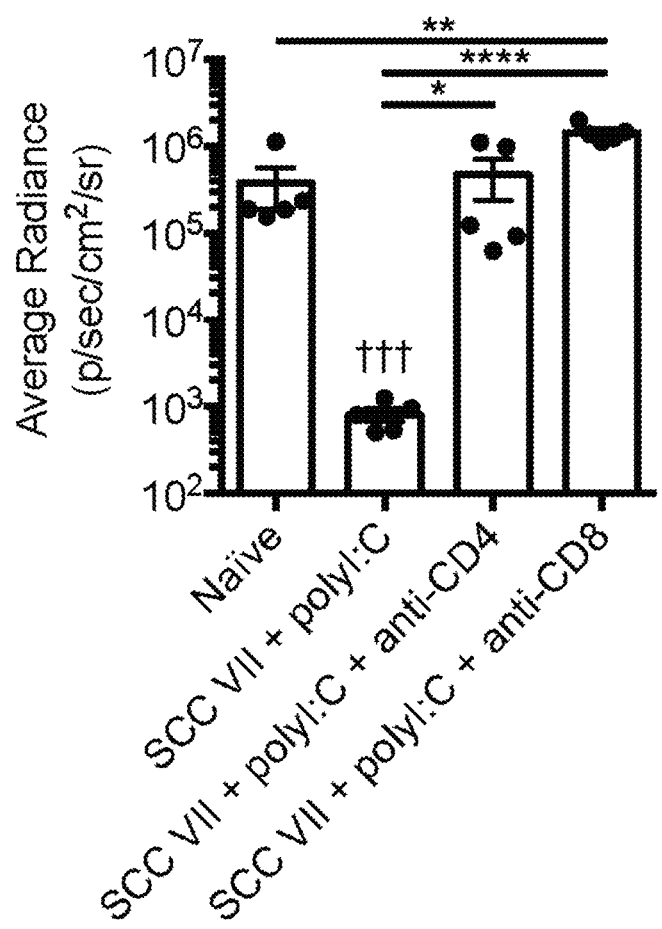
FIG. 22 depicts average radiance data under a variety of described experimental conditions, as detailed herein.

Thus, SCC VII contains antigens capable of conferring protective immunity. This depends on both CD4+ and CD8+ T cells, as depletion of either subset before or after vaccination led to tumor outgrowth following subsequent challenge (see, for e.g.: FIG. 21 and FIG. 22). Notably, tumors in mice depleted of CD4+ T cells just prior to challenge displayed a reduced growth rate compared to controls, suggesting that this subset is required at both the initiation phase of the vaccine-induced response and later to maintain its efficacy following challenge.

To identify SCC VII antigens conferring protective immunity, an approach was applied which combined genomic sequencing to detect well-expressed coding mutations with functional analysis of natural immune responses to tumor antigens. The exome of the SCC VII tumor was first compared to that of normal control C3H/HeJ caudal tissue samples. This analysis yielded 1,481 variants in coding sequences among the 4,771 total variants detected in the tumor versus reference exome. Of these, 270 could be confirmed as expressed by at least 1 read of the variant base in the tumor RNA, with 39 mutations reaching our selected expression threshold of 20% variant allele frequency (VAF) and >10 reads in the tumor RNA sample. These 39 mutations were translated into amino acid sequences, and 20-mer peptide pairs were synthesized for each mutation in which the mutated amino acid was placed at position 6, 10, or 15 within the linear peptide flanked by wild type sequence (table S1).

Figure 23:
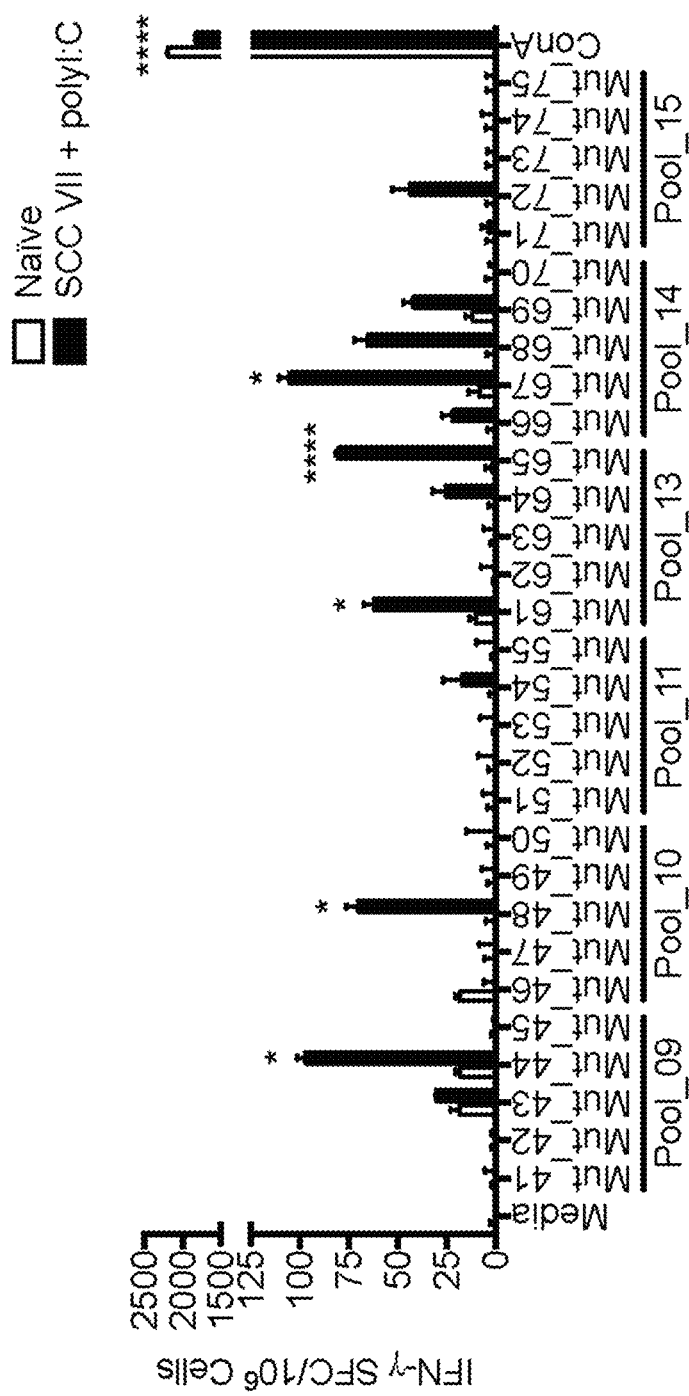
FIG. 23 depicts ELISPOT data determined from pools of peptides as detailed herein.

81 candidate peptides representing the filtered 39 mutations were tested as targets for T cells generated by immunization with the irradiated SCC VII±polyI:C and live tumor challenge protocol described above. This involved re-stimulation of splenic and tumor-draining LN mononuclear cells isolated 14 days after challenge with bone marrow-derived dendritic cells (BMDC) pulsed with 16 pools of 20-mer peptide pairs in an ELISPOT assay for assessment of effector cytokine IFN-γ production. Significant frequencies of IFN-γ spot forming cells (SFC) over background were found for 6 of the 16 peptide pools screened. Peptide pools that produced strong IFN-γ responses were subsequently deconvoluted to detect the specific mutant peptides targeted. This analysis revealed Pik3ca (Mut 44), Cltc (Mut 48), Ctnnd1 (Mut 61), and Otud5 (Mut_65 and Mut 67) as the mutated genes targeted by the natural immune responses to SCC VII (see, for e.g.: FIG. 23).

Figure 24:
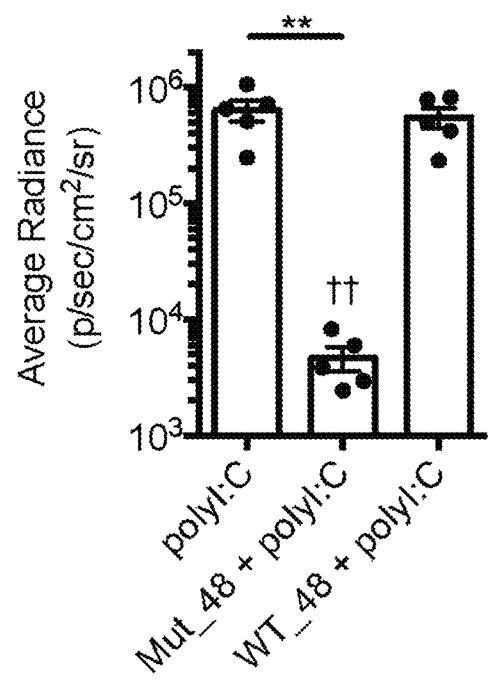
FIG. 24 depicts average radiance data under a variety of described experimental conditions, as detailed herein.

The immunogenicity of the four SCC VII NeoAg was next investigated. C3H/HeJ mice were immunized SC once or boosted three weeks later with a pool of the five recognized 20-mer peptides+polyI:C. Mice were challenged 10 days after the last (booster) vaccination with live SCC VII-Luc/GFP SC on the opposite flank, and tumor outgrowth was subsequently monitored by BLI and caliper measurements. Whereas a single injection of the pooled NeoAg peptides did not protect from challenge with the aggressive SCC VII tumor, boosting this response with a second immunization led to significantly smaller tumor sizes at all time points assayed. CD4+ and CD8+ T cells were critical for mediating the protective immunity of the NeoAg+polyI:C vaccine, as this was lost with depletion of either population prior to challenge. When the individual NeoAg peptides were tested for their contribution to the observed immunity, only Mut_48 (Cltc A15) demonstrated the ability to confer protection from challenge, while the wild type peptide (WT_48) was not protective (see: FIG. 24). These data indicate that the T cell response to Mut_48 mediates protective immunity following prophylactic peptide vaccination.

Figure 25:
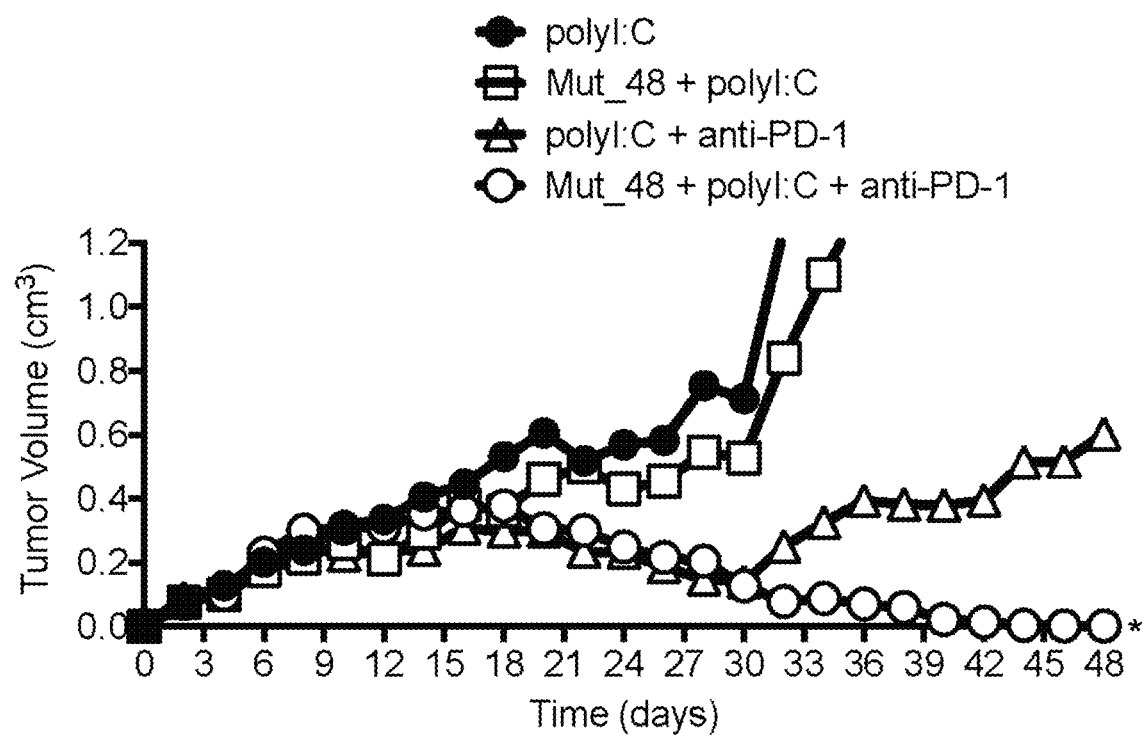
FIG. 25 depicts data demonstrating tumor volume over time under a variety of described experimental conditions.

Given the synergistic potency of combining PD-1 blockade with NeoAg peptide vaccination, and the ability of the Mut 48 peptide to induce both CD4+ and CD8+ T cell responses against the SCC VII tumor, we examined whether these could be combined to treat large established tumors. SCC VII-Luc/GFP tumors were grown in groups of mice and allowed to reach a volume of ~300-400 mm³ before treatment with two cycles of contralateral SC Mut_48+ polyI:C mixtures and/or IP anti-PD-1 on days 10 and 24. The Mut_48+polyI:C vaccine alone did not result in a therapeutic benefit, whereas anti-PD-1+polyI:C led to initial tumor control that was subsequently lost (progressive growth resumed once ICB was withdrawn at day 30). In contrast, combining PD-1 blockade with the Mut_48 NeoAg vaccine resulted in the complete and durable (>90 days) eradication of large established tumors (see: FIG. 25).

What is claimed is:

1. A method of identifying a neoantigen peptide candidate comprising:
   generating tumor sequence reads from a tumor sample and normal sequence reads from a normal control sample;
   comparing the tumor sequence reads with the normal sequence reads to identify one or more exome variants;
   selecting from the one or more exome variants a set of exome variants that satisfy a variant calling policy, wherein the variant calling policy comprises a variant allele frequency of a variant among the set of exome variants in a normal exome being equal to about 50% or less;
   generating for at least one exome variant of the set of exome variants that satisfy the variant calling policy one or more synthetic peptides, each synthetic peptide having one or more mutated amino acids at one or more pre-selected locations of the synthetic peptide, wherein the method excludes the use of an in silico MHC binding prediction algorithm;
   evaluating immunogenicity for one or more of the peptides; and
   identifying at least one peptide demonstrating a predetermined immunogenic activity as a neoantigen peptide candidate, wherein the predetermined immunogenic activity comprises production of IFN-γ or IL-5 by a T cell.

2. The method of claim 1, wherein the tumor sequence reads are tumor mRNA sequence reads, tumor exome sequence reads, or both.

3. The method of claim 1, wherein non-tumor sequence reads are non-tumor exome sequence reads.

4. The method of claim 1, wherein the predetermined immunogenic activity comprises stimulation of a T cell response by the at least one peptide.

5. The method of claim 4, wherein the T cell response is predominantly a CD4+ T cell response.

6. The method of claim 5, wherein the CD4+ T cell response is a Th1 or Th2 response.

7. The method of claim 4, wherein the T cell response is predominantly a CD8+ T cell response.

8. The method of claim 4, wherein the T cell response is both a CD4+ T cell response and a CD8+ T cell response.

9. The method of claim 1, further comprising producing the at least one identified peptide.

10. The method of claim 1, further comprising treating an individual associated with the tumor sample with a composition comprising the at least one identified peptide, or an engineered immune cell that biologically recognizes that at least one peptide.

* * * * *

SEQUENCE LISTING

<160> NUMBER OF SEQ ID NOS: 34

<210> SEQ ID NO 1
<211> LENGTH: 48
<212> TYPE: DNA
<213> ORGANISM: Artificial Sequence
<220> FEATURE:
<223> OTHER INFORMATION: Hinge domain: IgG1 heavy chain hinge

<400> SEQUENCE: 1
ctcgagccca aatcttgtga caaaactcac acatgcccac cgtgcccg        48

<210> SEQ ID NO 2
<211> LENGTH: 81
<212> TYPE: DNA
<213> ORGANISM: Artificial Sequence
<220> FEATURE:
<223> OTHER INFORMATION: Transmembrane domain: CD28 transmembrane region

<400> SEQUENCE: 2
ttttgggtgc tggtggtggt tggtggagtc ctggcttgct atagcttgct agtaacagtg    60
gcctttatta ttttctgggt g                                              81

<210> SEQ ID NO 3
<211> LENGTH: 126
<212> TYPE: DNA
<213> ORGANISM: Artificial Sequence
<220> FEATURE:
<223> OTHER INFORMATION: Intracellular domain: 4-1BB co-stimulatory
      signaling region

<400> SEQUENCE: 3
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                             126

<210> SEQ ID NO 4
<211> LENGTH: 123
<212> TYPE: DNA
<213> ORGANISM: Artificial Sequence
<220> FEATURE:
<223> OTHER INFORMATION: Intracellular domain: CD28 co-stimulatory
      signaling region

<400> SEQUENCE: 4
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                123

<210> SEQ ID NO 5
<211> LENGTH: 339
<212> TYPE: DNA
<213> ORGANISM: Artificial Sequence
<220> FEATURE:
<223> OTHER INFORMATION: Intracellular domain: CD3 zeta signaling region

<400> SEQUENCE: 5
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240
cggaggggca gggggcacga tggcctttac cagggtctca gtacagccac caaggacacc   300
tacgacgccc ttcacatgca ggccctgccc cctcgctaa                         339

<210> SEQ ID NO 6
<211> LENGTH: 51
<212> TYPE: PRT
<213> ORGANISM: Artificial Sequence
<220> FEATURE:
<223> OTHER INFORMATION: Human CD8 alpha hinge domain

<400> SEQUENCE: 6

Pro Ala Lys Pro Thr Thr Thr Pro Ala Pro Arg Pro Pro Thr Pro Ala
1               5                   10                  15

Pro Thr Ile Ala Ser Gln Pro Leu Ser Leu Arg Pro Glu Ala Cys Arg
            20                  25                  30

-continued

```
Pro Ala Ala Gly Gly Ala Val His Thr Arg Gly Leu Asp Phe Ala Cys
            35                  40                  45

Asp Ile Tyr
    50

<210> SEQ ID NO 7
<211> LENGTH: 49
<212> TYPE: PRT
<213> ORGANISM: Artificial Sequence
<220> FEATURE:
<223> OTHER INFORMATION: Mouse CD8 alpha hinge domain

<400> SEQUENCE: 7

Lys Val Asn Ser Thr Thr Thr Lys Pro Val Leu Arg Thr Pro Ser Pro
1               5                   10                  15

Val His Pro Thr Gly Thr Ser Gln Pro Gln Arg Pro Glu Asp Cys Arg
            20                  25                  30

Pro Arg Gly Ser Val Lys Gly Thr Gly Leu Asp Phe Ala Cys Asp Ile
        35                  40                  45

Tyr

<210> SEQ ID NO 8
<211> LENGTH: 21
<212> TYPE: PRT
<213> ORGANISM: Artificial Sequence
<220> FEATURE:
<223> OTHER INFORMATION: Human CD8 alpha transmembrane domain

<400> SEQUENCE: 8

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 9
<211> LENGTH: 21
<212> TYPE: PRT
<213> ORGANISM: Artificial Sequence
<220> FEATURE:
<223> OTHER INFORMATION: Mouse CD8 alpha transmembrane domain

<400> SEQUENCE: 9

Ile Trp Ala Pro Leu Ala Gly Ile Cys Val Ala Leu Leu Leu Ser Leu
1               5                   10                  15

Ile Ile Thr Leu Ile
            20

<210> SEQ ID NO 10
<211> LENGTH: 21
<212> TYPE: PRT
<213> ORGANISM: Artificial Sequence
<220> FEATURE:
<223> OTHER INFORMATION: Rat CD8 alpha transmembrane domain

<400> SEQUENCE: 10

Ile Trp Ala Pro Leu Ala Gly Ile Cys Ala Val Leu Leu Leu Ser Leu
1               5                   10                  15

Val Ile Thr Leu Ile
            20

<210> SEQ ID NO 11
<211> LENGTH: 42
<212> TYPE: PRT
```

```
<213> ORGANISM: Artificial Sequence
<220> FEATURE:
<223> OTHER INFORMATION: 4-1BB costimulatory signaling region

<400> SEQUENCE: 11

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 12
<211> LENGTH: 105
<212> TYPE: DNA
<213> ORGANISM: Artificial Sequence
<220> FEATURE:
<223> OTHER INFORMATION: ICOS costimulatory signaling region

<400> SEQUENCE: 12
acaaaaaaga agtattcatc cagtgtgcac gaccctaacg gtgaatacat gttcatgaga      60
gcagtgaaca cagccaaaaa atccagactc acagatgtga cccta                    105

<210> SEQ ID NO 13
<211> LENGTH: 108
<212> TYPE: DNA
<213> ORGANISM: Artificial Sequence
<220> FEATURE:
<223> OTHER INFORMATION: OX40 costimulatory signaling region

<400> SEQUENCE: 13
agggaccaga ggctgccccc cgatgcccac aagcccctg ggggaggcag tttccggacc      60
cccatccaag aggagcaggc cgacgcccac tccaccctgg ccaagatc                 108

<210> SEQ ID NO 14
<211> LENGTH: 220
<212> TYPE: PRT
<213> ORGANISM: Artificial Sequence
<220> FEATURE:
<223> OTHER INFORMATION: CD28

<400> SEQUENCE: 14

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140
```

Leu Phe Pro Gly Pro Ser Lys Pro Phe Trp Val Leu Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 15
<211> LENGTH: 112
<212> TYPE: PRT
<213> ORGANISM: Artificial Sequence
<220> FEATURE:
<223> OTHER INFORMATION: CD3 zeta signaling domain

<400> SEQUENCE: 15

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 16
<211> LENGTH: 20
<212> TYPE: PRT
<213> ORGANISM: Artificial Sequence
<220> FEATURE:
<223> OTHER INFORMATION: Mutated 20-mer peptide

<400> SEQUENCE: 16

Leu Leu Arg His Leu Gly Leu Gln Asn Arg Arg Ile Asn Leu His Ser
1               5                   10                  15

His Asp Tyr Gly
            20

<210> SEQ ID NO 17
<211> LENGTH: 20
<212> TYPE: PRT
<213> ORGANISM: Artificial Sequence
<220> FEATURE:
<223> OTHER INFORMATION: Mutated 20-mer peptide

<400> SEQUENCE: 17

Leu Ala Ser Tyr Thr Tyr Asn Ile Glu Ala Val Ser Cys Asp Glu Ala
1               5                   10                  15

Leu Val Asp Ile
            20

<210> SEQ ID NO 18
<211> LENGTH: 20
<212> TYPE: PRT
<213> ORGANISM: Artificial Sequence
<220> FEATURE:
<223> OTHER INFORMATION: Mutated 20-mer peptide

<400> SEQUENCE: 18

Lys Val Thr Gly Ala Gly Phe Val Val Phe Asn Gly Ala Leu Lys Thr
1               5                   10                  15

Ser Ser Gly Phe
            20

<210> SEQ ID NO 19
<211> LENGTH: 20
<212> TYPE: PRT
<213> ORGANISM: Artificial Sequence
<220> FEATURE:
<223> OTHER INFORMATION: Mutated 20-mer peptide

<400> SEQUENCE: 19

Gly Gln Asp Arg Pro Ile Lys Thr Phe Gln Gly His Thr Asn Gly Val
1               5                   10                  15

Asn Ala Ile Lys
            20

<210> SEQ ID NO 20
<211> LENGTH: 20
<212> TYPE: PRT
<213> ORGANISM: Artificial Sequence
<220> FEATURE:
<223> OTHER INFORMATION: Mutated 20-mer peptide

<400> SEQUENCE: 20

Glu Ile Thr Ala Met Pro Cys Asn Met Asn Thr Gln Cys Pro His Gly
1               5                   10                  15

Gly Tyr Cys Met
            20

<210> SEQ ID NO 21
<211> LENGTH: 20
<212> TYPE: PRT
<213> ORGANISM: Artificial Sequence
<220> FEATURE:
<223> OTHER INFORMATION: Mutated 20-mer peptide

<400> SEQUENCE: 21

Leu Ser Pro Asp Cys Leu Gly His Ala Gly Leu Val Tyr Glu Cys Thr
1               5                   10                  15

Leu Gly Glu Glu
            20

<210> SEQ ID NO 22
<211> LENGTH: 20
<212> TYPE: PRT
<213> ORGANISM: Artificial Sequence
<220> FEATURE:
<223> OTHER INFORMATION: Mutated 20-mer peptide

<400> SEQUENCE: 22

Ser Ser Gly Asn Leu Pro Gly Arg Asn Ser Phe Glu Val Arg Val Cys
1               5                   10                  15

Ala Cys Pro Gly
            20

```
<210> SEQ ID NO 23
<211> LENGTH: 20
<212> TYPE: PRT
<213> ORGANISM: Artificial Sequence
<220> FEATURE:
<223> OTHER INFORMATION: Mutated 20-mer peptide

<400> SEQUENCE: 23

Gly Glu Gln Val Leu Ser Leu Lys Ser Gln Val Asp Ala Gln Leu Leu
1               5                   10                  15

Thr Val Gln Lys
            20

<210> SEQ ID NO 24
<211> LENGTH: 20
<212> TYPE: PRT
<213> ORGANISM: Artificial Sequence
<220> FEATURE:
<223> OTHER INFORMATION: Mutated 20-mer peptide

<400> SEQUENCE: 24

Arg Arg Gly Leu Arg Ile Asp Ile Asp Ala Thr Cys Thr Pro Arg Arg
1               5                   10                  15

Ala Ser Ser Asn
            20

<210> SEQ ID NO 25
<211> LENGTH: 20
<212> TYPE: PRT
<213> ORGANISM: Artificial Sequence
<220> FEATURE:
<223> OTHER INFORMATION: Mutated 20-mer peptide

<400> SEQUENCE: 25

Met Ala Val Phe Ala Asp Leu Asp Leu Arg Ala Gly Cys Asp Leu Lys
1               5                   10                  15

Ala Leu Arg Gly
            20

<210> SEQ ID NO 26
<211> LENGTH: 20
<212> TYPE: PRT
<213> ORGANISM: Artificial Sequence
<220> FEATURE:
<223> OTHER INFORMATION: Mutated 20-mer peptide

<400> SEQUENCE: 26

Asp Leu Arg Ala Gly Cys Asp Leu Lys Ala Leu Arg Gly Leu Val Glu
1               5                   10                  15

Thr Ala Ala His
            20

<210> SEQ ID NO 27
<211> LENGTH: 20
<212> TYPE: PRT
<213> ORGANISM: Artificial Sequence
<220> FEATURE:
<223> OTHER INFORMATION: Mutated 20-mer peptide

<400> SEQUENCE: 27

Glu Tyr Asp Asp Ile Pro Val Arg Ser Val Arg Val Ser Trp Arg Pro
1               5                   10                  15

Pro Ala Asp Asp
```

```
            20

<210> SEQ ID NO 28
<211> LENGTH: 20
<212> TYPE: PRT
<213> ORGANISM: Artificial Sequence
<220> FEATURE:
<223> OTHER INFORMATION: Mutated 20-mer peptide

<400> SEQUENCE: 28

Gln Leu Ala Arg Lys Met Lys Lys Glu Ala Ala Ser Leu Ser Gln Trp
1               5                   10                  15

Leu Ser Ala Thr
            20

<210> SEQ ID NO 29
<211> LENGTH: 20
<212> TYPE: PRT
<213> ORGANISM: Artificial Sequence
<220> FEATURE:
<223> OTHER INFORMATION: Mutated 20-mer peptide

<400> SEQUENCE: 29

Tyr Ala Leu Gln Val Tyr Cys Tyr Asn Ser Asn Phe Pro Lys Gly Met
1               5                   10                  15

Leu Leu Arg Phe
            20

<210> SEQ ID NO 30
<211> LENGTH: 20
<212> TYPE: PRT
<213> ORGANISM: Artificial Sequence
<220> FEATURE:
<223> OTHER INFORMATION: Mutated 20-mer peptide

<400> SEQUENCE: 30

Asp Tyr Arg Thr Val Ser Asn Leu Ile Leu Thr Gly Pro Arg Met Ile
1               5                   10                  15

Val Met Glu Val
            20

<210> SEQ ID NO 31
<211> LENGTH: 20
<212> TYPE: PRT
<213> ORGANISM: Artificial Sequence
<220> FEATURE:
<223> OTHER INFORMATION: Mutated 20-mer peptide

<400> SEQUENCE: 31

Ala Pro Ser Trp Pro Leu Ser Ser Ser Val Pro Ser Gln Lys Pro Thr
1               5                   10                  15

Arg Ala Ala Thr
            20

<210> SEQ ID NO 32
<211> LENGTH: 20
<212> TYPE: PRT
<213> ORGANISM: Artificial Sequence
<220> FEATURE:
<223> OTHER INFORMATION: Mutated 20-mer peptide

<400> SEQUENCE: 32

Val Pro Ser Gln Lys Pro Thr Arg Ala Ala Thr Val Ser Val Trp Ala
1               5                   10                  15
```

```
Ser Cys Ile Leu
        20

<210> SEQ ID NO 33
<211> LENGTH: 20
<212> TYPE: PRT
<213> ORGANISM: Artificial Sequence
<220> FEATURE:
<223> OTHER INFORMATION: Mutated 20-mer peptide

<400> SEQUENCE: 33

Gly Pro Ser Gly Gln Phe Thr His Glu Phe Asp Gly Asp Glu Glu Phe
1               5                   10                  15

Tyr Val Asp Leu
        20

<210> SEQ ID NO 34
<211> LENGTH: 5
<212> TYPE: PRT
<213> ORGANISM: Artificial Sequence
<220> FEATURE:
<223> OTHER INFORMATION: linker polypeptide of CAR
<220> FEATURE:
<221> NAME/KEY: MISC_FEATURE
<222> LOCATION: (1)..(5)
<223> OTHER INFORMATION: May be repeated from 0 to 5 additional times.

<400> SEQUENCE: 34

Gly Gly Gly Gly Ser
1               5
```